United States Patent
Pawliszyn et al.

(10) Patent No.: US 7,259,019 B2
(45) Date of Patent: Aug. 21, 2007

(54) MULTIPLE SAMPLING DEVICE AND METHOD FOR INVESTIGATING BIOLOGICAL SYSTEMS

(76) Inventors: Janusz B. Pawliszyn, 383 Dunvegan Drive, Waterloo, Ontario (CA) N2K 1W7; Heather L. Lord, 7 Mary Street, Branchton, Ontario (CA) N0B 1L0; Marcel Musteata, 254-350 Columbia Street, Waterloo, Ontario (CA) N2L 6P6

( * ) Notice: Subject to any disclaimer, the term of this patent is extended or adjusted under 35 U.S.C. 154(b) by 0 days.

(21) Appl. No.: 11/206,804

(22) Filed: Aug. 19, 2005

(65) Prior Publication Data

US 2005/0276727 A1   Dec. 15, 2005

Related U.S. Application Data

(63) Continuation-in-part of application No. 10/506,827, filed as application No. PCT/CA03/00311 on Mar. 6, 2003.

(60) Provisional application No. 60/364,214, filed on Mar. 11, 2002, provisional application No. 60/393,309, filed on Jul. 3, 2002, provisional application No. 60/421,001, filed on Oct. 25, 2002, provisional application No. 60/421,510, filed on Oct. 28, 2002, provisional application No. 60/427,833, filed on Nov. 21, 2002, provisional application No. 60/604,631, filed on Aug. 27, 2004.

(51) Int. Cl.
| | |
|---|---|
| *G01N 1/18* | (2006.01) |
| *G01N 21/00* | (2006.01) |
| *G01N 31/22* | (2006.01) |
| *C12M 1/34* | (2006.01) |
| *C12M 3/00* | (2006.01) |
| *B01L 3/00* | (2006.01) |
| *B01L 9/00* | (2006.01) |
| *B01L 11/00* | (2006.01) |
| *B32B 5/02* | (2006.01) |
| *C23C 16/52* | (2006.01) |
| *B05D 1/12* | (2006.01) |
| *B05D 7/22* | (2006.01) |

(52) U.S. Cl. .............. 436/178; 436/177; 435/287.1; 435/287.2; 435/287.9; 422/57; 422/58; 422/101; 422/102; 422/104; 422/119; 427/8; 427/180; 427/181

(58) Field of Classification Search ............. 436/177, 436/178; 435/287.1, 287.2, 287.9; 422/57, 422/58, 102, 104, 119, 101; 427/8, 180, 427/181
See application file for complete search history.

(56) References Cited

U.S. PATENT DOCUMENTS 5,120,510 A   6/1992   Gourley et al.

(Continued)

FOREIGN PATENT DOCUMENTS

DE   199 05 239   8/2000

OTHER PUBLICATIONS

Zhang et al., "Solid-Phease Microextraction", *Analytical* Chemistry, vol. 66, No. 17, Sep. 1, 1994, pp. 844-853.

(Continued)

*Primary Examiner*—Long V. Le
*Assistant Examiner*—Jacqueline A. DiRamio
(74) *Attorney, Agent, or Firm*—Kathleen E. Marsman; Borden Ladner Gervais LLP

(57) ABSTRACT

Multiwell plate applications are describe for use with a plurality of fibres having an extraction phase coated thereon in combination with a positioning device. The device and method described are able to perform adsorption of components of interest from a biological system in high volume.

42 Claims, 58 Drawing Sheets

U.S. PATENT DOCUMENTS

| | | | |
|---|---|---|---|
| 5,424,187 | A | 6/1995 | Shor et al. |
| 5,464,395 | A | 11/1995 | Faxon et al. |
| 5,479,923 | A | 1/1996 | Rantala |
| 5,640,470 | A | 6/1997 | Iyer et al. |
| 5,691,206 | A | 11/1997 | Pawliszyn |
| 5,693,228 | A | 12/1997 | Koehler et al. |
| 6,287,521 | B1 | 9/2001 | Quay et al. |
| 6,689,603 | B2 | 2/2004 | Pompidou et al. |
| 6,730,096 | B2 | 5/2004 | Basta |
| 6,743,180 | B1 | 6/2004 | Van Bockel |
| 2002/0034827 | A1* | 3/2002 | Singh et al. ............... 436/177 |
| 2003/0135195 | A1 | 7/2003 | Jimenez et al. |
| 2003/0180954 | A1 | 9/2003 | Riviere et al. |
| 2003/0183758 | A1 | 10/2003 | Colburn et al. |
| 2004/0171169 | A1* | 9/2004 | Kallury et al. ............. 436/178 |
| 2005/0032237 | A1* | 2/2005 | Sandra et al. .............. 436/174 |
| 2005/0142033 | A1* | 6/2005 | Glezer et al. ............... 422/58 |

OTHER PUBLICATIONS

Moneti et al., "Solid-phase Microextraction of Insect Epicuticular Hydrocarbons for Gas Chromatographic/Mass Spectrometric Analysis", *Rapid Communications in Mass Spectrometry*, vol. 11, 1997, pp. 857-862.

Frérot et al., "Solid Phase Microextraction (SPME): A New Tool in Pheromone Identification in Lepidoptera", *J. High Resol. Chromatography*, vol. 20, Jun. 1997, pp. 340-342.

Smith et al., "Solid-Phase Microextraction as a Tool For Studying Volatile Compounds in Frog Skin", *Chemistry and Ecology*, vol. 17, Aug. 3, 2000, pp. 215-225.

Heinze, "Ultramicro-electrodes in Electrochemistry", *Angew. Chem. Int. Ed. Engl.*, vol. 32, 1993, pp. 1268-1288.

Whang et al., "Solid phase microextraction coupled to capillary electrophoresis", *Anal. Commun.*, vol. 25, Sep. 24, 1998j pp. 353-356.

Jackson et al., "Mass spectrometry for genotyping: an emerging tool for molecular medicine" *Molecular Medicine Today*, vol. 6, Jul. 2000, pp. 271-275.

Namera et al., "Analysis of anatoxin-a in aqueous samples of solid-phase microextraction coupled to high-performance liquid chromatography with fluorescence detection and on-fiber derivatization", *Journal of Chromatography A*, vol. 963, Jul. 19, 2002, pp. 295-302.

\* cited by examiner

Fibre with PAN membrane (up) and Original Fibre Before Coating

Blood = SPME extraction from whole blood
Plasma = Standard analysis of plasma
SOF-PPY = Standard in the fiber method with PPY coatings
SOF-PEG = Standard in the fiber method with PEG coatings Blood = SPME extraction from whole blood
Plasma = Standard analysis of plasma
SOF-PPY = Standard in the fiber method with PPY coatings
SOF-PEG = Standard in the fiber method with PEG coatings Blood = SPME extraction from whole blood
Plasma = Standard analysis of plasma
SOF-PPY = Standard in the fiber method with PPY coatings
SOF-PEG = Standard in the fiber method with PEG coatings

MULTIPLE SAMPLING DEVICE AND METHOD FOR INVESTIGATING BIOLOGICAL SYSTEMS

This application is a continuation-in-part of U.S. patent application Ser. No. 10/506,827, filed Sep. 7, 2004, derived from International Patent Application PCT/CA2003/0000311 filed Mar. 6, 2003. Further, this application is entitled to the benefit of and claims priority to U.S. Patent Application 60/364,214 filed Mar. 11, 2002; U.S. Patent Application 60/393,309 filed Jul. 3, 2002; U.S. Patent Application 60/421,001, filed Oct. 25, 2002; U.S. Patent Application 60/421,510 filed Oct. 28, 2002; and U.S. Patent Application 60/427,833 filed Nov. 21, 2002. Additionally, this application is entitled to the benefit of and claims priority to U.S. Patent Application 60/604,631 filed Aug. 27, 2004. The entirety of each document is incorporated herein by reference.

FIELD OF THE INVENTION

The present invention relates generally to multiple sampling devices and methods for quantifying or identifying components of interest in a biological system, such as in an animal.

BACKGROUND OF THE INVENTION

Presently, if one wants to accurately assess the concentrations of chemicals or drugs inside a living animal a sample of the blood or tissue to be studied is removed from the animal and taken to an analytical laboratory to have the chemicals of interest extracted and quantified. Typically a first step is a pre-treatment of the sample to convert it to a form more suitable for chemical extraction. In the case of blood this may be by the removal of blood cells and/or some blood components by the preparation of serum or plasma. In the case of a tissue sample this may be by many processes including freezing, grinding, homogenizing, enzyme treatment (eg. protease or cellulase) or hydrolysis. Subsequently chemicals of interest are extracted and concentrated from the processed sample. For example serum samples may be subjected to liquid-liquid extraction, solid phase extraction or protein precipitation followed by drying and reconstitution in an injection solvent. A portion of the injection solvent is introduced to an analytical instrument for chromatographic separation and quantification of the components. This method produces accurate results with high specificity for the compound of interest, but is time consuming and labour intensive. Also, because of the large number of steps in the process there is a significant chance of errors in sample preparation impacting the results. This method has good sensitivity and selectivity and accuracy for the target compounds but is limited in that the chemical balance the chemicals exist in inside the animal is disrupted during sampling. In many cases this disruption reduces the value of the results obtained, and in some cases makes this technique inappropriate for the analysis. Where the blood volume removed is a high proportion of the total blood volume of the animal, as is commonly the case when mice are used, the death of the animal results. This means that a different animal must be used for each data point and each repeat. By eliminating the need for a blood draw in this case, fewer animals would be required for testing and a significant improvement in inter-animal variation in the results would be achieved.

Alternatively biosensors have been developed for some applications in analysis of chemical concentrations inside animals. In this case a device consisting of a specific sensing element with associated transducer is implanted and produces a signal collected by an electronic data logger that is proportional to the chemicals to which the sensor responds. The main limitations of this type of device are that they normally respond to a spectrum of chemicals rather than having specificity for only one chemical. Of the spectrum of chemicals to which the sensor responds, some produce a greater and some a lesser response. Sensors are also susceptible to interferences where another chemical present in a system interferes with the response produced by the target chemicals. For these reasons biosensors are normally limited in terms of accuracy and precision. Finally biosensors are typically not as sensitive to low chemical concentrations as state of the art stand alone detectors such as mass spectrometers that are used in the above mentioned conventional analysis techniques and in solid phase microextraction. A strength of this technology is that the chemical balance in the system under study is not disturbed.

The in vivo procedure described here is a significant departure from conventional 'sampling' techniques, where a portion of the system under study is removed from its natural environment and the compounds of interest extracted and analyzed in a laboratory environment. There are two main motivations for exploring these types of configurations. The first is the desire to study chemical processes in association with the normal biochemical milieu of a living system, and the second is the lack of availability or impracticality frequently associated with size of removing suitable samples for study from the living system. Newer approaches that extend the applicability of conventional SPME technology, where an externally coated extraction phase on a micro fibre is used, seem to be logical targets for the development of such tools. As with any microextraction, because compounds of interest are not exhaustively removed from the investigated system, conditions can be devised where only a small proportion of the total compounds and none of the matrix are removed, thus avoiding a disturbance of the normal balance of chemical components. This could have a benefit in the non-destructive analysis of very small tissue sites or samples. Finally because extracted chemicals are separated chromatographically and quantified by highly sensitive analytical instruments, high accuracy, sensitivity and selectivity are achieved.

With the current commercially available SPME devices a stationary extraction polymer is coated onto a fused silica fibre. The coated portion of the fibre is typically 1 cm long and coatings have various thicknesses. The fibre is mounted into a stainless steel support tube and housed in a syringe-like device for ease of use. Extractions are performed by exposing the extraction polymer to a sample for a pre-determined time to allow sample components to come into equilibrium with the extraction phase. After extraction the fibre is removed to an analytical instrument (typically a gas or liquid chromatograph) where extracted components are desorbed and analysed. The amount of a component extracted is proportional to its concentration in the sample (J. Pawliszyn "Method and Device for Solid Phase Microextraction and Desorption", U.S. Pat. No. 5,691,206.).

To date commercial SPME devices have been used in some applications of direct analysis of living systems. For example they have been applied for the analysis of airborne pheromones and semiochemicals used in chemical communications by insects (Moneti, G.; Dani, F. R.; Pieraccini, G. T. S. *Rapid Commun. Mass Spectrom.* 1997, 11, 857-862.), (Frerot, B.; Malosse, C.; Cain, A. H. *J. High Resolut. Chromatogr.* 1997, 20, 340-342.) and frogs (Smith, B. P.;

Zini, C. A.; Pawliszyn, J.; Tyler, M. J.; Hayasaka, Y.; Williams, B.; Caramao, E. B. *Chemistry and Ecology* 2000, 17, 215-225.) respectively. In these cases the living animals were non-invasively monitored over time by assessing the chemical concentrations in the air around the animal, providing a convenient means to study complicated dynamic processes without interference.

The current commercial devices do, however, have some limitations for in vivo analysis inside a living animal. Firstly, the application to chemical analysis inside animals requires greater robustness in both the extraction phase and the supporting fiber core. In addition, most of the extraction phases currently available are better suited for more volatile and less polar compounds. Only one phase is suitable for liquid chromatography (LC) applications (carbowax/templated resin). Analytes of interest that typically circulate in living systems are less volatile and more polar and require LC analysis, so new or modified extraction phases are indicated. The overall dimension of the current device is typically too large for direct in vivo analysis and for direct interfacing to microanalytical systems, the time required for the LC extraction phase to come into equilibrium with chemicals in a sample is relatively long (typically 1 hr or more in a well-stirred sample) and analysis is sensitive to degree of convection in the sample. Also the present SPME devices cannot be conveniently coupled to positioning devices necessary for in-vivo investigation at a well-defined part of the living system.

It is, therefore, desirable to provide a method and a device that allows minimally invasive sampling, quantification or analysis of a biological system.

SUMMARY OF THE INVENTION

It is an object of the present invention to obviate or mitigate at least one disadvantage of previous devices and methods for evaluating components of interest in biological systems.

According to an aspect of the invention there is provided a device for measuring or identifying one or more component of interest from liquid samples arranged in a plurality of wells in a multiwell plate. The device comprises a plurality of fibres, each having a distal end at least partially coated with an extraction phase for absorbing the component of interest; and a positioning device for guiding the coated distal end of each fibre into a submerged position within the plurality of wells of a multiwell plate. The positioning device is also capable of removing the fibres from the wells.

Additionally, according to the invention there is provided a method of measuring or identifying one or more component of interest in liquid samples arranged in a plurality of wells in a multiwell plate. The method comprises the steps of simultaneously submerging a distal end of a plurality of fibres in said plurality of wells, the distal end of each fibre being at least partially coated with an extraction phase for adsorbing the component of interest from the liquid sample; adsorbing the component of interest onto the extraction phase for a pre-determined period of time; removing the fibres simultaneously from the wells; positioning the extraction phase into an analytical instrument for desorption; and measuring or identifying the component of interest.

Further, the invention provides a method of measuring or identifying one or more component of interest in liquid samples arranged in a plurality of wells in a multiwell plate. The method comprises the steps of: simultaneously submerging a distal end of a plurality of fibres in the plurality of wells, the distal end of each fibre being at least partially coated with an extraction phase for adsorbing the component of interest from the liquid sample; adsorbing the component of interest onto the extraction phase for a pre-determined period of time; removing the fibres simultaneously from the wells; desorbing the extraction phase in an organic solvent; removal of organic solvent and reconstitution of the component of interest into a mobile phase for measurement or identification in an analytical instrument.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Figure 1:
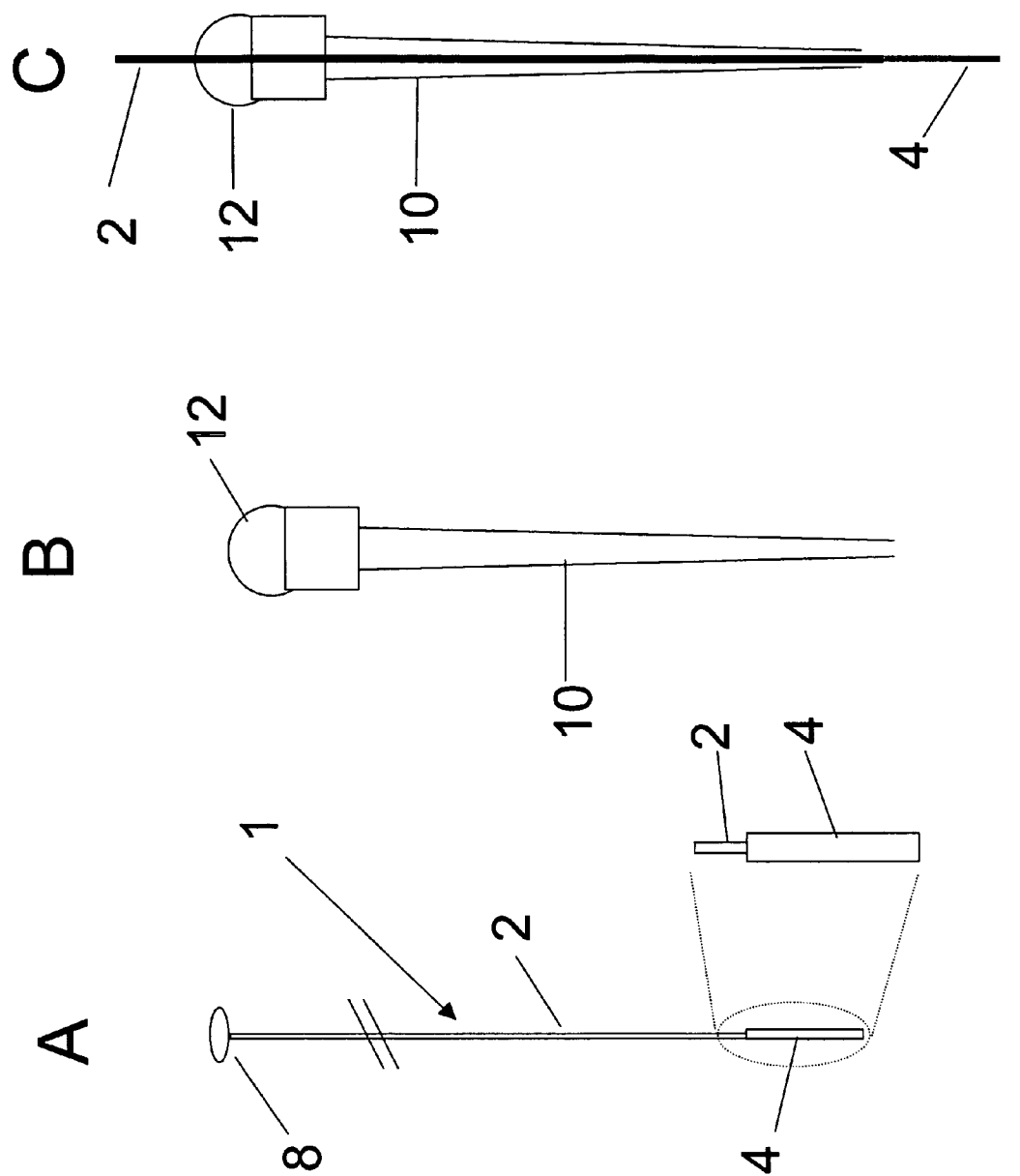
FIG. 1 shows a general schematic of device design according to an embodiment of the invention.

The invention relates to a device and method based on coated fibre, optionally in combination with a positioning device, or analytical technologies particularly useful for in vivo studies of compounds of interest (identities and concentrations) for example in biological systems, animals, or parts of animals.

According to an aspect of the invention, a device for measuring or identifying a component of interest from liquid samples is provided. The liquid samples are arranged into a plurality of containers, such as wells of a multiwell plate. The device comprises a plurality of fibres, each having a distal end at least partially coated with an extraction phase for absorbing the component of interest; and a positioning device for guiding the coated distal end of the fibres into a submerged position within the plurality of wells of a multiwell plate. The positioning device also serves to remove the fibres from the wells.

The positioning device may optionally be used to position the fibres into an analytical instrument. Further, the positioning device may be incorporated as a component of an autosampler. Optionally, the positioning device and guide may be a component of a robotic system.

The positioning device is capable of positioning the fibers in such a way that the fibers can sample the appropriate part of the investigated system, or can sample in multiple wells. The positioning device could be a cover plate, capable of positioning the fibers. A plate having a plurality of fibers extending therefrom in a brush-like manner, can be considered as the positioning device according to the invention. Such a plate can be a coverplate to a multiwell plate. Such a coverplate can be adapted to fit overtop of a multiwell plate so that each fiber or a plurality of fibers may be positioned to become simultaneously submerged into the wells of a multiwell plate.

If a guide is provided as a component of the positioning device, it may be used to guide the fibers into appropriate positions. For example, in the case of an automated analysis multiwell plate, the positioning device may comprise both a plate holding the fibers and an arm (such as a robotic arm) to move the plate from the extraction position to the desorption position. The arm itself may be considered as a guide.

Optionally, the positioning device may comprise a platform on which a multiwell plate is based or positioned, the platform being capable of becoming positioned into a plurality of different positions, depending on the desired application.

The multiwell plate may be of any type having wells formed therein. Optionally, the wells may have openings dimensioned to produce an air tight seal around each fiber upon placement of a fiber in the well.

A mounting plate may optionally be used for mounting each fiber in a position corresponding to a counterpart well on the multiwell plate. In the case where a mounting plate is present, the positioning device may include a guide for moving the mounting plate so the coated distal end of each fibre is submerged in a well of the multiwell plate. The guide may also be involved in removing fibres from the wells, and positioning the fibres into a multiwell plate containing a desorption solvent. Optionally, the guide may be able to direct the fibre into an analytical instrument.

An agitator may be employed with the device for activating agitation during contact of the fibers with the sample. The agitator may optionally be used to activate agitation when the fibers are submerged in the wells. Exemplary agitators include orbital shakers, sonicators, vibrators and stirrers.

As a further option, more than one fiber may be present per well, and each fibre within a well may have the same or a different extraction phase coated on it. The extraction phase may be any phase capable of binding, absorbing, or otherwise adsorbing a compound of interest. Typically, the extraction phase comprises a polymeric composition such as substituted or unsubstituted poly(dimethylsiloxane), polyacrylate, poly(ethylene glycol), ionic liquid or polypyrrole. Ionic liquids include such materials that are amorphous, with high or rapid diffusion coefficients that are not solids, but behave as liquids and as polymers. Generally, ionic liquids do not swell in water. Such liquids allow fast extraction of polar analytes, due to a high polarity and high diffusivity. Exemplary ionic liquids that may be used for such a purpose are reviewed by Baker et al. in "An analytical view of ionic liquids" (Analyst, 2005; 130:800-808), the entirety of which is herein incorporated by reference.

Further, the extraction phase may comprises a bioaffinity agent on the surface of a fibre. For example, such a bioaffinity agent may be a selective cavity, a molecular recognition moiety, a molecularly imprinted polymer, or an immobilized antibody. Additionally, a probe with a pre-activated surface to which a user can attach a bioaffinity agent or biorecognition unit may be used as the extraction phase. In this embodiment, the end user may attach a unit of interest to the pre-activated surface, so that, at the time of sale, the bioaffinity agent or biorecognition unit is not present.

The extraction phase may optionally be formed in the configuration of a thin flat membrane on the distal end of a fiber.

The fibers may be made of fused silica, metal or metal alloy for example biocompatible titanium alloys.

The extraction phase is at least partially coated with a biocompatible protection layer, for example, one made from poly(ethylene glycol), poly(hydroxyethyl methacrylate), poly(acrylamide), poly(N,N-dimethyl acrylamide), dextran, poly(acrylonitrile) and derivatized cellulose. Optionally, the extraction phase additionally comprises derivatized silica.

A bioaffinity agent may be included in the extraction phase. Such an agent may be, for example, a selective cavity, a molecular recognition moiety, a molecularly imprinted polymer, an immobilized antibody, or an aptimer. In the case of an immobilized antibody, the antibody may be attached to metal or metal alloy wire (as the fibre) coated with polyimide, as prepared by uniform coating of the polymer on the wire.

The extraction phase may include a mixture of poly (ethylene glycol) and derivatized silica, for example silica derivatized with a chemically immobilized stationary phases, such as HPLC or SPE phases, for example, a C-18 phase. Further, the extraction phase may contain a calibrant. Bonded silica sorbents representing derivatized silica that may be available for column backings include polar sorbents: C18, Octadecyl; C8, Octyl; C2, Ethyl; CH, Cyclohexyl; PH, Phenyl; polar sorbents: CN, Cyanopropyl; 2OH, Diol; SI, Silica; NH2, Aminopropyl; PSA, N-propylethylenediamine; and ion exchange sorbents: SCX, Benzenesulfonylpropyl; PRS, Sulfonylpropyl; CBA, Carboxyethyl; DEA, Diethylaminopropyl; and SAX, Trimethylaminopropyl.

In one embodiment of the invention, the wells of the multiwell plate may have two positions: closed and open. A closed position may be assumed when it is desirable for the fiber to be sealed in the well. An opened position can be assumed where the fiber is exposed to sample, desorption solvent or an analytical instrument.

Additionally, according to the invention there is provided a device and method to store fibres for in-vivo sampling and then desorb components of interests for analysis and determination. For the multiwell plate format, there may optionally be provided a multiple well sealing and handling system that would collect fibres after exposure to in vivo experimentation. This allows individual fibres, which may be provided in the form of a needle, to be sealed in an assembly. A sealing plate may be used, for example, after a fiber has been exposed to an investigated system so as to prevent loss of analytes from the extraction phase. Further elaboration on this embodiment is provided in Example 6.

Additionally, according to the invention there is provided a method to calibrate in vivo extraction using standards in the extraction phase. Standards included in the extraction phase may be used to calibrate the analyte of interest on the basis of the rate of desorption, or alternatively on the basis of equilibration. In the case where calibration is determined on the basis of rates, a shorter exposure time to the sample is required, since complete equilibration is not necessary. A fundamental discussion of the behaviour of a fibre is provided in the following publications, each of which is incorporated herein by reference: Chen et al., "Standards in the extraction phase, a new approach to calibration of microextraction processes." Analyst 2004; 129:702-703; Chen and Pawliszyn, "Kinetics and the on-site application of standards in a solid-phase microextraction fiber" Anal. Chem. 2004; (Oct. 1) 76 (19): 5807-5815; and Wang et al., "Equilibrium in-fibre standardisation technique for solid-phase microextraction" J. Chromatography 2005; 1072: 13-17.

According to an aspect of the invention, a method of measuring or identifying one or more component of interest in liquid samples arranged in a plurality of wells in a multiwell plate is described. Distal ends of a plurality of fibres are submerged simultaneously into a plurality of wells, the distal end of each fibre being at least partially coated with an extraction phase for adsorbing the component of interest from the liquid sample. Adsorption of the component of interest onto the extraction phase for a predetermined period of time occurs. The fibers are then removed simultaneously from the wells.

Following this, there are at least two options for subsequent analysis. As one option, he extraction phase is then positioned directly into an analytical instrument for desorption, and the component of interest is measured or identified. Examples of analytical instruments that may be used are MALDI analysis or a multichannel micromachined microfuidic device.

As another option, after removal of the fiber from the biological system, the extraction phase is desorbed in an organic solvent. The solvent can be removed by any acceptable method, such as evaporation, and the analyte remaining can be reconstituted into a mobile phase for measurement or identification in an analytical instrument. In this way, the volume and solvent used for the reconstituted sample can be controlled.

For certain applications, the extraction phase may initially be positioned within an animal or tissue. Plant tissues may also be used (for example, grapes) if the analyte of interest resides therein.

The method of the invention may be used in pharmacokinetic studies, wherein observation of analyte levels in a biological system over time is desirable to conduct with little or no blood or biological fluid removal from the system. In the case where blood samples would normally be drawn periodically for pharmacokinetic studies, the invention advantageously allows similar observations without removal of blood volume from the subject.

The extraction phase may specifically adsorb the one or more component of interest, and is preferably located at a terminal end (or "distal" end) of the fibre.

The period of time for which the fibre is positioned within the animal or animal tissue can be any acceptable time allowing adsorption of a detectable amount of the component of interest. For example, this time may be equivalent to equilibration time for a component of interest, or it can be less than equilibration time for a component of interest.

The component of interest can be any desirable component. For example, it may be a bacteria, viruses, sub-cellular components, biopolymers, DNA, proteins, drugs, drug metabolites, hormones, vitamins, environmental contaminants, chemicals, or cells. Any component capable of detection can be selected.

The animal or animal tissue can be selected from the group consisting of single cell animals, live eggs, mice, rats, rabbits, dogs, sheep, pigs, monkeys and humans. As discussed further herein, an embodiment of the invention requires only samples, and is not necessarily conducted in an animal or in animal tissue. The animal tissue could be, for example, isolated cells and organs.

The fibre may be positioned within a blood vessel, and this embodiment would allow analysis of a component of interest adsorbed from blood flowing through said blood vessel. Optionally, the step of positioning said fibre comprises guiding the fibre into position within the blood vessel using a catheter. Other areas in an animal in which the fibre may be positioned include a) muscle, brain, soft tissue, or organ of said animal; and the component of interest is adsorbed from interstitial fluid or intracellular fluid; b) an inner part of spine, scull or bone; and the component of interest can be adsorbed from the bone, inner fluids including spinal fluid, bone marrow or brain fluid; or c) a cell of an animal, and an adsorbed component is extracted from the inner cellular fluid or sub-cellular component of a single cell of an animal. Of course, the invention is not limited to these examples.

During positioning, the fibre may be disposed within a housing having a sealed penetrating end. In this case, the method may include the step of opening the penetrating end once the fibre is positioned as desired within the animal, exposing the extraction phase within said animal.

Alternatively, the fibre may be inactive during said positioning followed by activating the extraction phase using change of electrical potential or optical means to allow adsorption of said component of interest. An example of this could be if the fibre is made of a metal which can be activated to attract certain components. Other possibilities for electrical activation of the fibre are within the scope of the invention.

The invention may use one fibre, or a plurality of fibres arranged as an array or bundle. As used herein, discussion of a fibre in the singular does not preclude the use of more than one fibre, or a bundle of fibres. In the case where a plurality of fibres are used, they may be disposed in a single position within the animal, or they may be disposed in more than one position within said animal, so as to obtain readings from multiple locations simultaneously. The fibre may be one or more optical fibre, such as a bundle of optical fibres.

In one embodiment of the invention, the extraction phase may additionally comprise a strongly bound calibrant which is retained in the extraction phase during the step of adsorbing. Alternatively, a weakly bound calibrant can be used which is released from the extraction phase during the step of adsorbing according to convection conditions and diffusion coefficient. The amount of the weakly bound calibrant remaining after the pre-determined period of time can be observed. This can also be used to deliver a desired compound to the animal or animal tissue.

In another embodiment, a strongly bound reagent may be added to the extraction phase prior to extraction. This reagent may be a strongly bound reagent which reacts with the component of interest. An example of such a strongly bound reagent is one that labels the component of interest with a fluorescence tag. Another example is a reagent such as an enzyme, in which case the component of interest may be a substrate for that enzyme. Such an enzyme may be one that digests a protein directly onto the fibre, for example trypsin or a trypsin cofactor. Further, the reagent may be added to the extraction phase after the step of adsorbing, in which case the reagent subsequently reacts with the component of interest.

The reagent can be added to the extraction phase by spraying or dipping the reagent onto the extraction phase.

The method of the invention may be one in which a polymerase chain reaction (PCR) is conducted directly on the extraction phase. In such an embodiment, the components of interest are DNA or DNA fragments, the fibre is subject to periodic cycles of alternating cooling and heating, the reagent comprises polymerase and nucleic acids, and the method results in a polymerase chain reaction (PCR) on the extraction phase.

The reagent may comprise an ionization matrix utilized in matrix assisted laser desorption and ionization (MALDI). MALDI analysis of the extraction phase can be conducted with any embodiment of the invention amenable to such a method of measurement or compound identification. Any number of analytical instruments may be used with the invention, such as a spectrometer such as a time of flight instrument mass spectrometer (TOFMS) or an ion mobility spectrometer. After desorbing the component of interest from the extraction phase, measurement or identification of the component may occur in an analytical instrument such as a gas chromatograph, a liquid chromatograph, a capillary electrophoresis instrument, a capillary electrochromatography instrument and a microfluidic device. The process of extraction and sample introduction could be done in parallel by using a multi port holding plate and multiwell plate.

The invention may include positioning of the fibre in an analytical instrument after the step of adsorbing. This could, for example involve laser irradiation of the fibre to desorb the component of interest from the extraction phase into the analytical instrument. In such a case, the fibre can be irradiated in a region not coated with the extraction phase, so as to desorb the component.

The invention may allow introduction of the fibre directly into a mass spectrometer prior to the step of desorbing. The fibre may be introduced into a mass spectrometer by insertion into a small solvent volume in a nanospray needle, followed by the step of desorbing, and electrospray of a desorbed component of interest.

After removing the fibre from the animal or tissue, the fibre may be exposed to a high voltage resulting in field desorption of the component of interest directly from the extraction phase into the mass spectrometer.

Separation of components of interest from the extraction phase may occur directly in a separation capillary or channel of the analytical instrument. The step of desorbing may be conducted in a small bore cartridge filled with a desorption solvent following by automated measurement or identification of a component of interest in the analytical instrument. In such a case, the fibre may be placed in the small bore cartridge immediately following the step of removing the fibre from the animal or tissue, and the cartridge can either be analysed immediately or sealed and transported or stored prior to automated measurement or identification.

The invention also relates to a device for adsorbing one or more component of interest from an animal or animal tissue. The device comprises one or more fibre having an at least partially coated end. The end is at least partially coated with an extraction phase for absorbing one or more component of interest. The device also includes a positioning device for guiding the at least partially coated end of the fibre into position within the animal or animal tissue.

Optionally, the fibre diameter can be of millimeter to nanometer dimensions, and formed of any acceptable material that would be amenable for use in the intended application. Such materials may include fused silica, plastic, carbon or metal wire. The fibre may be a plurality of optical fibres formed from fused silica.

Optionally, the fiber may be a hollow tubing having the extraction phase coated on an inside surface of the tubing. In this instance, the tubing may be in communication with a pump capable of draw up or ejecting a sample from the tubing. The pump may be of any acceptable type known for use with tubing. Alternatively, the fibre may be a hollow tubing having the extraction phase coated on an outside surface thereof. In this case, the tubing could be sealed at one end and have a pump in communication with the tubing to blow fluid, such as a gas or liquid, into the tubing. This would allow expansion of the tubing as desired, which could increase the surface area of the extraction phase as required.

The fiber may also be made of metal, such as a needle. In this case, the hollow metal fibre may have the extraction phase coated on the inside of the bore of the needle (the distal end of the fiber). In this way, once the fibre (or needle) draws up sample (such as blood), the sample becomes exposed to the extraction phase. For example, a C18 loaded PEG-coated fibre may be positioned in a vein and exposed to sample, in this case blood. The needle can then be processed in parallel with a number of other needles using a positioning device, such as a plate. Advantageously, this may be used in animals. When in vivo collections are completed, a plurality of samples may be desorbed in parallel.

Whether direct desorbtion or plate drying (desorb in organic solvent, remove solvent and reconstitute as desired) of the extraction phase is used, an interface between the positioning device (such as a plate holding fibres) with the analytical device (such as MALDI-MS) may be provided. This interface is discussed and described in more detail in Example 6. In a particular embodiment, the tips of the fibers may be irradiated or otherwise processed in order to facilitate introduction of analytes through an orifice of the analytical instrument.

The device of the invention may additionally comprise a sheath surrounding the fibre for protection and easy handling.

The extraction phase is advantageously biocompatible, as necessary. Optionally, the fibre may be additionally at least partially coated with a biocompatible protection layer, which can surround the extraction phase. Such a biocompatible protection layer may comprise polypyrrole or derivatised cellulose, or any such polymer as would provide protection.

The extraction phase itself may comprise any composition capable of binding a component of interest. It may, for example be a polymeric composition such as substituted or unsubstituted poly(dimethylsiloxane), polyacrylate, poly (ethylene glycol) or polypyrrole. Alternatively, the extraction phase may have a bioaffinity agent on its surface, such as a selective cavity, a molecular recognition moiety, a molecularly imprinted polymer, or an immobilized antibody. The extraction phase may contain any of these in combination.

The extraction phase can, alternatively be an extraction and ionization matrix for MALDI-TOFMS analysis, and may contain a calibrant molecule, as discussed above.

The fibre may be contained in a housing closed at one end, for opening and exposing the fibre when appropriately positioned within the animal or animal tissue. Such a housing may be a sealed leaf structure, or any other such openable sealant.

The positioning device itself may be a catheter, for those applications where the fibre is guided into a blood vessel, such as a vein, or other tubular biological structures, as discussed in more detail below. Further, the position device may be an x-y-z micro positioning stage, for those applications wherein a tissue can be positioned on such a stage, and its movement finely controlled. The positioning device comprises an automated system, which may be rendered attachable to the animal or animal tissue. The positioning device may additionally be used to position said fibre within an analytical instrument for desorption of the component of interest from the extraction phase. The positioning device can optionally be used to place the fibre directly inside a separation capillary or channel, and could be used to couple the fibre to a laser beam facilitating desorption of a component of interest from the extraction phase. The positioning device may be used to facilitate desorption of a component of interest into an analytical instrument.

In the case where a plurality of fibres are used, these fibres may have the same or a different extraction phase coated thereon, so that more than one component of interest can be detected. More than one extraction phase can be combined on a fibre, so that a variety of components of interest can be detected.

The device may additionally comprise an agitator to cause movement of the coated end of a fibre, for example axial or horizontal movement of the fibre. In the case where the fibre comprises hollow tubing having the extraction phase coated on an inside surface of the tubing, the agitator may force the tubing to draw up a sample into the tubing. This can be effected by mechanical means or by creating a pressure differential forcing the tubing to draw up a sample into the tubing. The agitator may comprise an inflatable balloon.

The invention further relates to a method of measuring or identifying one or more component of interest in liquid samples arranged in a plurality of wells in a multiwell plate. This involves simultaneously submerging a distal end of a plurality of fibres within the plurality of wells, respectively, the distal end of each fibre being at least partially coated with an extraction phase for adsorbing the component of interest from the liquid sample. Following this, the component of interest is adsorbed onto the extraction phase for a pre-determined period of time. The fibres are then simultaneously removed from the wells, and are positioned in an analytical instrument for desorption, and measurement or identification of the component of interest from the extraction phase. Such an analytical instrument may be any of the ones noted above, such as a MALDI analytical instrument or a multichannel micromachined microfuidic device.

The inventive device for measuring or identifying one or more component of interest from liquid samples arranged in a plurality of wells in a multiwell plate, for use with the method described herein comprises a plurality of fibres, each having an at least partially coated distal end, said end being at least partially coated with an extraction phase for absorbing the component of interest. A positioning device is used for guiding the coated distal end of said fibres into a submerged position within the plurality of wells of the multiwell plate, for removing said fibres from said wells, and for positioning said fibres into an analytical instrument.

According to one embodiment, a small sterile device containing a small diameter fibre with an associated extraction phase coated thereon is used. The extraction phase has affinity for one or more compound of interest. After exposure of the extraction phase in vivo, the device may be removed for quantitative or qualitative analysis in an analytical instrument.

A device for in vivo study of chemical concentrations consists of a fibre or wire and associated extraction phase. The fibre or wire may be made of fused silica, metal, carbon, graphite or a polymeric material. The device may or may not have an attached or removable handle. The device may have an associated or removable housing such as an outer needle sheath to provide access for the device to the tissue under study. Preferably the device is introduced to the tissue under study via a standard medical positioning device such as a catheter or microdialysis cannula. After extraction the housing may be retained if it is used in association with desorption, or discarded if it is not so-needed. Where a medical device is used to provide access to the tissue under study, multiple devices may be used with a single catheter for instance, obviating the need to puncture the skin or other tissues separately for each extraction.

A process of carrying out in vivo solid phase microextraction uses a fibre with associated extraction phase, which may or may not have an associated housing. In any case a means is provided to position the device in the tissue for the desired extraction. For extraction the device is left in contact with the tissue under study for a sufficient period of time to allow equilibration with the chemicals in the tissue, insensitivity to convective forces and/or maximal sensitivity. It is likely the device could be used to monitor chemical concentrations in humans or experimental animals such as rats, mice, dogs, sheep or rabbits. Subsequent to sampling the device is placed in an appropriate analytical instrument or desorption device so that at least one chemical component extracted is desorbed for quantification.

The device and process described are used to monitor chemical concentrations in vivo in a living animal, without causing a disruption in the dynamic balance in the animal systems. Some specific benefits can be described. Because no blood need be drawn for the analysis, animals are less stressed. This would allow for more data points to be collected for pharmacokinetic profiles, allowing for better data on which to make drug design decisions. It would also allow or for sampling of blood or tissue drug concentrations at multiple sites in an animal, to better assess the effects of differing metabolic processes in different locations in animals. Where more data points are collected from one animal, a reduction in inter-animal variation in the results arises. This variation can often obscure real pharmacokinetic trends and so by eliminating it, better pharmacokinetic data can be collected. Conventional sampling where a specific sample of blood/tissue is removed from an animal causes a disruption in the normal chemical balance of the animal. Each successive sample enhances the impact on the normal dynamics of the animal. With sampling according to the invention, where only a negligible portion of the analytes of interest are removed, the normal chemical balance remains unperturbed, thus eliminating the effect of sampling itself on the results. Genetic variation in drug metabolism within a population gives rise to differing pharmacokinetics for the same drug among individuals. The device and process described would be beneficial both in monitoring the effect of genetic variation on metabolism of existing drugs, and for directing the design of novel drugs to take advantage of variable genetic profiles for tailored drug design.

Calibration of the device may be achieved in several ways. Where equilibrium extraction is achieved, calibration by comparison to matched in vitro samples is simple and effective. Under non-equilibrium extraction or where it is not possible to match in vitro samples to the in vivo system, calibration may be achieved by pre-loading the fibre with a suitable calibrant. Direct quantification based on analyte physico chemical properties is also possible using spectroscopic analysis of the analytes directly from the fibre.

Optionally, calibrant can be added to the extraction phase to perform internal calibration to quantify components of interest. The rate of loss of calibrant from the extraction phase is used to estimate various degree of convection in the system and the matrix affect facilitating accurate in-vivo or in vitro calibration.

The device accomplishes both sampling and sample preparation during in vivo analyte extraction. Sample preparation may be limited to isolation from sample matrix and concentration in the extraction phase. It may also include additional processing on the fibre. Examples of this are derivatization of analyte to a form with higher sensitivity in detection through either a modification of product polarity or fluorescent tagging, amplification of analyte copy number in the case of DNA analysis to improve signal intensity, and protein or enzymatic digestion in the case of general biomolecules (eg. proteins) to convert them to a form more amenable to instrumental analysis (eg. peptide fragments). In all cases the goal of this on-fibre processing is to enhance detection/quantification of the target analytes.

In the conventional SPME device the overriding goal in device design was optimizing the affinity of the analyte for the extraction phase on the fibre, to maximize analytical sensitivity. In the case of in vivo analysis the issue of coating biocompatibility is equally important. Device design must take into account both biocompatibility and affinity in the extraction phase.

Because of the simplicity inherent in both the device design and the process, multiplexing in both sampling and analysis is much more practical that it has been for conventional analyses. Fibres may be grouped together in bundles, with fibres having either the same or different coatings, allowing for both sampling and quantification from many fibres at once, rather than one at a time.

Another advantage of the device and process is that quantification is performed separately from sampling, using conventional high sensitivity instrumental analysis. This allows better sensitivity and selectivity than are achievable where the detection is coupled directly to the sampling/sample preparation as is the case for biosensors. An interface is used to couple the fibre to the analytical instrument. This may be as simple as the off-line desorption of analytes into solvent filled wells in a multi-well plate, to a more sophisticated dedicated interface for thermal, field, solvent or laser desorption. In the case of a dedicated interface for solvent desorption, small internal diameter coupled with efficient solvent flow enhance desorption kinetics so that analytes may be removed from the fibre as quickly as possible.

Although the discussion thus far has focused on using a device without compounds of interest initially loaded into the extraction phase, to investigate chemical concentrations in a living system, the device described is equally suited to the delivery of a precise amount of a chemical compound to a precisely targeted tissue. If a device is first loaded with a pre-determined amount of compound of interest, it can be accurately positioned at the site of interest, where compounds will move out of the device according to kinetic and/or thermodynamic principles and thus supply the chemical to the tissue. This would be of value in targeted drug dosing where only a specific tissue is exposed to a drug compound.

FIG. 1, part A illustrates an extraction device 1 consists essentially of an extraction phase 4 coated on a fibre or wire 2 to be used with a positioning device to accurately locate the device in a tissue. The entire device is sterilizable by one or more of the conventional means of sterilization, such as autoclave, ethylene oxide, EN or gamma irradiation. The uncoated end of the wire may or may not include a handle 8 to facilitate positioning of the device. The length of the wire is variable depending on the application requirements. The extraction phase 4 could be a polymeric layer prepared on the wire surface, particulate adsorptive or absorptive material glued or otherwise affixed to the wire surface, or immobilized biorecognition agents such as antibodies nucleotides or protein receptors. When constructed of the stainless steel wire described below the extraction device is quite flexible. It will follow curves in a vein or catheter and normally resume a straight configuration when removed. The device is useful for the application of monitoring concentrations of drugs and their metabolites in blood or other tissues, either in single point monitoring or in multiple point (time course) monitoring.

FIG. 1, part B illustrates standard medical catheter is shown in schematic form having a catheter body 10 and a sealing septum 12 (PRN). PRN is the commonly used term for an i.v. adapter to seal a catheter, incorporating a piercable septum, marketed by Beckton Dickinson. In the text that follows applications are described that use such a catheter for intra venous (i.v.) sampling. In practice, catheters are available for accessing other vessels as well, so applications are not limited to i.v. ones. For instance arteries, vessels within organs or capillaries may also be accessed using similar devices.

FIG. 1, part C, illustrates an embodiment comprising the extraction device alone with no support rod and no handle may be introduced to a blood vessel through a previously placed medical catheter 10 with attached PRN 12. The end of the extraction device with the extraction phase 4 may be contained in a sterile hypodermic needle that is used to pierce the PRN and provide access to the catheter. The extraction device is pushed partly into the catheter by means of the support wire 2 and the hypodermic needle is withdrawn. In this case the PRN provides a seal around the device to prevent blood loss. The extraction device 1 is then pushed into the catheter and blood vessel by an appropriate amount so that the extraction phase is exposed to the flowing blood. The catheter is then flushed with saline to prevent clotting in the catheter. After the required time for the extraction of drugs and metabolites the hypodermic needle is once again used to pierce the PRN to provide a port for removal of the extraction device. The extraction device is then removed from the housing, rinsed and packaged for transport for analysis. The coated fiber can be placed inside a micro-syringe as described in U.S. Pat. No. 5,691,206, for easier handling with a catheter or other positioning device.

Figure 2:
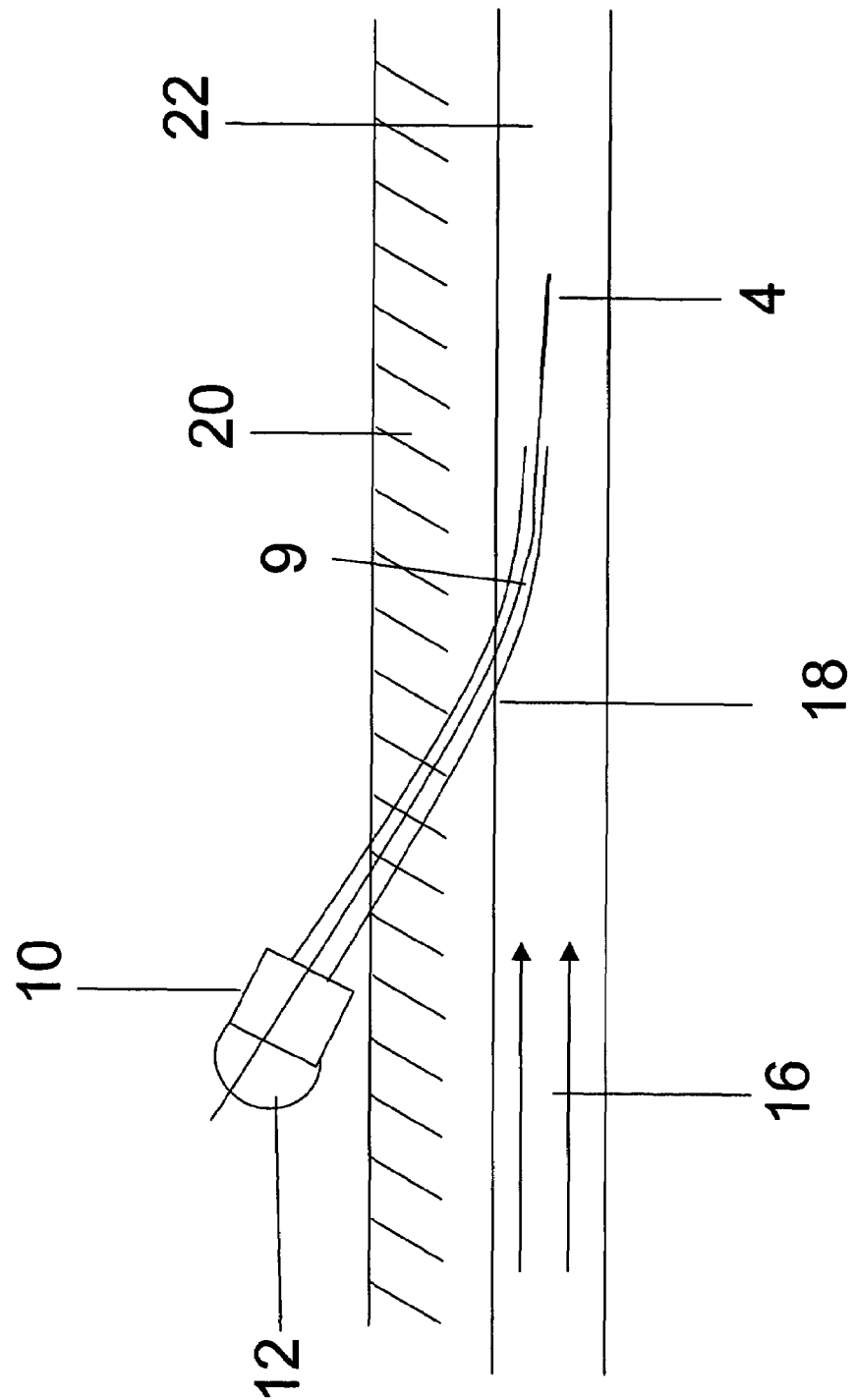
FIG. 2 illustrates the use of a medical catheter to position device accurately within a vein.

FIG. 2 shows the use of a medical catheter 10 passing through the skin 20 and vein wall 18 to position the extraction device 9 with PRN 12 inside a vein 22 with blood flow 16 past the exposed extraction phase 4. In this position the extraction device has been fully depressed through catheter so that the extraction phase is fully exposed to flowing blood outside of catheter. PRN 12 is still accessible to allow for flushing to ensure patency of the catheter.

Figure 3:
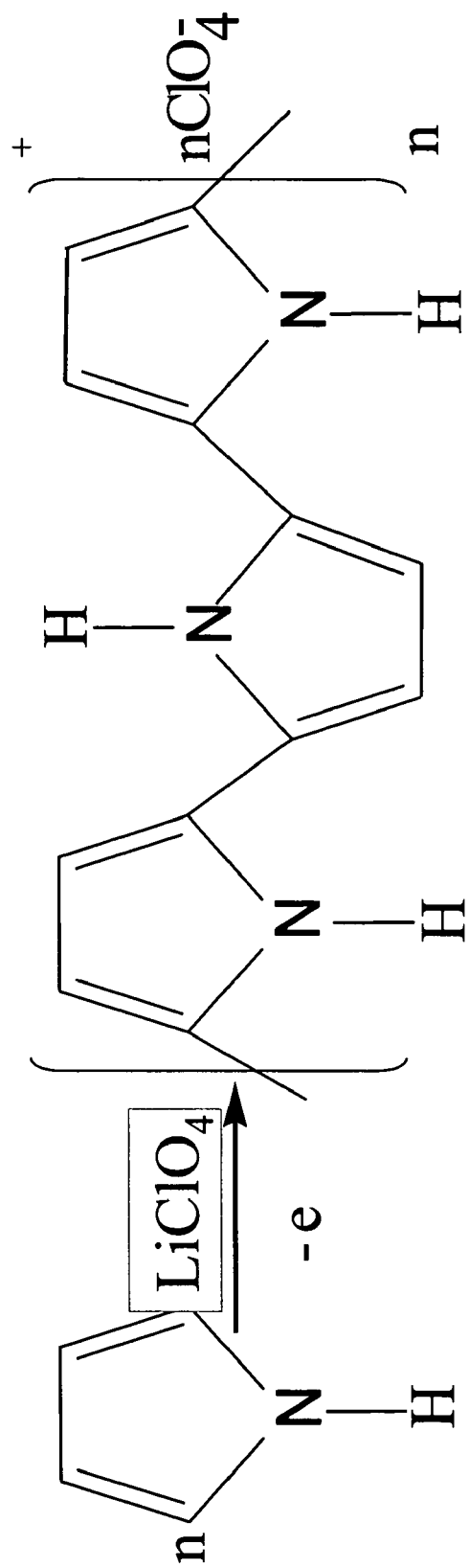
FIG. 3 shows a schematic of the polypyrrole polymerization reaction.

FIG. 3 illustrates a schematic of the polypyrrole polymerization reaction. As an example of an extraction phase, polypyrrole may be deposited onto the surface of a fine metal wire by electrolytic oxidation under conditions of controlled potential The polymer can be prepared on thin stainless steel wire as described below. The resulting polymer can then serve as the extraction phase to extract pre-concentrate drug compounds directly from blood flowing in a vessel. An exemplary preparation of coating a stainless steel wire with polypyrrole is provided in Example 1.

MEDICAL SAMPLING DEVICE

In use it may be desirable to provide a housing or sheath to allow access to the tissue site of interest. The housing is also important to ensure correct positioning of the device at a specific location in the tissue or site under study. This may be by puncture of the skin and/or blood vessel followed by positioning of the phase at a specific site for analysis, incorporation of multiple fibres and agitation means. The housing may also be required to provide a seal to prevent blood from escaping past the device during sampling. The nature of the associated housing will be dependent on the site to be sampled.

FIGS. 4 to 9 provide schematic illustration of options for the devices and described herein.

Figure 4:
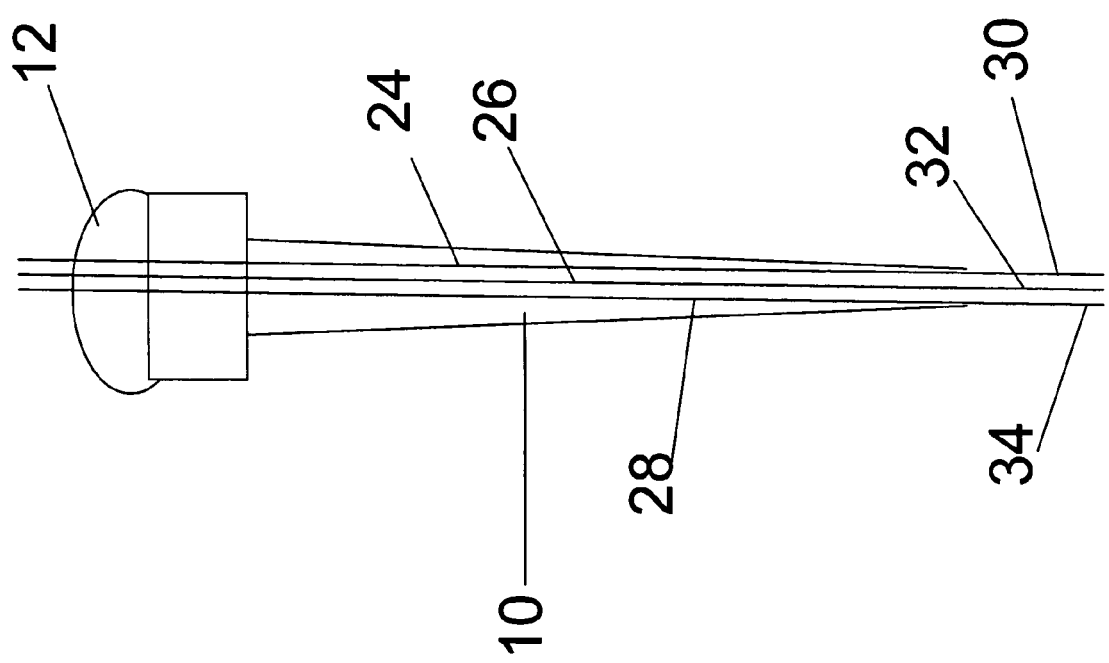
FIG. 4 is a schematic of a catheter with multiple coated fibres.

FIG. 4 shows modifications to the device and a housing for multi-fiber sampling using a commercial catheter. Fibres 24, 26 and 28 are coated by coating 30, 32 and 34 respectively, which can be the same type of coating to increase capacity of the device, or preferentially each fiber having different highly selective coatings, such as antibodies designed to recognized only defined components of interests in a living animal.

The device may also be used for sampling from an unpressurized medical port such as a microdialysis cannula. Because such a port is not pressurized, there is no need for a seal to prevent fluid from flushing past the device during sampling, which obviates the need for an additional sheath or specialized housing during sampling. The device has significant advantages over conventional microdialysis sampling because it is not necessary to either add or remove fluid from the tissue to sample. In conventional microdialysis analysis a portion of the fluid that diffuses into the cannula from the surrounding tissue may be removed for analysis. Alternatively synthetic fluid is pumped into the cannula and then to an analytical instrument for semi-continuous monitoring. In both instances the fluid balance of the tissue is disrupted during sampling, by reduction in volume in the first instance and by dilution in the second. Analysis using the device according to the invention would not disrupt the biochemical balance in the tissue as it does not cause such an imbalance.

Figure 5:
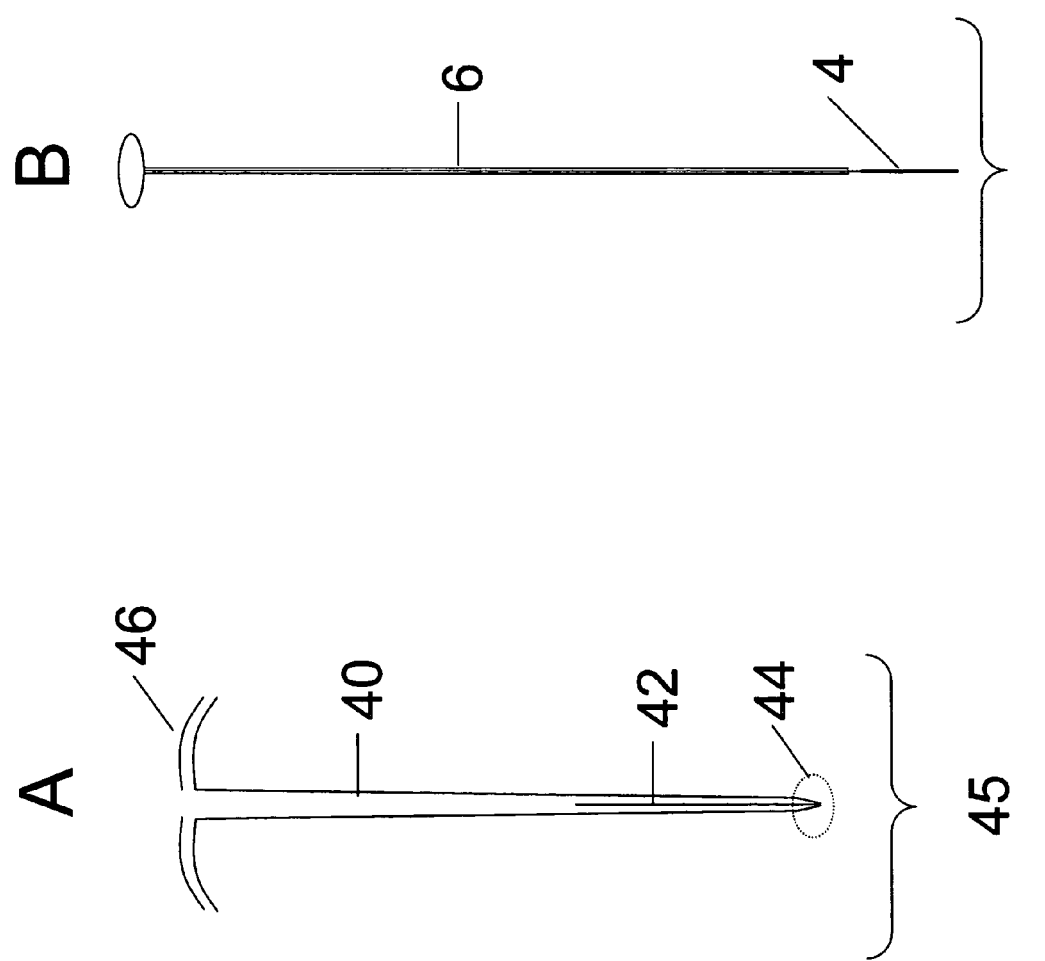
FIG. 5 shows a schematic of housing and device for soft tissue sampling.

FIG. 5 shows a modified housing in part A and extraction device in part B appropriate for sampling directly from soft tissue. When the device is in the retracted position the housing as seen in FIG. 5, part A, is constructed of a rigid tube 40 with a handle 46 and has a sealed tip 44 for penetrating soft tissue. The tip is constructed from two or more leaves separated from each other part way up the housing by a cut or slot 42 and are normally held together by spring action to seal the tip. FIG. 5, part B shows the extraction device supported in a thick tubing 6 for opening up the leaves of the needle end to allow exposure of extraction phase for sampling.

Figure 6:
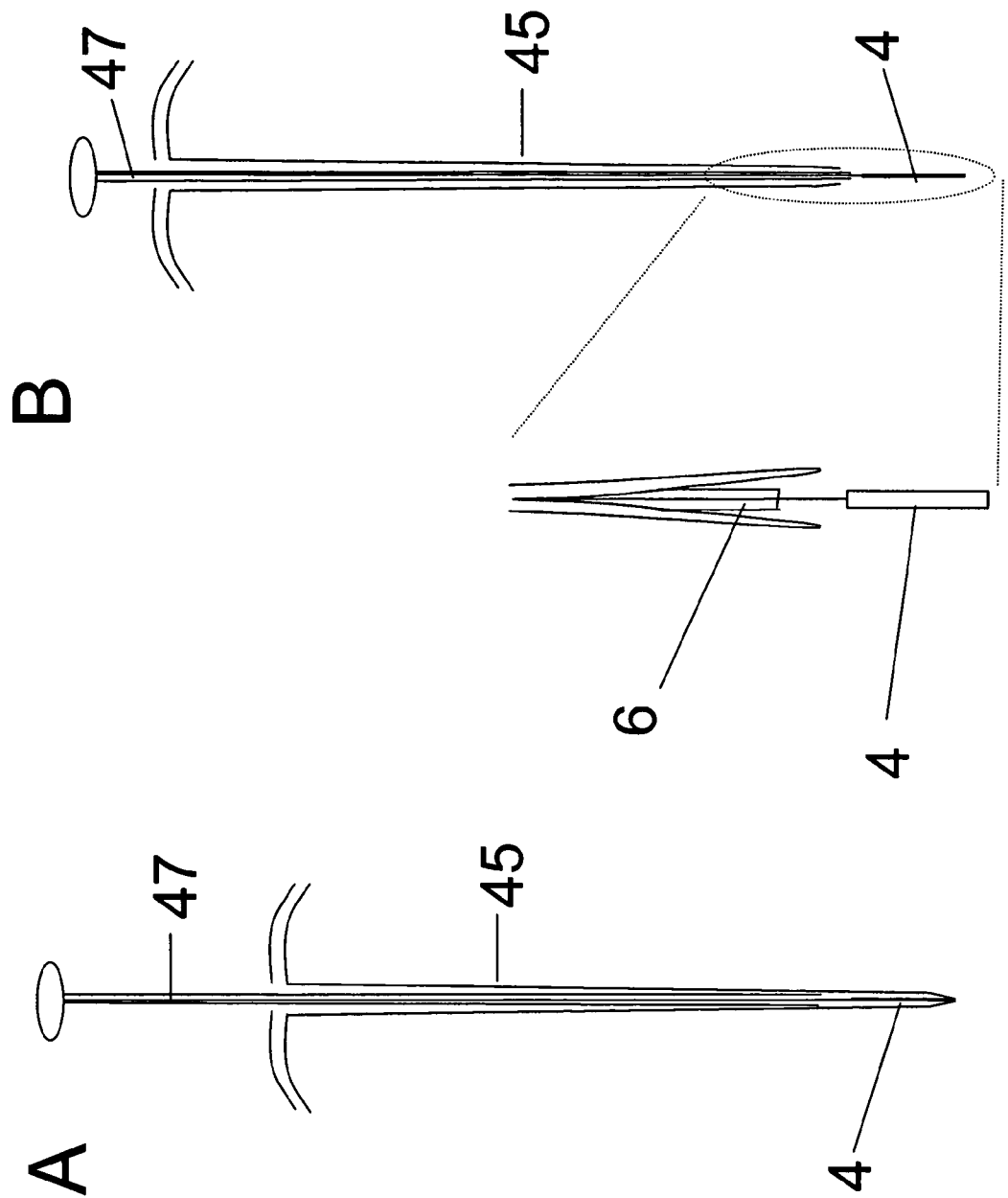
FIG. 6 illustrates operation of housing and device for soft tissue sampling.

FIG. 6 shows a schematic of the use of the extraction device and housing for soft tissue sampling. FIG. 6, part A, shows the extraction device 47 within the housing 45 in retracted position. FIG. 6, part B, shows the extraction device 47 in the housing 45 in exposed position. The supporting wire 6 moves with extraction device to force open the leaves at tip of needle to allow extraction phase on wire to pass through.

Figure 7:
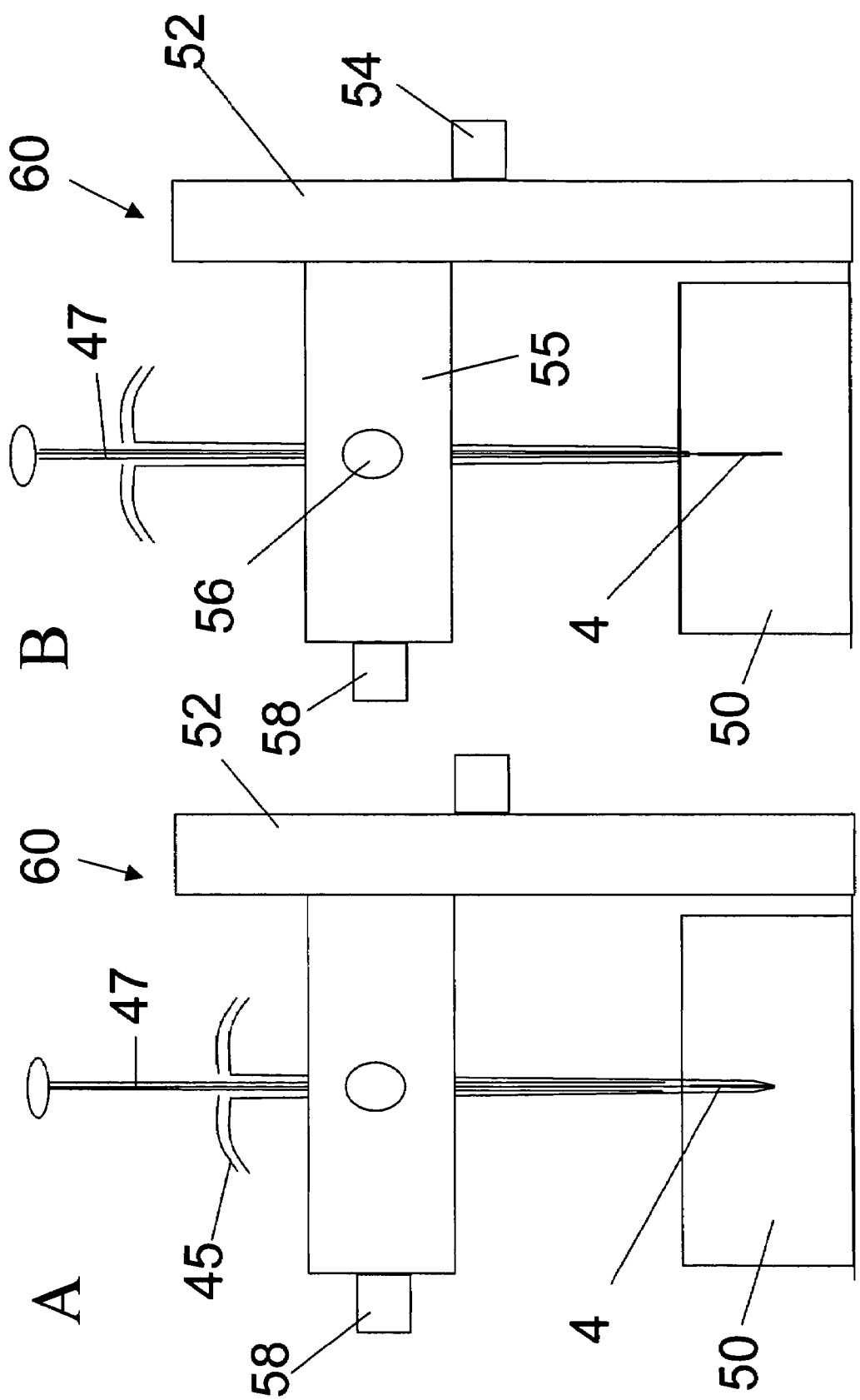
FIG. 7 shows a schematic of use of soft tissue sampling housing to position device for sampling with x-y-z stage.

FIG. 7 illustrates the housing 45 and extraction device mounted in the x-y-z positioning device 60 consisting of the "z" vertical positioning stage 52 with high resolution dial 54 and the x-y stage 55 with appropriate dials 56 and 58 allowing precise positioning of the extraction phase 4 within the sample 50. This positioning system is typically with microscope to monitor insertion and sampling process. The housing is first used to prepare a channel for the device at the required position for sampling (FIG. 7, part A). The housing is then withdrawn slightly while the extraction device 47 is held still. In this way the extraction phase of the device comes into contact with the tissue surrounding the channel prepared by the housing, thus avoiding a plug of tissue from traveling into the housing, and avoiding having the extraction device itself have to bore the channel in the tissue. In this case the device is used to monitor the concentrations of chemicals in the interstital or intracellular fluids in the tissues, as it would not sample chemical that is bound to tissue proteins or membranes. This would be preferred to tissue biopsy both in terms of the simplified sampling and reduced tissue damage.

Figure 8:
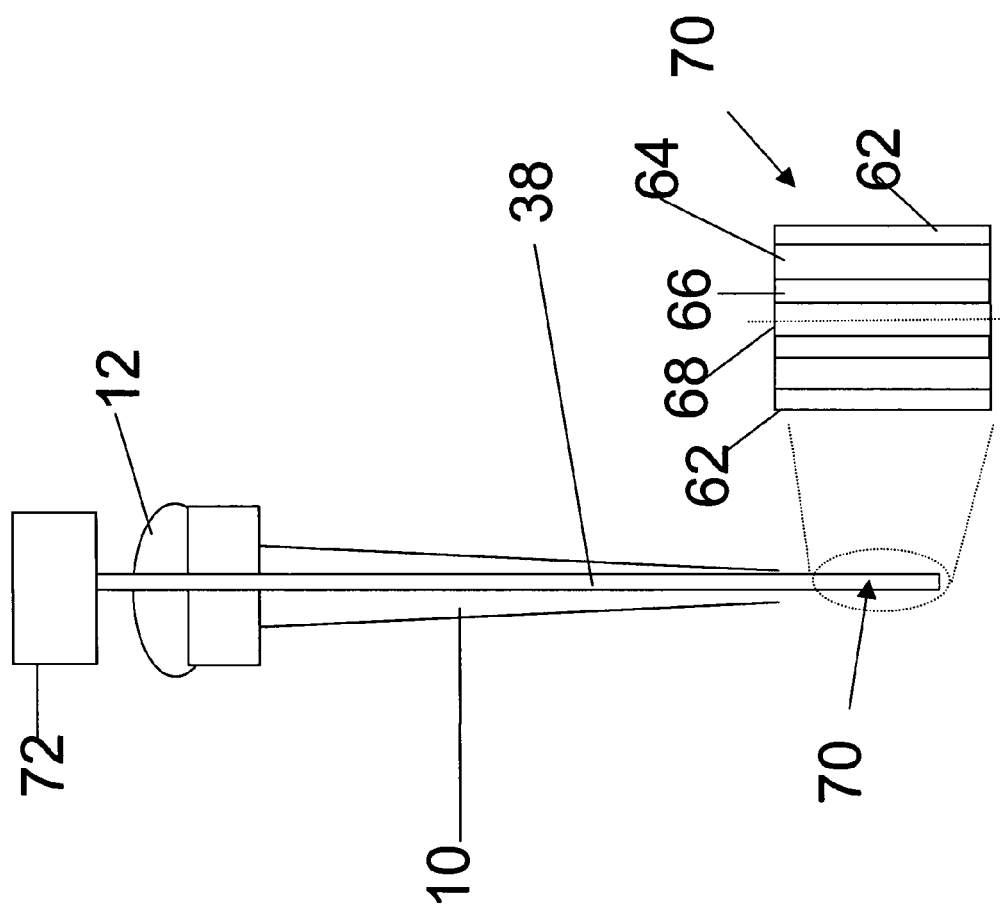
FIG. 8 illustrates a device according to an embodiment of the invention with hollow fibre with inner coated surface with catheter positioning device.

FIG. 8 shows the catheter with the hollow fiber 38 coated on the inside wall surface at the lower portion 70 of the fiber. The schematic cross sectional view shows the two layer coating 66 ad 64 on the inner fiber surface 62. The outer coating 66 is chosen to be biocompatible to eliminate absorption of proteins, while the inner coating 64 is the extraction phase facilitating removal of well defined components from sample introduced to the inner fiber via channel 68. The sample is drawn into the hollow fiber by using the device 72 generating pressure differential, such as syringe or metering pump connected to the hollow fiber. The action of drawing and ejecting sample produces agitation and therefore accelerate the extraction rate. The tubing is mounted in catheter, but can also be mounted in a positioning device illustrated in FIG. 7.

Figure 9:
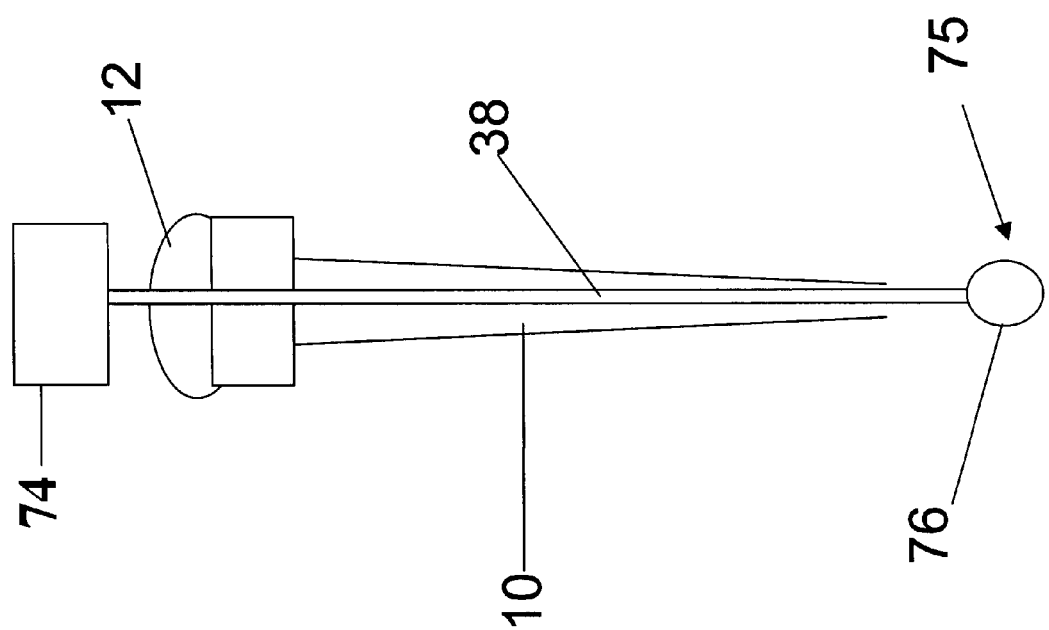
FIG. 9 illustrates a device according to an embodiment of the invention with hollow fibre sealed at one end with flexible extraction phase.

FIG. 9 shows the catheter with the hollow fiber 38 and stretchable coating sealing one end that can be blown out forming a small balloon structure 75 using the pressurized gas delivery device 74, such as small compressor or cylinder with carbon dioxide and micro-regulator connected to the free end of the hollow fiber. The material of the coating or its modified surface 76 can be designed to extract compounds from sample. The expended coating has higher surface area resulting in extraction rate enhancement. In addition repeated expansion and retraction of the coating cause induction of the convection currents and further increase in the extraction rate.

MINIATURIZATION

While the device described is quite small (127 μm diameter), further miniaturization would be beneficial, particularly for the study of single cells. As probe size is reduced, the effect of the size of the theoretical boundary layer around the extraction phase on the rate of extraction is diminished, as is the case with microelectrodes (Heinze, J. *Angew. Chem. Int. Ed. Engl.* 1993, 32, 1268-1288.). In practical terms, this means the degree of convection in the sample has less effect on the rate of extraction. This is important for sampling of any system where static extraction must be conducted, as it would in single cells, or where degree of agitation is variable as it is for intravenous sampling. In addition, the dimension of the extraction phase also impacts extraction equilibration. Thinner extraction phases equilibrate faster and are less dependent on sample convection. Devices with overall dimensions in the range of 1-10 μm would be suitable for monitoring the interior of single cells while devices in the sub-micron range would be useful for monitoring organelles within cells. There are currently no feasible means to accurately assess chemical concentrations occurring within cells. All currently available methods either require that the cell is killed (eg. cell lysis followed by CE of cytosolic components in microchannels), which may produce an erroneous result, or suffer from poor accuracy (fluorescence tagging of specific compounds). The main strength of the coated fiber technology is that it can monitor cellular process in a non-disruptive manner. Only a negligible portion of the chemical is removed, allowing cellular processes to continue unperturbed. Commercially available micropositioning devices using x-y-z stage coupled to microscope can be used to position coated end of the fiber in the well defined part of the investigated system.

Technology that has been developed for genetic manipulation of cells uses fine capillaries to sample and introduce genetic material in cells, controlled by micromanipulators and monitored by stereomicroscopes. Cells are maintained in isotonic environments during the manipulations, typically by being contained in dishes or vials filled with suitable buffers. Similar instruments could be employed for positioning and sampling cells with fiber probes.

PORTABLE AUTOMATED SAMPLING

Because the device and process described simplifies sampling and sample preparation significantly, it provides the opportunity for automated sampling of tissue concentrations without the need for continual human involvement. In on-line microdialysis sampling an animal being monitored is tethered to a stationary support and tubing conducting fluid to and from the microdialysis cannula and analytical instrument (CE or LC) is included in the tether. In the embodiment, an animal being monitored does not need to be tethered, but rather can carry a device for automatically moving probes in and out of a catheter, cannula or other sampling port at prescribed times. After sampling the device would hold the probes for retrieval and quantification at a later time. This embodiment would have similar advantages to the microdialysis system in terms of reduced human intervention and hence reduced sampling errors, with the additional advantage that animals in a study would be less restricted and stressed, and experiencing a more normal environment. This would reduce stress impacts on the integrity of the results.

STRATEGY OF SINGLE USE DEVICES

Up to now SPME devices have been designed to be re-used numerous times. While it is possible to re-use the polypyrrole coated fibre (wire) device described above, it is advantageous that this device be employed as a single-use device. Particularly in implementations where the device is exposed to blood, it would not be practical to clean the device and associated housing sufficiently for re-use. The goal of manufacture should be to minimize cost so that users find it cost-effective to dispose of the device after use.

COATING STRATEGIES

There are a number of additional coating strategies that would be desirable in the design of these devices, under certain circumstances. These would extend the usefulness of the devices for the purposes described and allow them to be applied for additional purposes.

Improved biocompatibility in the extraction phase would be beneficial to extend either the time period the phase can be in contact with tissues, or increase the number of samplings that can be made from one site. This can be achieved in two different ways. Either new phase with better biocompatibility could be selected or a biocompatible outer layer could be used in conjunction with an inner extraction phase having lower biocompatibility.

Polypyrrole itself has good biocompatibility. It has been used for several years in biosensor devices without any evidence of toxicity, immunogenesis (initiation of an immune response) or thrombogenesis (initiation of clotting response). It is an example of an extraction phase that is suitable for exposing directly to the investigated system. If it is desirable to use a less biocompatible extraction phase the device could be rendered biocompatible by coating the extraction phase with an outer biocompatible layer such as derivatized cellulose, poly(ethylene glycol), poly(hydroxyethyl methacrylate), poly(acrylamide), poly(N, N-dimethyl acrylamide), dextran, poly(urethane), and poly(acrylonitrile). Analytes of interest would diffuse freely through this outer layer and be extracted by the extraction phase on the inner layer. This may be useful if more traditional extraction phases such as poly(dimethylsiloxane), polyacrylate, poly (divinyl benzene) or ion exchangers are of interest for extractions.

Biorecognition entities that either comprise the extraction phase or are immobilized in another phase having low extraction affinity could provide both higher selectivity and higher sensitivity in these analyses. Higher affinity would provide higher sensitivity and more easily allow for shorter probe residence times. Higher selectivity would allow for reduced disturbance of the system under study, further enhancement of sensitivity and reduced concern for competition in extraction. This would permit the quantitative analysis of one compound present at low concentration when a competing compound is present at high concentration.

Biorecognition in the extraction phase may be accomplished by entrapment of antibodies or other molecules capable of biorecognition in an inert biocompatible extraction phase. This is demonstrated by the use of polypyrrole to entrap antibodies specific for diazepam.

Figure 10:
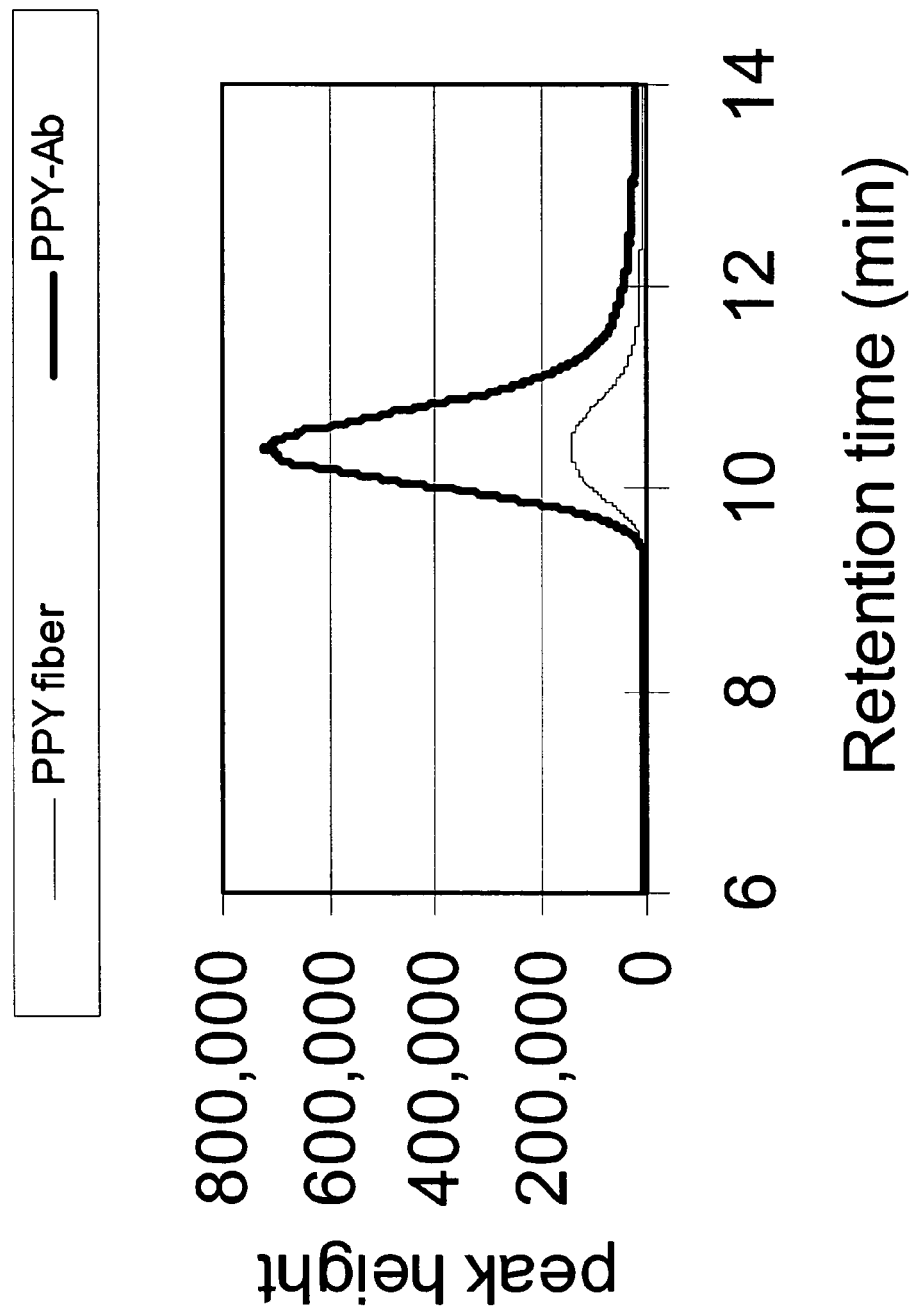
FIG. 10 shows a chromatogram comparing diazepam extraction from fibre with polypyrrole only versus fibre with anti-diazepam antibody entrapped in polypyrrole.

FIG. 10 shows a chromatogram comparing extraction of a sample containing diazepam, with a device with polypyrrole only, versus a device with entrapped anti-diazepam antibody. In this case the analyte affinity to the antibody is much higher than it is to the polypyrrole. Alternatively, antibodies, nucleic acids or other molecules may be covalently attached to the fiber using typical immobilization strategies or they may be electrostatically immobilized by means similar to the immobilization of nucleic acids to nitrocellulose used in current blotting technologies. For covalent immobilization either random or oriented strategies may be used in one application or another.

Figure 11:
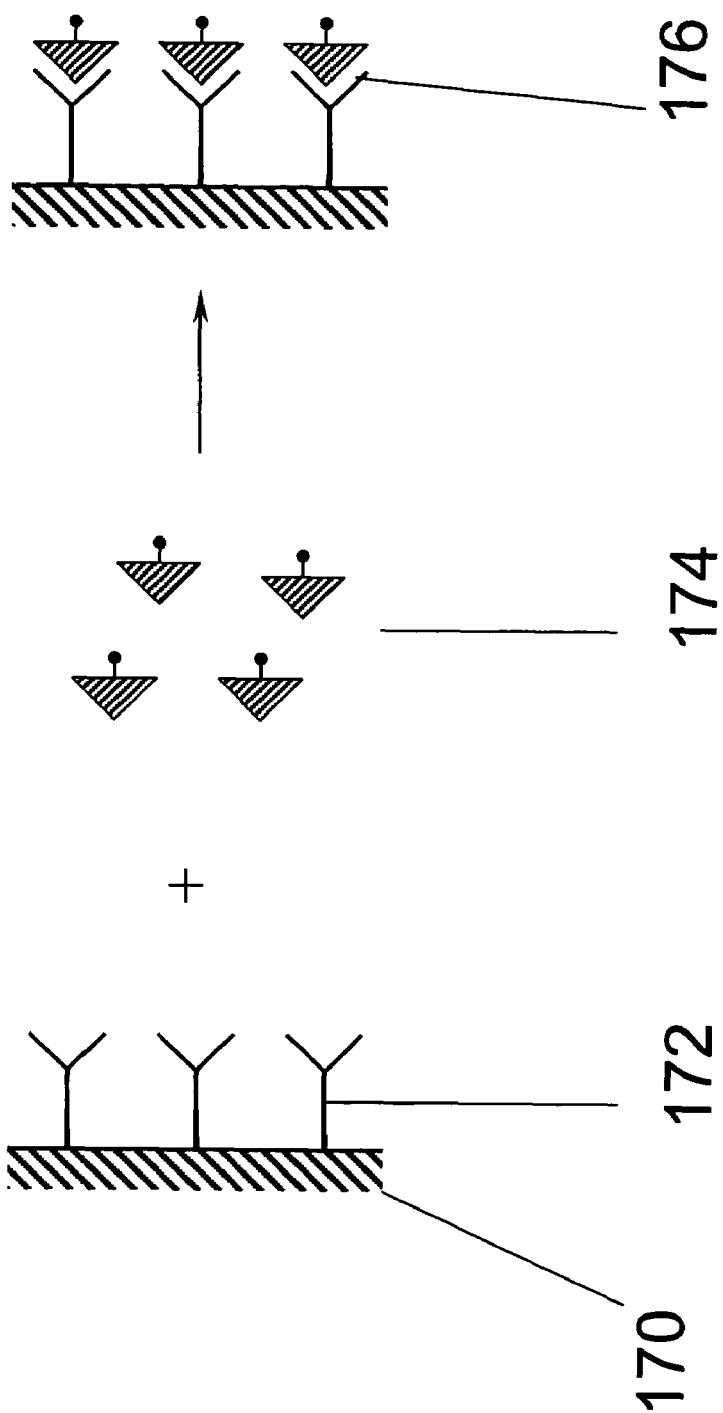
FIG. 11 illustrates selective extraction of diazepam using anti-diazepam antibodies immobilized on surface.

FIG. 11 shows a schematic of the oriented immobilization of antibody 172 on a surface 170, and attraction of antigen 174, to form an antibody-antigen complex 176. The diazepam may be liberated from the complex for quantification by temporary or permanent denaturation of the antibody protein.

If a probe with very high selectivity was developed, it could potentially extract only the compound of interest, which would eliminate the need for chromatography in the analysis. Direct introduction to a mass spectrometer for quantification would further simplify the analytical process. Such entities may include antibodies or antibody fragments, enzymes, receptors, proteins, protein subunits or peptide sequences, DNA, RNA or polynucleotides, or the antigens or substrates that bind with any of these. Such biorecognition entities may be immobilized by adsorption, electrostatically, covalently or by entrapment within another matrix. Covalent immobilization may be by either random or oriented means.

Biorecognition may also be achieved by using molecularly imprinted polymers. In this case a polymer is prepared in the presence of the analyte of interest. The polymer contains functional groups that interact electrostatically with the analyte. After polymerization, the analyte is removed and cavities remain in the polymer, with appropriate functional groups located inside. When used for extraction, analyte freely soluble in the sample is attracted to the cavities and held there by electrostatic forces. These polymers are seen by some as synthetic antibodies due to their high selectivity for the analyte of interest. Such polymers provide enhanced selectivity when used as extraction phases in devices according to the invention.

It is also possible to prepare a coating that can have its extraction efficiency gated or activated just prior to extraction. This would allow for the pre-positioning of the device in a specific site, and then activate the extraction phase just as extraction is to start. Because polypyrrole is a conducting polymer, this may be accomplished by applying a small charge to the fiber. This is useful for the extraction of ionic compounds through controlling of the oxidation state of the polymer. Alternatively this may be accomplished using the device shown in FIG. 8 for soft tissue sampling. The device could first be positioned in the desired location, but the exposure of the fiber to the tissue could be delayed until the proper time to initiate sampling.

USE OF INDICATOR COMPOUND

A common and valuable tool in bioanalytical analysis is the monitoring of the appearance or disappearance of an indicator compound that is specific for a biochemical pathway. This is used for instance to monitor for the presence of specific cells or bacteria, or for the presence of free enzymes. In the typical chemical reaction a substrate (S) is transformed into a product (P) by interacting with a single enzyme or an enzyme system with associated cofactors. Enzymes may or may not be transformed in this process. The indicator may be the substrate, in which case its disappearance is monitored, or it may be the product, in which case its appearance is monitored. The amount of indicator formed in a specific time is correlated to both the amount and activity of the target enzyme present. If the indicator has an affinity for the extraction phase, enzyme activities and/or metabolic rates may be monitored in situ. The substrate may be either loaded onto the fibre or placed into a cell suspension or enzyme solution. When the fibre is placed into the solution, indicator will become immobilized in the fibre, and can be subsequently quantified by an analytical instrument.

Pre-Loading of Fibre with Calibrant

For conventional SPME analysis, a common difficulty is in devising accurate means of quantification. For in vitro analysis quantification is often achieved by adding a known amount of standard to the sample, and then performing the analysis. This is referred to as calibration by internal standard or standard addition. The amount of the standard recovered is assumed to be correlated with the amount of unknown analyte recovered and the ratio is calculated in order to determine the original concentration of unknown. For in vivo and in situ analysis it is typically not practical to add a standard to the system under analysis. Until now the most practical means of calibration is by preparing a series of synthetic standards that match the sample as closely as possible, and comparing the results from the standards analysis with that of the unknown. This approach was described above for the calibration of polypyrrole devices in the in vivo pharmacokinetic study with reference to FIG. 12. In this case whole dog blood was obtained from a commercial supplier and samples were prepared with various drug concentrations. Upon analysis a calibration curve is constructed and this curve is used to interpolate unknown detector responses to estimate unknown drug concentrations. While the method is conceptually simple, it is not always highly accurate as it cannot accommodate the impact of slight changes in the in vivo site for impact on the results.

As an alternative to conventional internal standard calibration, a standard may be loaded onto the fiber (extraction phase) prior to analysis and the loss of standard from the fiber is monitored instrumentally. Where the kinetics of absorption of the internal standard analyte to the fiber is equivalent to the kinetics of desorption (binding is reversible), absorption and desorption are controlled by diffusion in the sample and the rate of loss of standard from the fiber will be correlated with uptake of analyte by the fiber. The amount of analyte lost may be correlated with the amount absorbed, and consequently with sample concentration of unknown also. Using this strategy variation in sample convection may be controlled for by referencing unknown analyte to the amount of calibrant lost from the fiber. This approach is discussed in more details below. Alternatively, where the convection conditions and hence rate of mass transfer and are known or controlled, the use of an irreversibly bound calibrant on the fiber may be used. The fiber would first be exposed to a matrix-matched standard with a known concentration of analyte. The fiber would subsequently be exposed to the unknown sample. The ratio of unknown to standard extracted by the fiber would accurately reflect the ratio of unknown to standard sample concentrations. (G. Xiong, Y. Chen and J. Pawliszyn "On-site calibration method based on stepwise solid-phase microextraction", *J. Chromatogr.* in press).

Pre-loading of compound onto the fiber may also be used for calibrated delivery of compound to a precise tissue region. Where the compound pre-loaded has low to moderate affinity for the fiber, compound will partition out of the fiber and into the surrounding tissue during exposure. This may be used as a means of dosing only one targeted tissue region with a drug or other compound of interest, avoiding dosing of the whole animal as is commonly the case in therapeutic drug regimens. Tissue dosage control may be attained by precisely controlling the exposure time. Dosage may then be confirmed by desorbing remaining analytes into an analytical instrument to quantify the amount remaining, allowing the calculation of the amount delivered.

An exemplary use of calibrant is discussed below with reference to Example 4.

Standards in the Extraction Phase.

Internal standard and standard addition are important calibration approaches, which are very effective even when quantifying target analytes in complex matrices. They compensate for additional capacity or activity of such a matrix. However such approaches require delivery of the standard to the matrix. This adds additional steps to the sample preparation, which makes the process longer and is sometimes prohibitive, for example in the case of on-site or in-vivo determinations.

According to an aspect of the invention, an alternative approach may be used where the standard is delivered together with the introduction of the extraction phase. This approach is not practical to implement for exhaustive extraction techniques, since large volumes of the extraction phase having a high affinity for the target analytes are used in these approaches to facilitate as complete removal of the analytes from the matrix as possible. However, in microextraction a substantial portion of the analytes is present in the matrix during the extraction and after equilibrium is reached. This presents an opportunity to add the standard to the investigated system together with the extraction phase. For example, when performing small volume (a few mL) sample analysis involving microextraction step, as is frequently the case with automated analysis, placing the extraction phase/ standard mixture in the vial with the sample can be combined with addition of a standard. In this way, the step of spiking the sample with a standard is eliminated.

Desorption and re-equilibration of a standard originally present in the matrix can occur simultaneously with the mass transfer and equilibration of the target analytes from the matrix to the extraction phase. Thus, the standard delivery process according to this aspect of the invention does not add substantially to the extraction time. For example, in automated fiber SPME analysis the standard can be introduced onto the coating during an automated analysis process by exposing the fiber to a vial containing the standard. Alternatively, multiple fibers containing standards can be used each for single analysis. In addition, the standard can be generated in or released from the coating by way of a chemical reaction in the coating.

A significant impact of the standard in the extraction phase approach for calibration would be realized for on-site, in-situ or in-vivo investigations. However, it is desirable to minimize the amount of foreign substances added to the investigated system. For this reason, direct standard spike into the matrix is typically not possible. Full re-equilibration of standards present on the fiber is frequently not feasible because of the potential for contamination and large dilution which could occur in on-site investigations. However, successful calibration can be accomplished by investigating kinetics of the desorbtion/sorption process. Since the rate of extraction for most practical types of extractions is controlled by mass transfer through the boundary layer, the desorbtion rate or the standard can be used as an indication of the extent of the boundary layer (existing either in the matrix or in the extraction phase, or both). This information can be used for calibration of the target analytes.

In an advanced approach, standards can be added to balance the analyte loss from the matrix during extraction, similar to methods which may be used in dialysis, in order to minimize the impact of standards on the investigated system. This objective may be accomplished by adding the same amount of the standard as the amount of analyte being removed from the matrix. The standard chosen may be an isotopically labeled analog of the target analyte, in order to minimize impact on the investigated system. In addition, this approach can allow study of the physicochemical partitioning and adsorption phenomenon among sample matrix components.

When employing a standard in the extraction phase, calibration can be accomplished in any microextraction or steady state approach including Solid Phase Microextraction (SPME), micro liquid phase extraction (MLPE), and membrane extraction or headspace extraction. In SPME, a standard can be used to dope the solid/polymeric extraction phase. In MLPE, a standard would be present in the liquid extraction phase. In membrane extraction, the standard would be present in the striping phase and in headspace extraction in the gaseous headspace. In some cases the standard can be delivered by other components of the extraction system. For example, in the fiber SPME the standard can be delivered from a needle by first sorbing the standard onto the needle material. Also the standard could be delivered together with the vial, for example by including the standard on or in the wall of the vial.

USE OF MULTIPLE FIBRES

The development of multiple fiber coating strategies has several benefits. In addition to providing more flexibility in selecting devices for a particular application, multiple devices could be used in parallel to provide for a more complete profiling of the types and amounts of compounds present in a sample. This may be accomplished either by exposing multiple fibres to a sample in parallel, or by preparing one fiber with multiple sorbents.

FIBRES FOR CONDUCTING MICRO-CHEMICAL REACTIONS

On-fibre reaction can significantly enhance the detection of components of interests. For example on-fibre fluorescence labeling has been has improved detection limits for detection of toxins at trace level (A. Namera, A. So, J. Pawliszyn "Analysis of Anatoxin-a in Aqueous Samples by Solid-Phase Microextraction Coupled to High-Performance Liquid Chromatography with Fluorescence Detection and On-Fiber Derivatization" *J. Chromatogr.* 963, 295-302 (2002)). Two of the most important chemical reactions for molecular characterization in genomics and proteomics research are DNA amplification and enzymatic protein digestion. Both processes are enzymatic reactions that are conducted in vitro, with the products either being carried on to a further processing step or analysed directly.

In DNA amplification a small number of DNA or polynucleotide fragments are amplified by the enzyme DNA polymerase. Through the action of the enzyme and suitable substrates, the copy number of DNA fragments can be increased exponentially in just a few hours. The process is characterized by high fidelity so that the end product is a very pure solution of identical DNA fragments. Typically the amount of DNA originally present is insufficient for further processing and/or analytical characterization whereas the concentration in the final product is sufficient. The product may either be characterized for nucleotide content and sequence or used for the preparation of peptides or proteins coded by the DNA sequence.

For enzymatic protein digestion a protein sample is digested by enzymes that cleave the polypeptide chains at specific sites. The resulting polypeptide fragments may be characterized for molecular weight or peptide content and sequence. Typically the intact protein is too large for direct characterization and so a protein is characterized by a 'fingerprint' analysis of the pattern of polypeptide fragments produced by one or more enzymatic cleavage. Alternatively the polypeptides may be sequenced and the sequence of the original protein reconstructed. This allows for example, that the DNA sequence coding for the protein may be determined either for the purpose of identifying its location in the genome or for development of an expression system to produce the protein in quantity.

With the continued miniaturization of genomic and proteomic analyses through the use of micromachined or µTAS devices, there is a need to miniaturize the sample preparation and introduction steps that come up front. These types of miniaturized analyses are increasingly important in the fields of genomics and proteomics where sample sizes are small due to the high cost of these samples. Also the miniaturization allows for parallelization and higher throughput in analysis to more efficiently process the very large number of samples made possible by the completion of the human genome project. A porous polymer attached to a fine fiber or wire makes an ideal medium in which to conduct these enzymatic reactions in miniature scale, with the added advantage that when the reaction is complete, the device is also suitable for introduction of the reaction products directly to a microanalytical system.

INTERFACES

As described above one of the strengths of the device and process described is that once sampling and sample preparation (pre-concentration and elimination of matrix) have been completed, the device of the instant invention is ideally suited for directly introducing the extracted analytes to an instrument for separation and quantification.

Conventional SPME devices are interfaced to GC or LC equipment for quantification of amount of compound extracted. In the case of GC equipment the fiber is exposed in the heated injection sleeve similarly to the way a conventional syringe injection is conducted. Analytes for GC analysis are necessarily volatile at the temperatures normally used in a GC injector and are efficiently desorbed in the hot carrier gas flowing through the injection sleeve and into the separation column. Compounds analysed by LC are typically non volatile and/or thermally unstable and so heat cannot be used for desorption. For LC desorption, a dedicated interface is required to first remove analytes from the fiber and transfer them to a solvent. A portion or all of this solvent is then injected into the instrument for analysis. In the commercial interface, the fiber is desorbed in a solvent filled chamber in a valve connected to the instrument inlet. After desorption, the valve is switched in line with the pressurized solvent flow of the instrument and the entire volume of the desorption solution with dissolved analytes is introduced to the instrument.

MODIFICATION FOR EFFICIENT LC QUANTIFICATION

Figure 13:
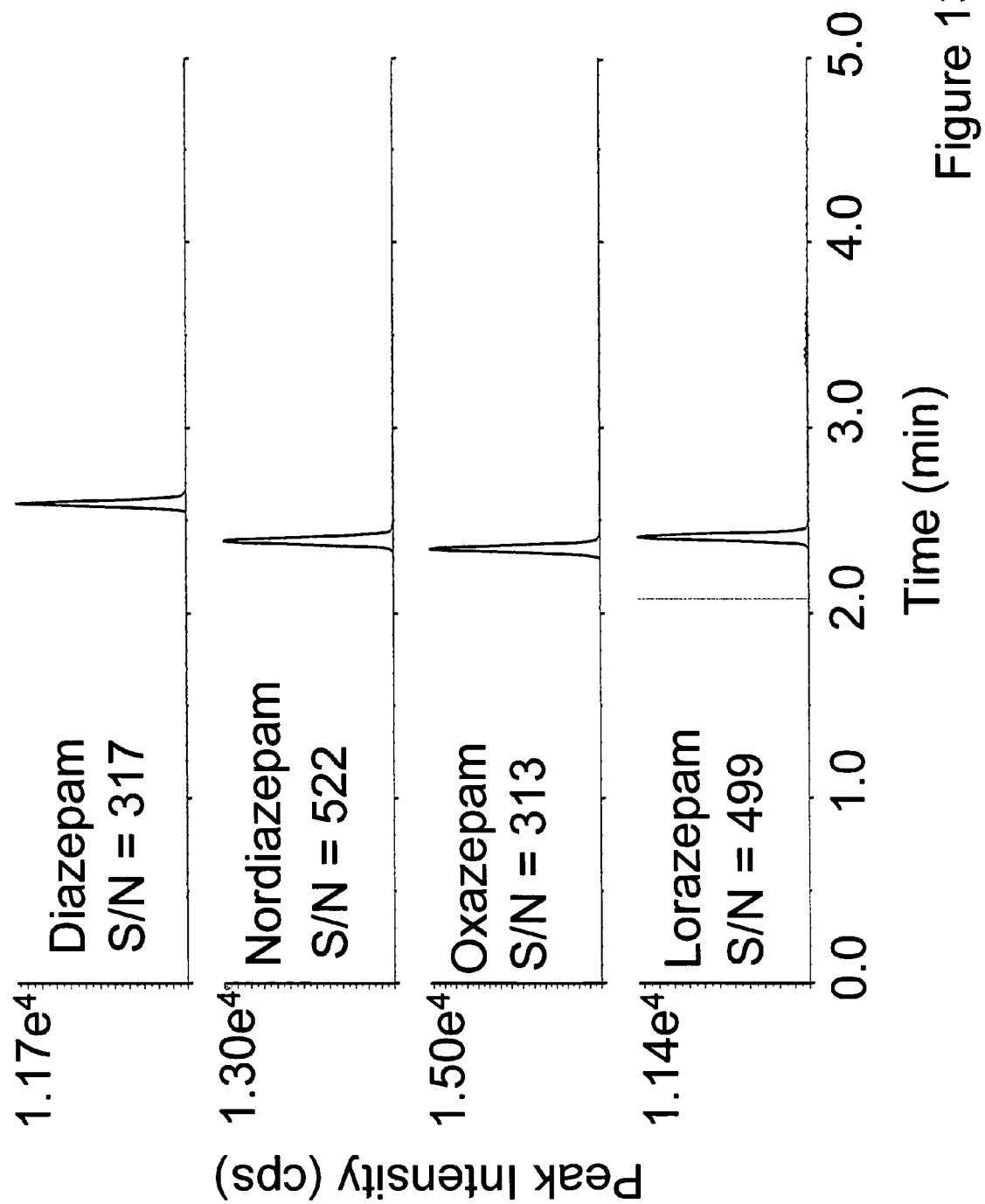
FIG. 13 illustrates an example chromatograph obtained after LC/MS/MS quantification of device extraction from plasma.

The technique has been limited by the relatively large volume of the commercial desorption interface (100 µL). Because of the phase thickness of the commercial SPME devices for LC (ca. 50 µm) this large volume is required. If desorption volume is reduced a significant proportion of the analytes are not removed from the fiber. Carryovers in the range of 20% are common (depending on the specific analyte and desorption solvent used) as the volume of desorption solvent is reduced below 50 µL. These volumes, however, are too large for typical LC applications as injection volumes are in the 10-20 µL range, particularly for LC/MS applications. Large injection volumes in these analyses typically produce unacceptably broad chromatographic peaks and poor resolution. When only a small portion of the total desorption solvent is injected, inferior sensitivity results. One strength of the device of the instant invention is the ability to introduce all of the extracted analyte to the instrument for quantification. This allows for maximal sensitivity. Fibres with significantly reduced phase thicknesses, such as the polypyrrole coated wire described for the pharmacokinetic analyses, may be efficiently desorbed in 10-20 µL of desorption solvent. The entire desorption volume may then be injected for quantification. The result is sharp, symmetrical peaks as are shown in FIG. 13, which may be accurately integrated and produce good chromatographic resolution.

The foregoing described the use of static desorption, but dynamic desorption of analytes is also of interest in certain applications. This is achieved by passing desorption solvent over the fiber during desorption. Because the fiber is continuously exposed to fresh desorption solvent, quantitative desorption is theoretically possible. The rate of desorption is governed by the rate of solvent flow over the fiber. Faster flow results in faster desorption. To achieve the fastest desorption possible and to avoid ending up with an overly large solvent injection plug, it is necessary that the inner diameter of the desorption chamber is as small as possible. When volumetric flow is constant, faster linear flow is achieved in a smaller diameter chamber. This results in a shorter desorption time and hence a minimized total desorption volume.

AUTOMATION OF LC QUANTIFICATION

While the reduced volume HPLC interface used to date allows for efficient transfer of analytes from the fiber to the instrument, the process is only partially automated. To date the introduction and removal of the probe wire to/from the interface must be performed manually for each injection.

Figure 14:
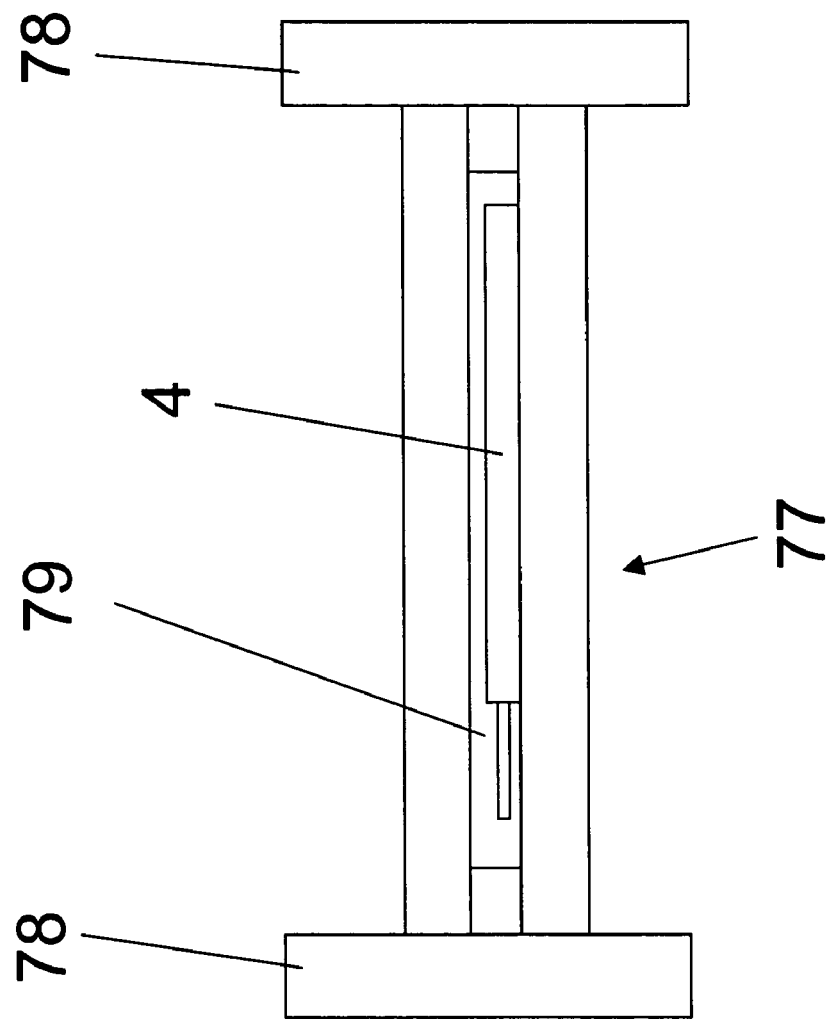
FIG. 14 shows a cartridge holding a fibre.

FIG. 14 illustrates a micro-cartridge 77, which contains coated piece of fiber in its small cavity 79 and sealed with plugs 78. The cavity 79 can be filled with desorption solvent. After extraction the coated piece of fiber containing the coating 4 is placed in a cavity 79 of the cartridge 77 for protection during storage and transport. Determination of extracted components can be performed in an automated instrument adopted for use with cartridges.

INTERFACE FOR CE, USE OF ELECTROKINETIC STACKING

As discussed above, the device of the instant invention provides an ideal means for interfacing sampling and sample preparation to microanalytical instruments, particularly when devices much smaller than the commercially available SPME devices are employed. In capillary electrophoresis and related technologies, analytes are separated in a capillary typically 50 µm in diameter. This is too small for conventional syringe injection. Injection is typically by hydrodynamic or electrokinetic means. With hydrodynamic injection a sample is placed in the buffer reservoir associated with one end of the capillary. That end is then lifted above the opposite end by a prescribed amount for a prescribed time. The volume of sample entering the capillary may be calculated from the time, the elevation difference, the capillary diameter and the solution viscosity. The sample solution is then exchanged for running buffer solution prior to applying the separation voltage. While simple, the technique suffers from inaccuracies in injection volume and poor reproducibility from one analysis to the next. With electrokinetic injection a sample is again placed in the buffer reservoir associated with one end of the capillary. An injection voltage is applied across the reservoir and capillary and analytes in solution move into the capillary by electromotive force. Once sufficient material has been injected the voltage is removed and the sample solution is again exchanged for running buffer solution prior to applying the separation voltage. This method suffers from inaccuracy in injections due to the variation in electrophoretic mobility between analytes. This results in different amounts of the different compounds present being injected. A small diameter fiber with extracted analytes may be introduced directly inside a CE separation capillary filled with running buffer (Whang, C. W., Pawliszyn, J. Anal. Commun., 1998, 35, 353-356). This allows for accurate, quantitative introduction of analytes for separation.

As an improvement to this technique for CE analysis, by carefully matching the outer diameter of the fiber and the inner diameter of the separation capillary, a stacking of analytes occurs prior to separation results. This allows for much superior resolution. Electrophoretic velocity is inversely proportional to the cross-sectional area inside the separation capillary. When this area is reduced, increased velocity results because of an increase in electric field gradient. When a fiber is introduced inside a CE capillary, the space between the fiber and the capillary wall has a much smaller cross-sectional area than the space after the fiber where only buffer is present in the capillary. When a fiber is present and separation voltage applied, the analytes move out of the fiber and along the restricted channel quite quickly. When they reach the area of open capillary mobility drops significantly and the analytes are concentrated in a narrow band. During separation a higher resolution is achieved than would otherwise be possible.

Figure 15:
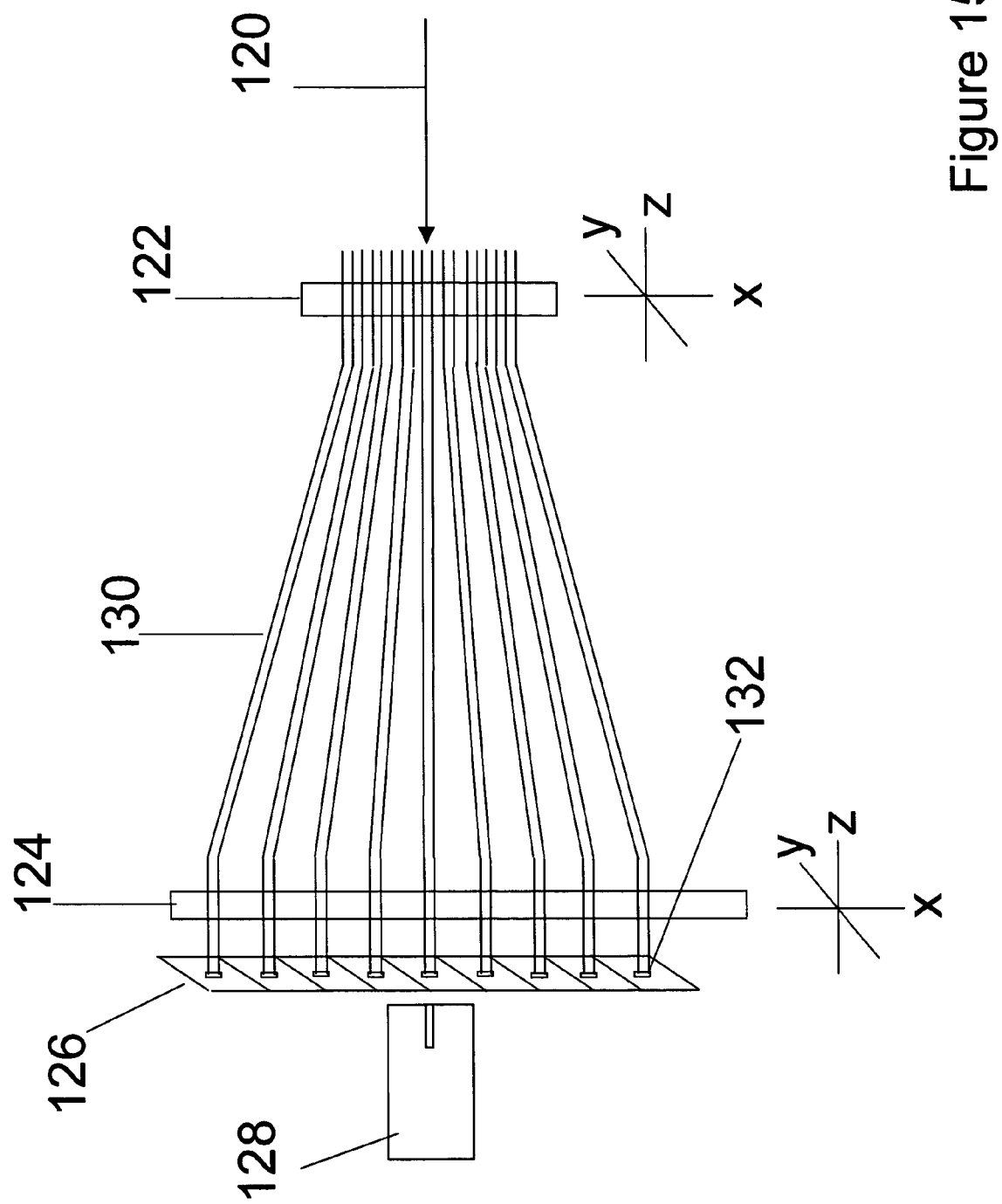
FIG. 15 is a schematic of batch process for parallel extraction and multiple MALDI desorption with positioning devices at both laser source and desorption ends of fibres.

FIG. 15 illustrates x-y-z positioning device for use with a fiber bundle. Individual fibres may be positioned precisely in the separation capillary prior to desorption. In this case the extraction phase would be coated on more than just the very tip (132) of the fiber, as is shown in FIG. 15, and desorption would be accomplished by applying an appropriate electric potential rather than by laser pulsing.

DIRECT INTRODUCTION TO MS THROUGH NANOSPRAY NEBULIZER

In some instances it is not necessary to chromatographically separate extracted analytes prior to quantification. This is the case where the fiber has very high selectivity such that only the analyte of interest is extracted with no interfering substances. It is also true where mass spectrometry is used for detection/quantification and components are separated by mass rather than by time prior to quantification. For MS applications it is possible to place the fiber directly into a nebulizer needle in an electrospray ionization source.

Figure 16:
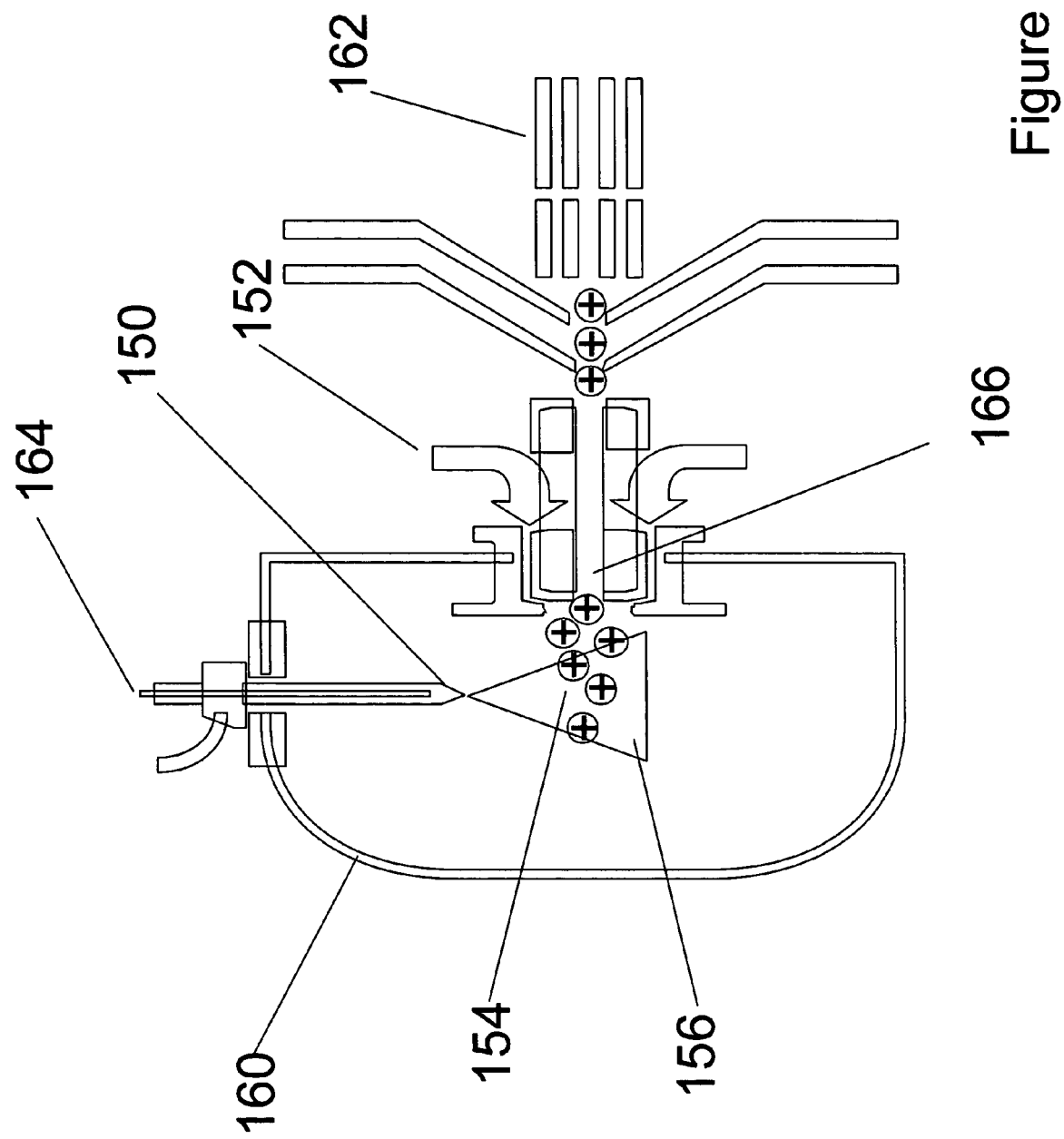
FIG. 16 is a schematic of the inventive device used with nanospray nebulizer and ESI MS.

FIG. 16 describes this process schematically. Solvent flowing through the nebulizer 150 efficiently desorbs analytes from the fiber 164 prior to being nebulized and sprayed in a plume 156 in a mass spectrometer atmospheric pressure ionization source 160. Ionization is then accomplished by standard ESI with MS detection, ie. droplets in the plume 156 are dried and reduced in size by hot gas flow 152 until ions 154 form in the vicinity of the orifice 166. These then pass into the mass analyzer 162 in the instrument.

APPLICATION TO MALDI ANALYSIS

Matrix-assisted laser desorption/ionization (MALDI) is a technique for ionization of molecules using a laser as the energy source. As a very soft ionization method, MALDI yields primarily singly charged protonated molecules which are then conveniently quantified by either ion mobility spectrometry or time of flight mass spectrometry. This feature has made MALDI a widespread ionization tool for high molecular weight, nonvolatile and thermally labile analytes. MALDI has enabled the routine determination of large bimolecular such as peptides and proteins (P E. Jackson, P F. Scholl, and J D. Groopman, *Molecular Medicine Today*, 2000, 6, 271.)

The embodiment of the invention wherein the inventive fiber device is coupled to MALDI advantageously allows a combination of sample extraction with the ionization procedure on the very tip of a fused silica optical fiber for bimolecular analysis. The sample end of the fiber was coated for the extraction of peptides and/or proteins in a matrix solution. In the case of enkephalin and substance P the matrix used was alpha-cyano-4-hydroxy cinnaminic acid. The optical fiber thus served as the sample extraction surface, the support for the sample plus matrix, and the optical pipe to transfer the laser energy from the laser to the sample. Laser energy was transferred through the other end of the optic fiber to ionize and desorb the biomolecules for subsequent analysis. This fiber/MALDI combination was coupled with an ion mobility spectrometer and a tandem quadrupole/time-of-flight mass spectrometer (in separate experiments) for the detection of the MALDI signal.

Figure 17:
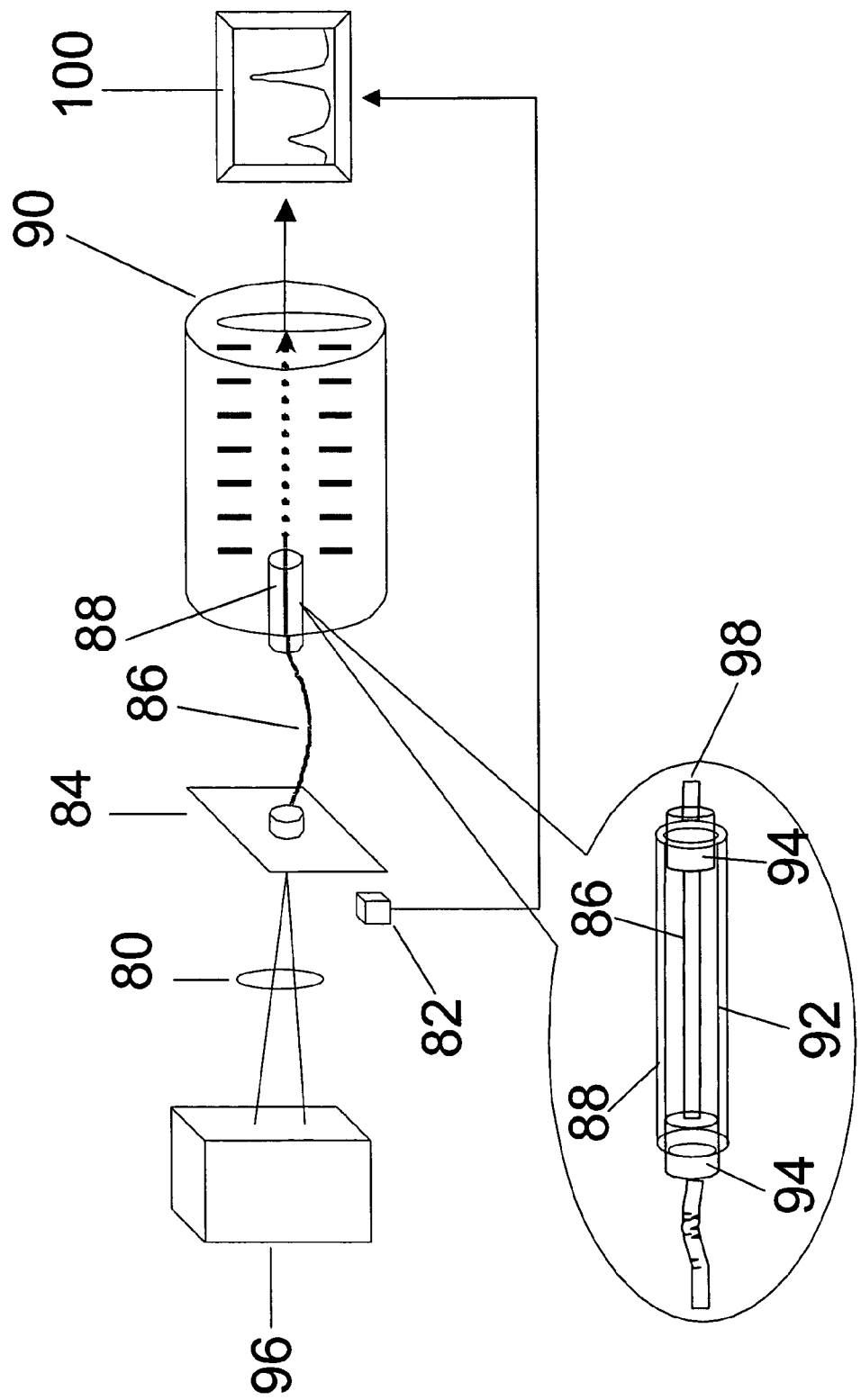
FIG. 17 shows a schematic of fibre/MALDI-IMS system according to the invention.

FIG. 17 shows a schematic of the fiber/MALDI-IMS interface and instrument. This consists of a laser source 96 and focusing lens 80, which focuses the laser light onto the uncoated end of the fiber, held in an x-y-z positioning array 84. The array movement may be manual or automated. The fiber 86 transmits light from the source to the x-y-z positionable inlet 88 of the mass analyzer 90, which in this case was an ion mobility spectrometer. In the inlet 88 the coated end of the fiber 86 is held in place by two silicone septa 94 and a section of support tubing 92. Only the very tip 98 of the fiber is coated with extraction phase. A photosensitive diode 82 is positioned at the laser source 84 to sense the desorption laser pulse and initiate data collection 100.

Figure 18:
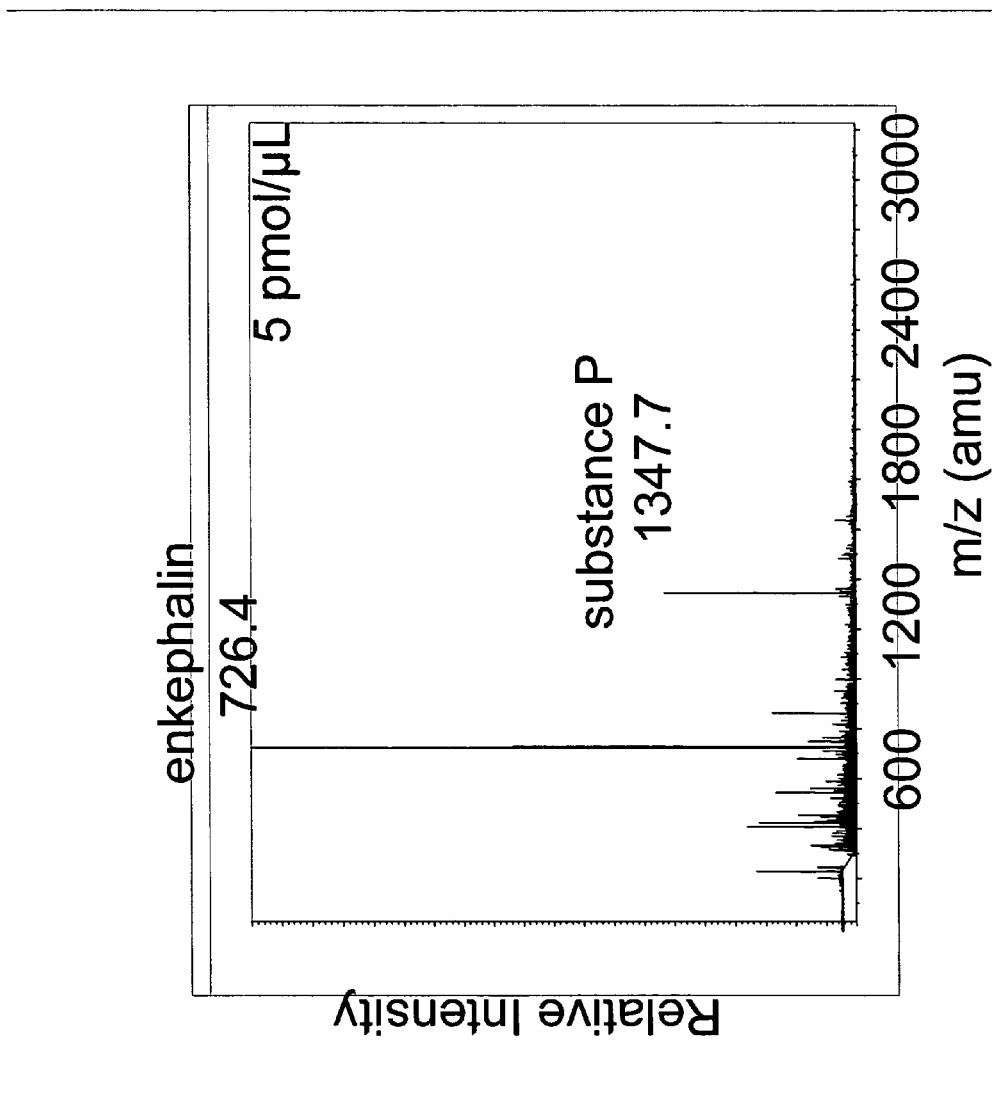
FIG. 18 illustrates an exemplary mass spectrum obtained from a fibre/MALDI-TOF MS system according to the invention

FIG. 18 shows the ion mobility mass spectrum of enkephalin and substance P were obtained using this system.

One advantage of the MALDI/IMS interface is that the MALDI source is operated at ambient pressure instead of high vacuum, as it is in conventional MALDI/TOF mass spectrometry. Also, loss of sample delivered to the drift tube is negligible at ambient pressure and it has been reported recently that atmospheric pressure MALDI produces a generally uniform ion cloud at atmospheric pressure. The ionization process is even softer than that of the conventional high vacuum MALDI and is capable of producing protonated molecular ions for small proteins. This is convenient for the MALDI analysis of macromolecules because of the relative absence of metastable fragmentation and discrimination in the ionization process compared to conventional vacuum MALDI. The most promising advantage of this ambient interface is the possibility of interchangeably using the same instrument for both electrospray and MALDI sample introduction.

Figure 19:
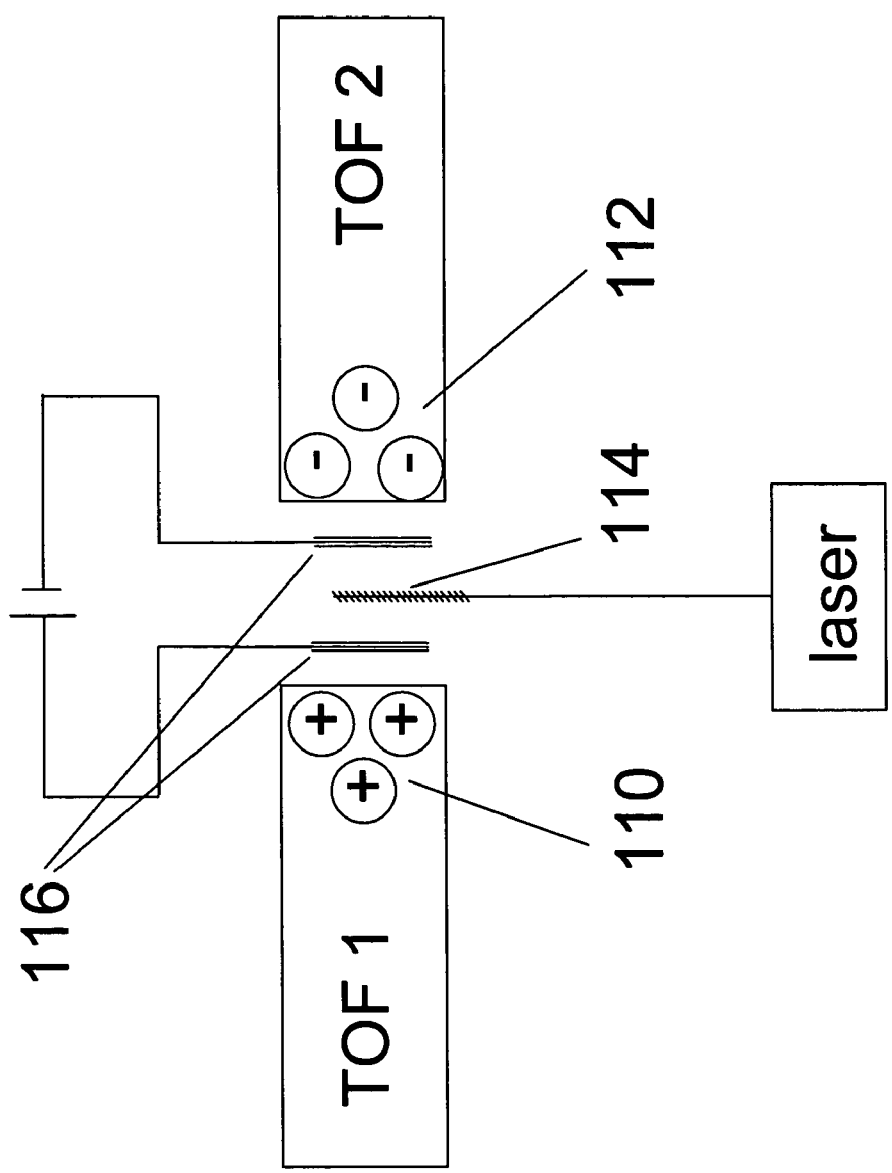
FIG. 19 is a schematic of a fibre/MALDI source.

FIG. 19 shows a schematic of the laser desorption interface and ion formation. In this case two time of flight mass spectrometers (TOF) are used, one to sample positive ions 110 and the other to sample negative ions 112. A laser pulse initiates desorption from the extraction phase 114 and polarized plates 116 accelerate the appropriate ions into the appropriate mass analyzer.

Though MALDI has enabled the routine determination of large bimolecules such as peptides and proteins, it has always been great interest to develop quantitative MALDI analysis. For quantitative work with conventional MALDI analysis, the laser beam is scanned cross the sample area on the target plate, and each sample spot is irradiated with multiple laser shots until a striking decrease in signal detection is observed which indicates the removal of most of the sample loaded on this particular spot. Therefore, tens to hundreds of laser shots must be fired to finish the scanning process, and the final spectrum is typically a sum or an average of all the spectra obtained from each laser shot. This sampling process will lead to the unavoidable poor shot-to-shot and spot-to-spot sample reproducibility, and has been considered as the fundamental limitation for method quantification in MALDI analysis.

The combination of the inventive device with MALDI has technically solved the above problem as it combines sample extraction with the ionization procedure on the tip of a fused silica optical fiber. The optical fiber thus served as the sample extraction surface, the support for the sample plus matrix, and the optical pipe to transfer the laser energy from the laser to the sample. Since the sample was loaded directly on the fiber tip, so the sample size was identical to that of the laser irradiance area and there existed no spot-to-spot desorption difference. In addition, due to the multiple reflections inside the fiber, the primary laser profile is converted into a homogeneous intensity profile at the sample end fiber surface. This means that laser emission is homogeneous through the fiber tip surface. The method was developed as to accomplish all sample desorption that was extracted on fiber tip with a single laser shot. As long as this situation could be satisfied, the spot-to-spot and shot-to-shot spectral disparity would also be minimized. In this way it dramatically improved the quantification aspect of MALDI as well as saved large amount of analytical time and analyte consumed. To explore the quantitative aspects of the fibre/MALDI method TOAB was selected as the analyte compound and all experiments were performed in the matrix DHB. The fibre/MALDI-IMS system described in FIG. 17 was used for quantification.

In the extraction step of the previous experiments, the tip of the fibre/MALDI fiber was dipped into the solution containing both sample and matrix. For this pre-mixed extraction method, the analyte to matrix ratio was pre-optimized and fixed for the best performance and this is almost impossible for the detection of analyte in real samples of unknown concentrations. Meanwhile, due to the very small capacity of the extraction phase, there exists a competition between the analyte and matrix that causes a further limitation for the amount of analyte that can be extracted. A more practical way is to load the matrix in a second step after sample extraction. Spray method with a nebulizer is an ideal candidate for this purpose as it forms very fine solution drops smaller than 100 nm. After sample extraction, matrix solution is loaded with a nebulizer. The fog like matrix drops would help to form more uniform cocrystalline on the fiber tip surface. The amount of matrix loaded on the fiber or matrix to analyte ratio could be easily adjusted by varying the concentration of the matrix solution and the spray time.

Example 2 describes use of a MALDI/IMS interface which is associated with reduced noise. Reduced noise, though convenient, is not necessary. Thus, careful alignment of the laser with the sample surface is optional, as the fiber itself can accomplish this. As an alternative however, it would still be feasible to conduct a conventional MALDI analysis where the laser is directed at the surface of the fiber. This would allow devices to be constructed from non-light conducting fibres, and would eliminate the need to optically couple the device and the laser prior to analysis.

MULTIPLEXING FOR PARALLEL EXTRACTION AND QUANTIFICATION

The inventive device described lends itself to parallelization in both the sampling and quantification steps, due to both its cylindrical geometry and simplification of the analytical process.

FIG. 15 illustrates that parallel sampling could be accomplished by bundling multiple fibres, with the same or different coatings, to either probe multiple samples at once or to probe a single sample for multiple analytes. The bundle of fibres could also be used to provide efficient stirring during extraction. The extraction can be from multi-well autosampler plate, each well containing a different sample is extracted by a single fiber facilitating highly parallel determinations. The bundled extraction device could be employed for quantification by the MALDI process described above. The bundle could be multiplexed to a light source, and each individual probe irradiated in sequence by targeting the source at each individual fiber in succession. Simultaneously the sample end of each fiber would be positioned at the instrument for analysis. As shown in FIG. 15, a laser source 120 is irradiated in sequence onto each fiber in a fiber bundle 130 by means of a positioning device 122. The sample ends of the fibres in the bundle are directed into an extraction/desorption mesh 126. In this case only the tips of the fibres are coated with extraction phase 132 as this is the surface that is irradiated by the laser light. The sample end is positionable by means of a second positioning device 124. As each fiber is ready to be desorbed, it is positioned by the positioning device 124 at the sampling orifice of the mass analyzer 128 and the laser 120 is fired to intimate desorption.

Alternatively the probe bundle could be desorbed simultaneously into individual solvent desorption wells, with quantification by LC/MS.

Figure 38:
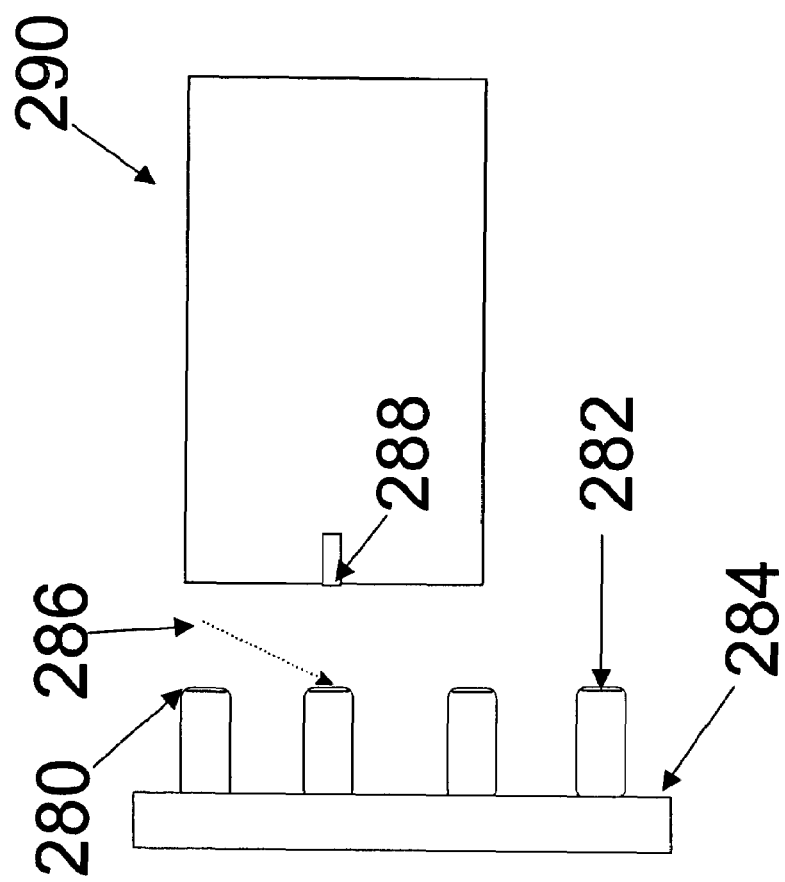
FIG. 38 shows a cover plate in use for delivery to MALDI MS instrument.

The combination of fiber MALDI analysis with multiwell plates may also involve a positioning device to allow proper placement of the distal end of each coated fiber within a small opening of each well, so as to submerge the extraction phase. This approach requires design of a relatively small and accurate positioning device, to accommodate the large number of wells in a single high density multiwell plate. The technology now allows for over 1,000 wells to reside on one plate. Other introduction techniques may be used to introduce a sample or fiber into a well, specifically by using micromachined microfluidic systems where many microfluidic channels can be placed in one microfluidic device to accommodate each fiber. This can be performed in combination with nanospray introduction to MS, where all fibres are desorbed in parallel in a microstructure, and subsequently each desorbed solution is introduced to MS in sequence. FIG. 38 shows the SPME interface to MALDI instrument using cover plate containing multiple fibers.

EXAMPLE 1

Polypyrrole Coating on Stainless Steel Wires and Use in a Biological System

Stainless steel wires (grade T-304V, 0.005") were from Small Parts Inc. (Miami Lakes Fla.). Lithium perchlorate (95%) and pyrrole (98%) were from Sigma/Aldrich (Mississauga, ON). Pyrrole was used as received for one month after opening, was stored refrigerated and the bottle was layered with nitrogen after each use. Polypyrrole (PPY) films were deposited onto the supporting electrode surface (stainless steel wire) by anodic oxidation of the pyrrole monomer in the presence of an aqueous electrolyte solution (counter ion). A potentiostat/galvanostat (Model 273, EG&G Princeton Applied Research) was used for the electrodeposition. The last 15 mm of the wires were coated potentiostatically at 0.8 V for 20 minutes. The placement of a silicon septum 15 mm from the end of the wire allowed for accurate control of coating length. The coating solution used was pyrrole (0.1M) and lithium perchlorate (0.1M) in water and was prepared fresh daily. Coating was performed in a custom designed 50 mL flow-through glass compartment. Coating solution was pumped through the compartment continuously to allow for one complete change of solution during each deposition (50 mL/20 min.). The stainless steel wires were cut into 10.7 cm sections with a razor blade and 2-4 cm at the end to be coated was etched with 400 grit silicon carbide polishing paper. Wires were then sonicated in acetone until required to prevent accumulation of oxides or other contaminants on the wire surface. Immediately before use the wires were rinsed briefly with water and were installed as the working electrode. The counter electrode consisted of a ca. 10 cm section of platinum wire (0.75 mm OD) formed into a coil of about 1.5 cm diameter. The stainless steel wire was placed into the coating solution in the centre of this coil. A calomel reference electrode was used. The polypyrrole coating thickness was estimated to be <10 μm thick. Prepared probes were then placed into vials with sufficient buffer to cover the extraction phase and autoclaved for sterilization.

Wires prepared as described above were characterized in a series of in vitro experiments. Benzodiazepine standards (1 mg/mL in methanol) were purchased from Cerilliant (Austin Tex.). These were diluted in methanol to prepare mixtures of various concentrations for use in sample preparation and instrument calibration. Samples were prepared from buffer, dog plasma or dog blood and spiked with an appropriate amount of the analytes of interest. The device was placed directly into the sample contained in an appropriate polypropylene sample vial, for a certain period of time. After extraction the probe was rinsed briefly with a stream of water and either analysed immediately or allowed to dry prior to analysis. Drugs were stable in the extraction phase when stored dry at room temperature for at least 24 hours.

Figure 20:
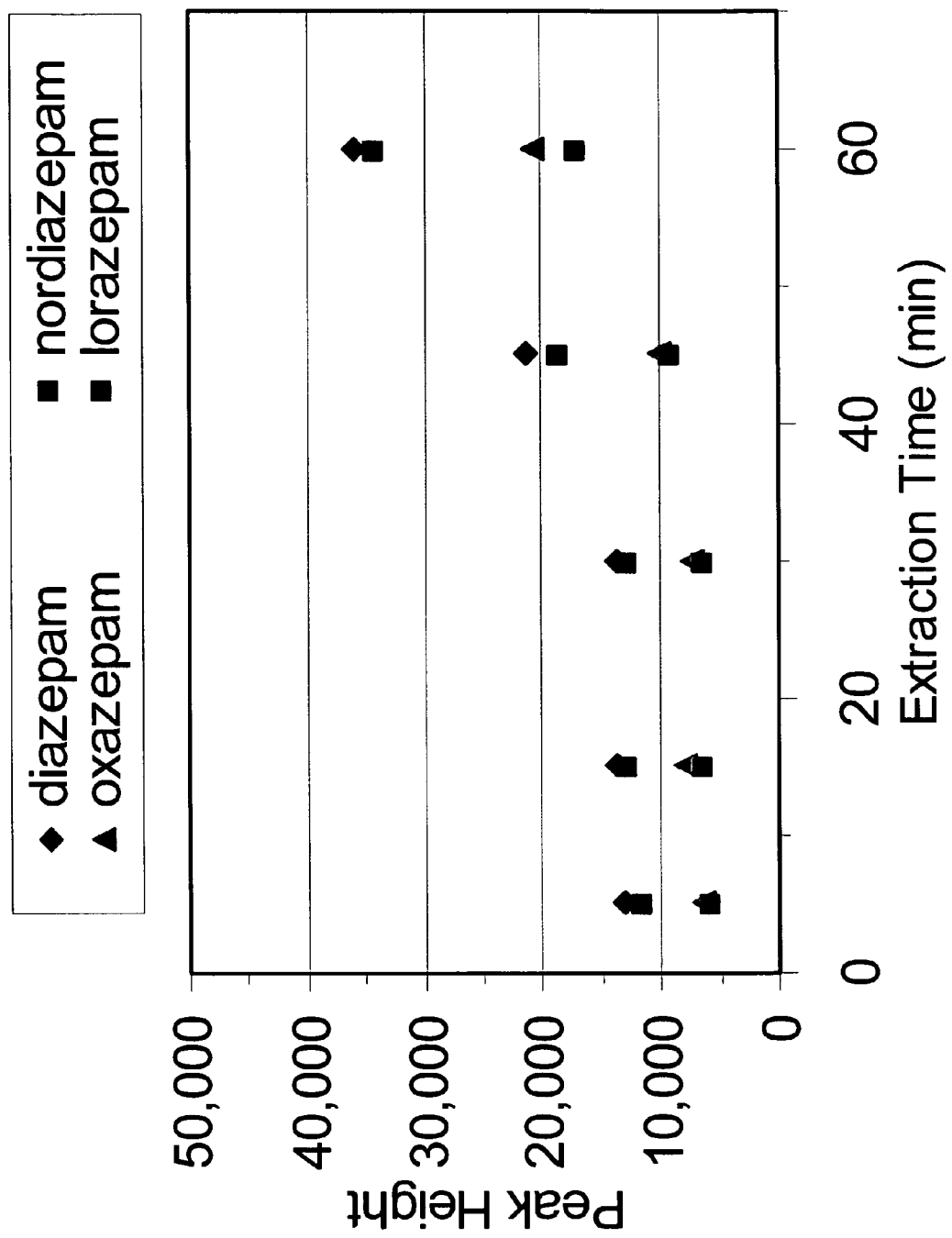
FIG. 20 shows extraction response versus time for standard devices.
Figure 21:
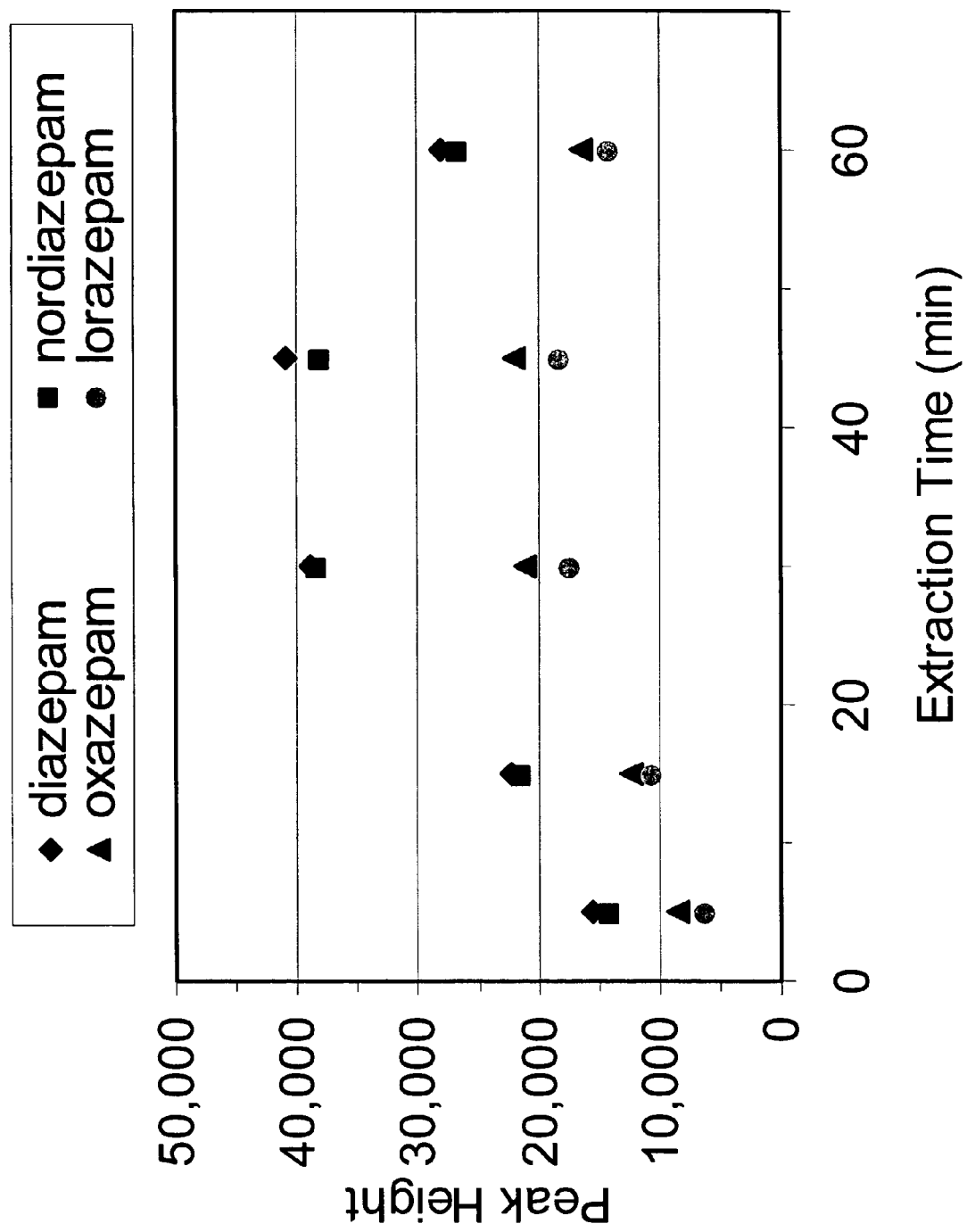
FIG. 21 shows extraction response versus time for pre-conditioned devices.

FIG. 20 and FIG. 21 show two alternatives for device response that may be achieved by this method. In FIG. 20 it can be seen that a fast initial equilibrium between the sample and native polypyrrole coated wires can be achieved. After a longer period of time, additional analyte is extracted as the polymer swells and exposes additional sites for extraction.

FIG. 21 shows that the polymer was preconditioned with methanol to provide a swelled polymer prior to extraction. The result is the elimination of the initial lag time seen in FIG. 20 and an immediate increase in amount extracted with maximal extraction seen after 30 minutes when the analyte has diffused throughout the bulk of the polymer to access the additional sites exposed during swelling. This provides for additional sensitivity at the expense of a slower response time.

Figure 22:
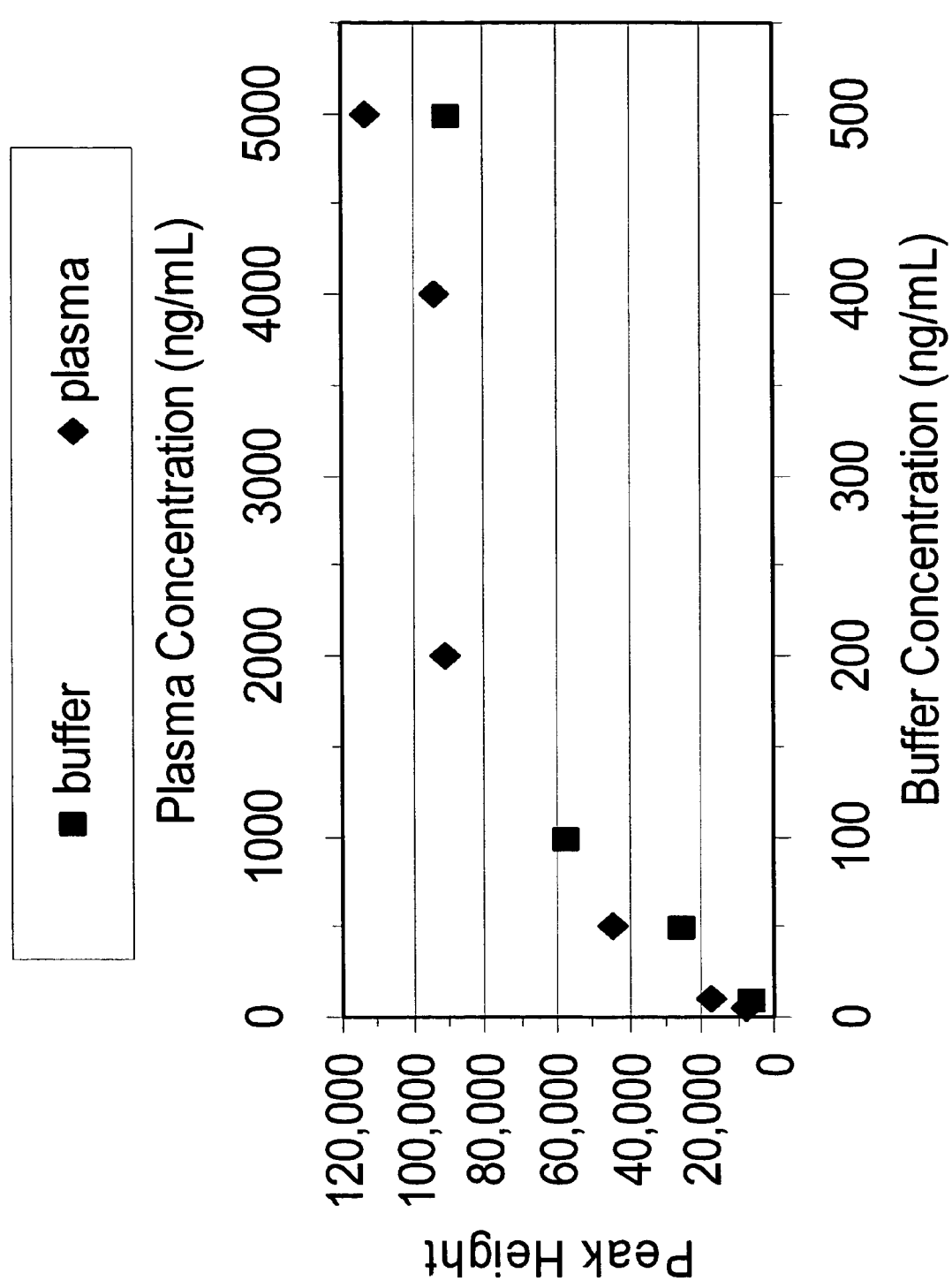
FIG. 22 provides a comparison of calibration in buffer and plasma, demonstration of linear response limit.
Figure 23:
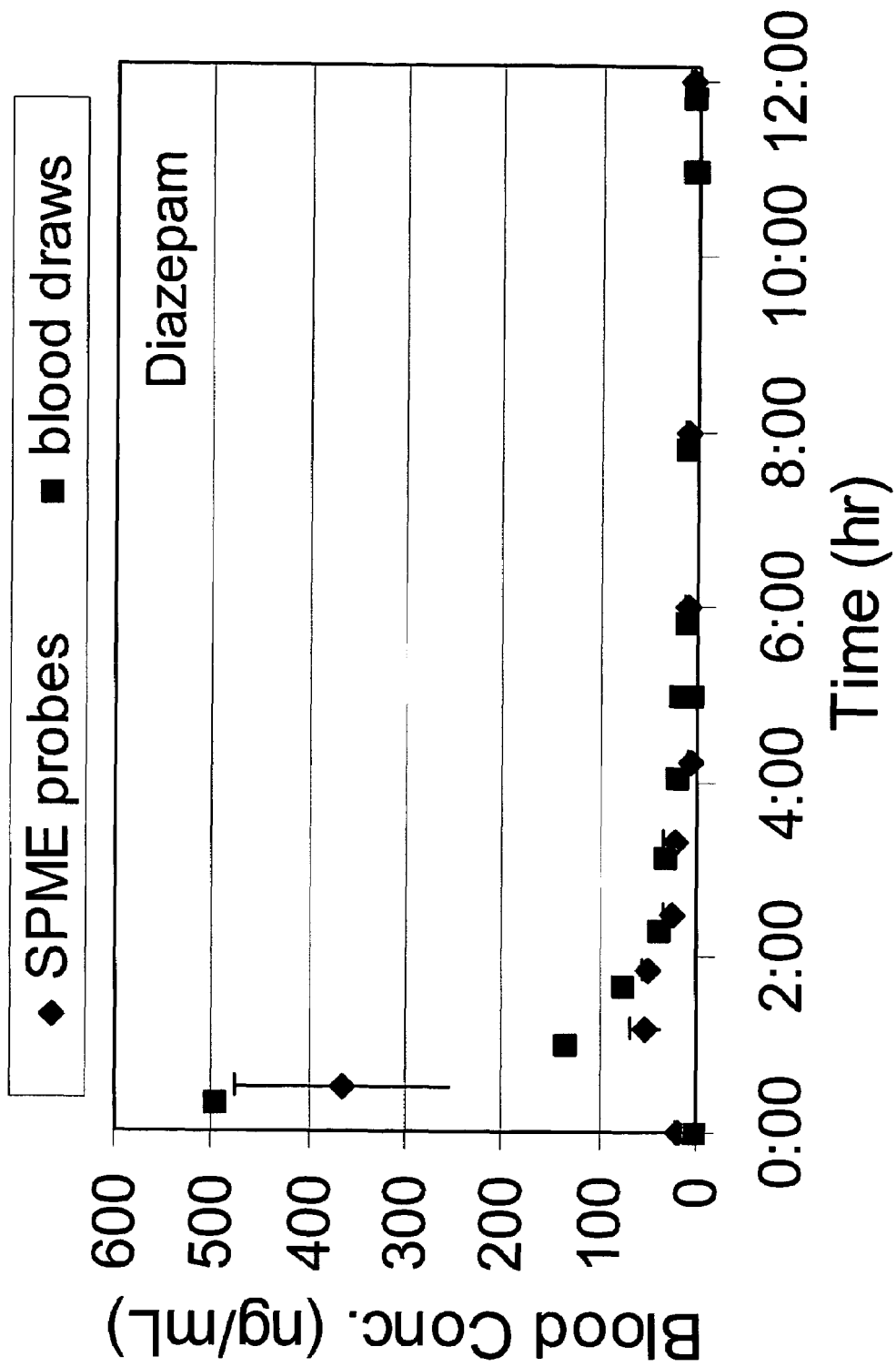
FIG. 23 illustrates an exemplary pharmacokinetic profile of diazepam.
Figure 24:
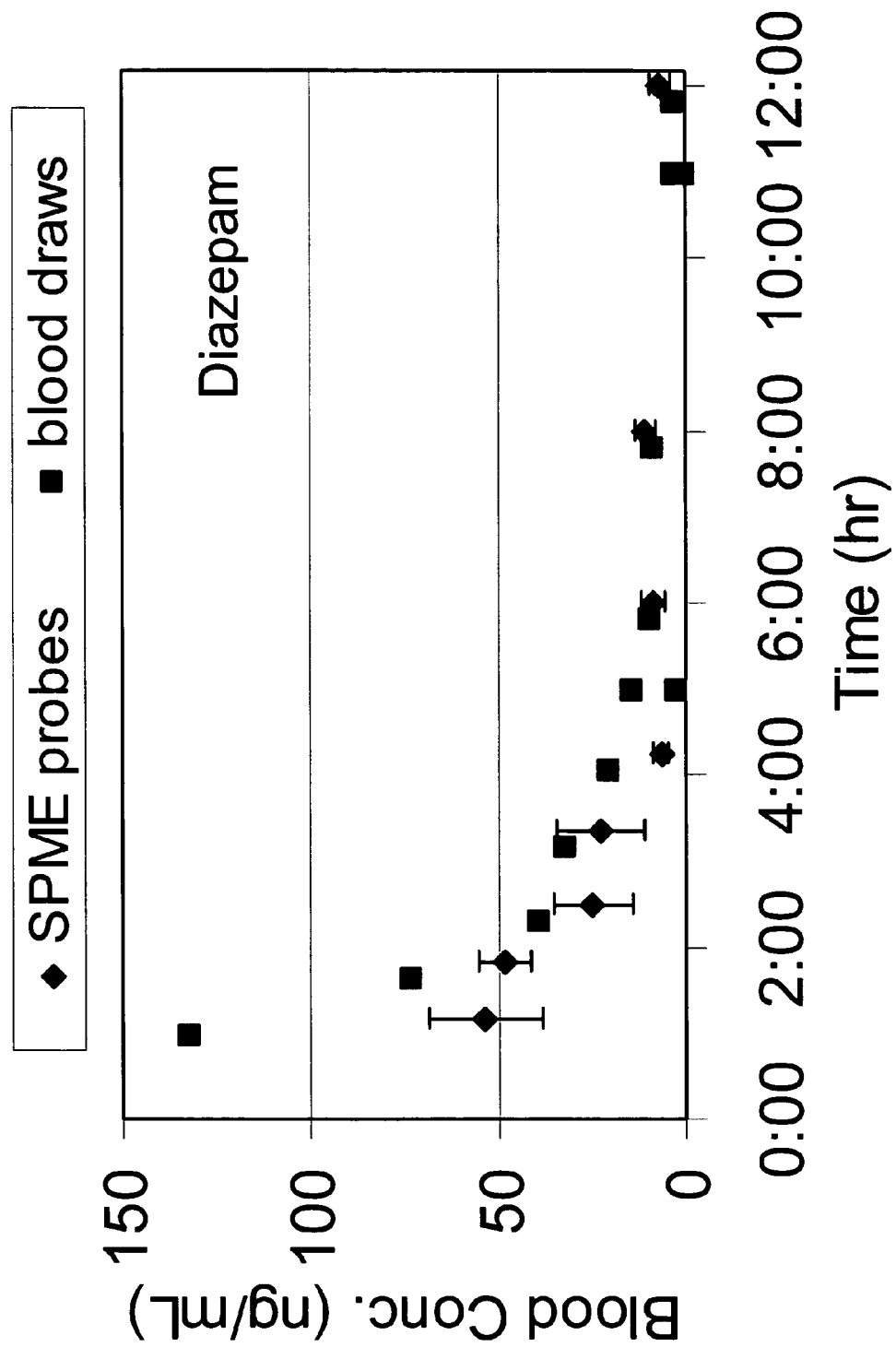
FIG. 24 illustrates an exemplary pharmacokinetic profile of diazepam, with an expanded y-axis.
Figure 25:
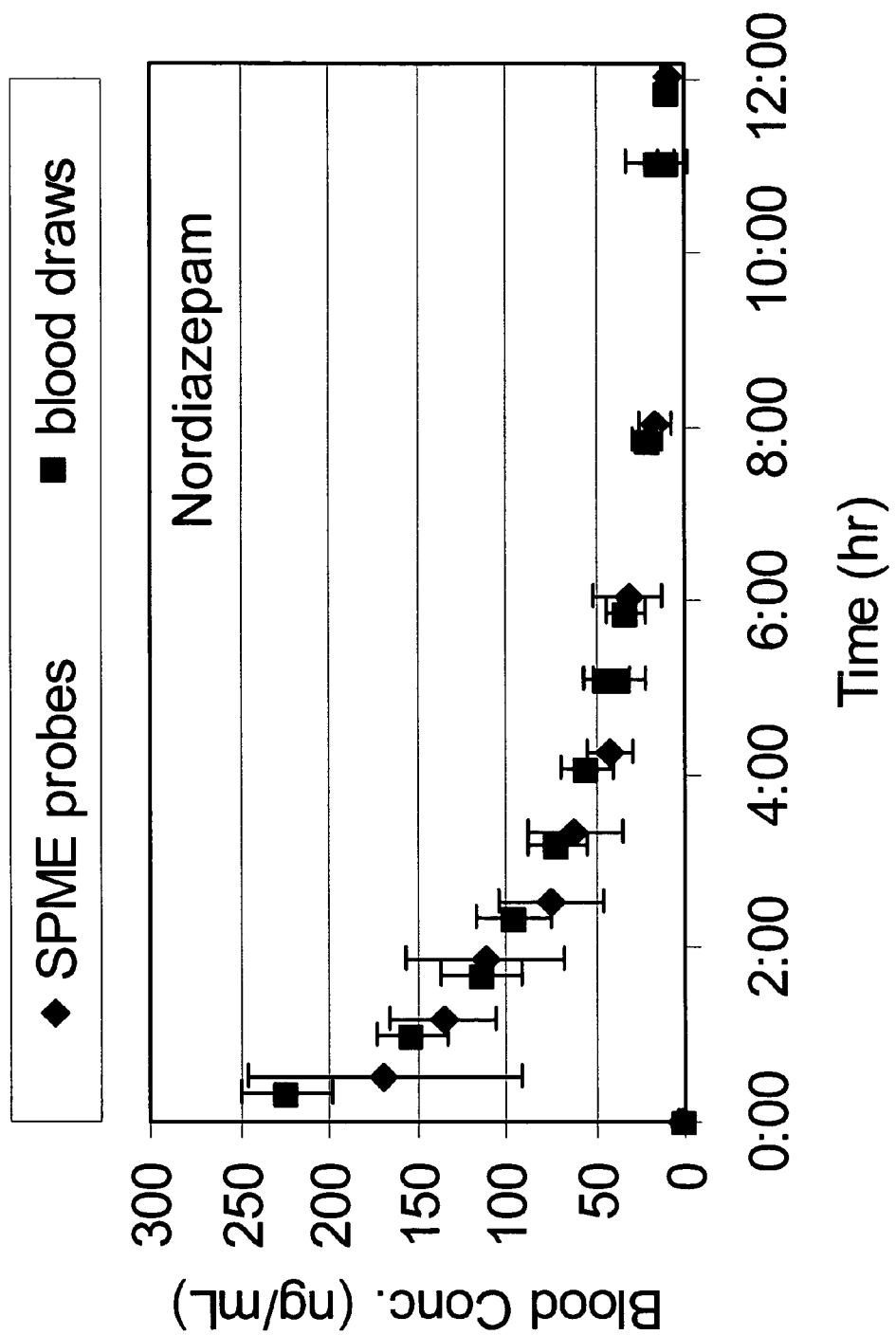
FIG. 25 illustrates and exemplary pharmacokinetic profile of nordiazepam.
Figure 26:
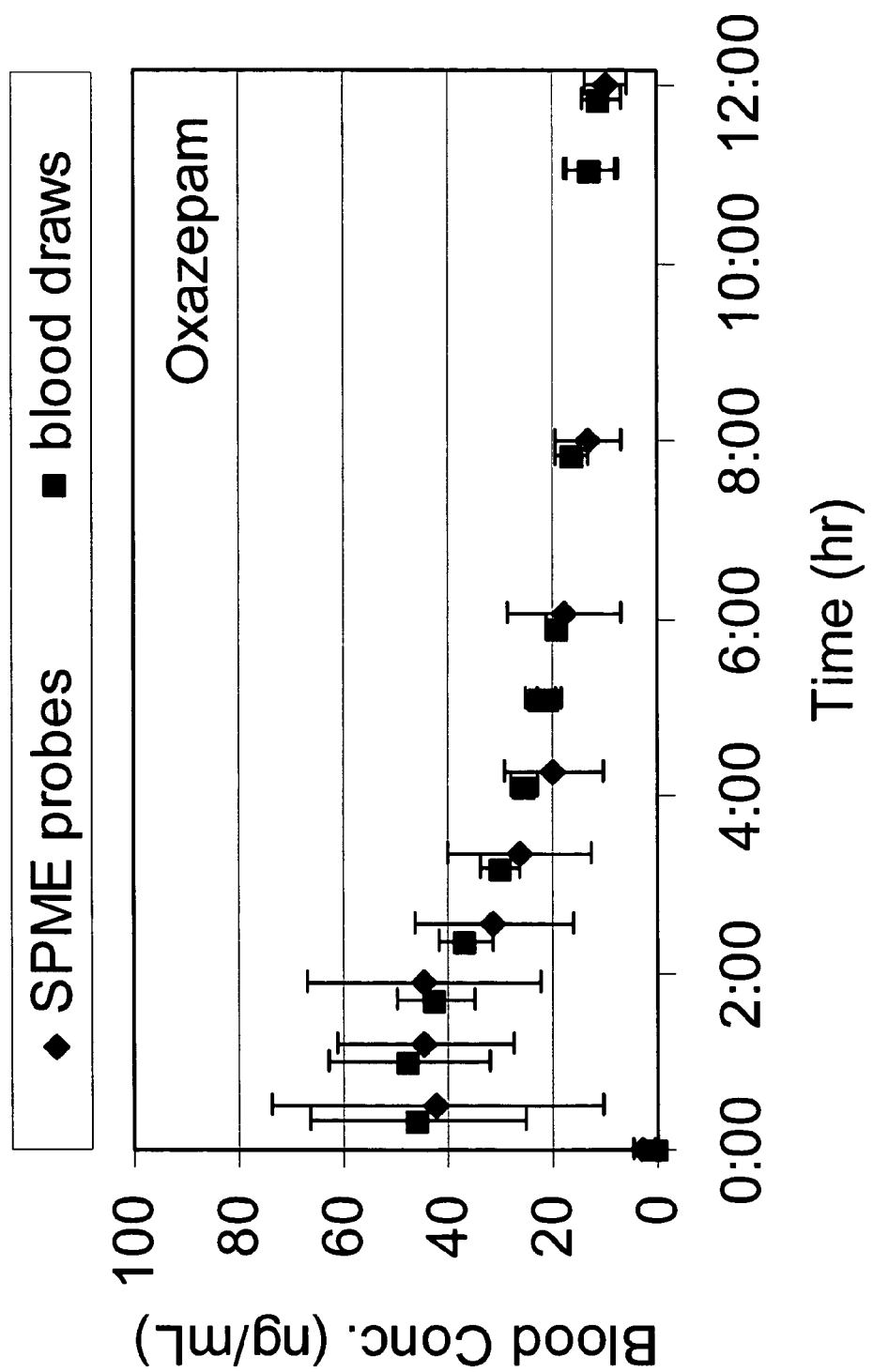
FIG. 26 illustrates an exemplary pharmacokinetic profile of oxazepam.

FIG. 22 shows the result of in vitro extraction calibrations from buffer and plasma. Because the device will only extract unbound drug and because the drugs under study are ca. 90% bound to protein, the plasma concentrations tested were 10× higher than the buffer concentrations. In buffer 100% of drug is free and 0% is bound to protein as no protein is present. In plasma, it is expected that 10% or less of the drug will be free. FIG. 22 demonstrates that the linear range attained is similar in buffer and plasma, based on free drug concentration. The figure also demonstrates that polymer extraction reaches maximal capacity in a solution with 100-200 ng/mL free drug.

After extraction (either in vivo or in vitro) the compounds on the device are desorbed in a small volume (10-20 µL) of desorption solvent, 75% methanol in this case. Maximal desorption is seen in as little as 20 sec. All or a portion of the desorption solvent is injected to an analytical instrument for analysis. This may be accomplished either on-line in a dedicated injection interface that takes the place of the regular injection port on a LC, or off-line in a small desorption chamber, followed by standard syringe injection of the desorption solvent by a commercial autosampler.

Figure 12:
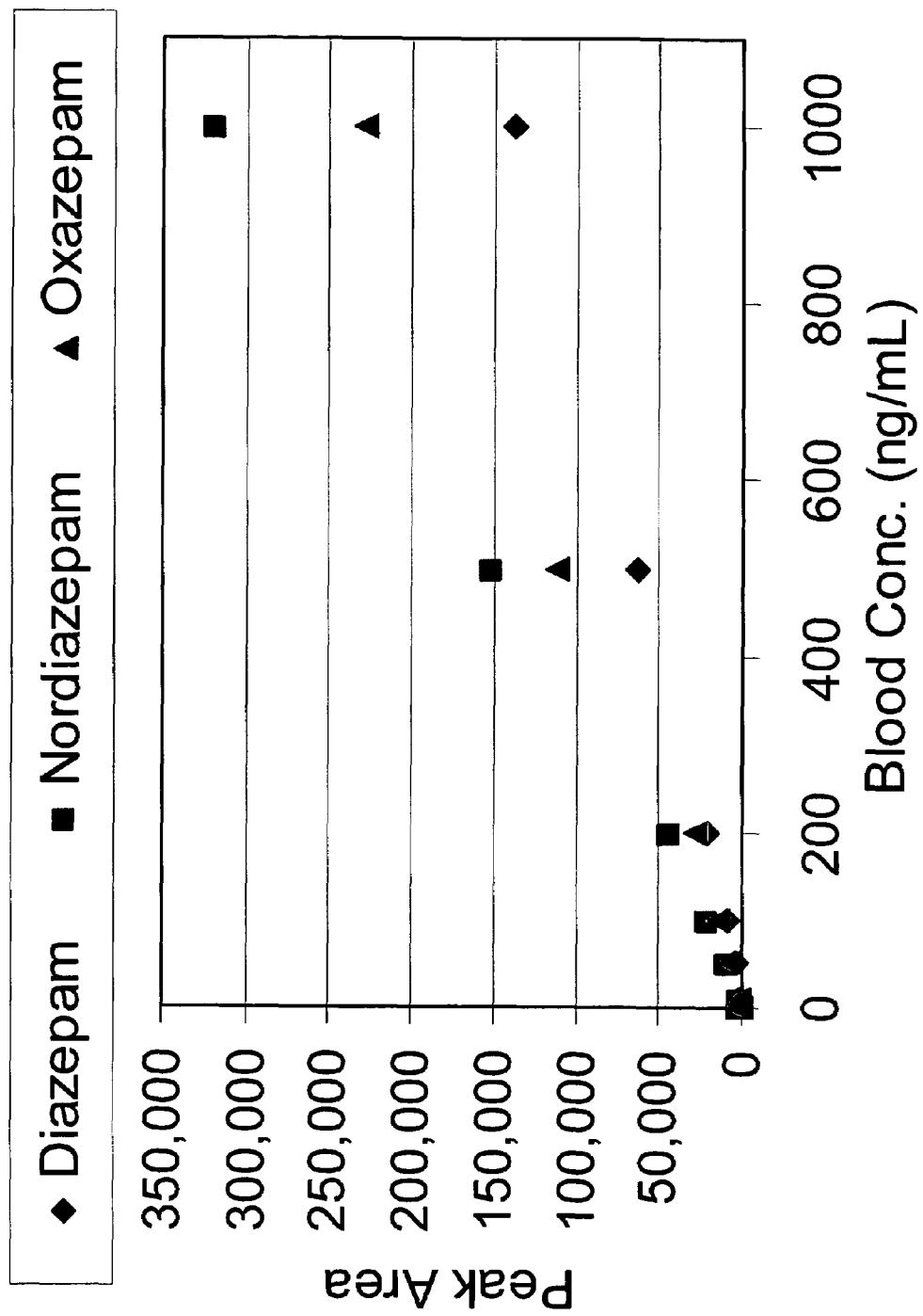
FIG. 12 illustrates calibration in whole blood used to calibrate device response.

FIG. 12 presents the results of a calibration from whole blood treated with an anticoagulant. The figure demonstrates good linearity in extraction over the range of total (bound plus free) drug shown.

FIG. 13 shows a chromatogram obtained after extraction of drugs spiked at 100 ng/mL from dog plasma, demonstrating the good chromatographic peak shape obtainable by the method. In this case the injection volume was ca. 11 µL, using the desorption solvent described above.

FIGS. 23 to 26 show the results of the use of the device by the catheter sampling method described above, for a pharmacokinetic study in dogs. In this case dogs were dosed with diazepam at time 0:00. Multiple samplings were performed from a catheter over the ensuing 12 hours. Calibration was by comparison to results from an external calibration in whole blood similar to that shown in FIG. 12. Also shown is a comparison to results obtained by multiple blood draws over the same time period, with conventional sample preparation and analysis as described in the description of the prior art. These results demonstrate that the device is useful for the application described and that the method described produces results in good agreement with devices and methods using invasive prior art sampling techniques.

Table 1 shows the limits of detection achieved in buffer and whole blood for a "probe" formed according to the invention. As can be seen from these data, the device and method allow an extremely sensitive detection of the analytes of interest, in this case: diazepam, nordiazepam and oxazepam.

TABLE 1

Limits of Detection Achieved in Buffer and Whole Blood

| Compound | Linear Range | detection limit (S/N = 3) ng/mL | slope | linear correlation ($r^2$) |
|---|---|---|---|---|
| SPME probe calibration from whole blood | | | | |
| Diazepam | 1-1000 ng/mL | 7.1 | 215 | 0.999 |
| Nordiazepam | 1-1000 ng/mL | 3.1 | 328 | 0.994 |
| Oxazepam | 1-1000 ng/mL | 2.7 | 258 | 0.996 |
| SPME probe calibration from buffer | | | | |
| Diazepam | 10-100 ng/mL | 0.43 | 306 | 0.999 |
| Nordiazepam | 10-100 ng/mL | 0.24 | 281 | 0.998 |
| Oxazepam | 10-100 ng/mL | 0.35 | 169 | 0.995 |

EXAMPLE 2

MALDI Analysis

In this Example, a medical aerosol compressor was used as the matrix sprayer, and 10 mg/mL matrix DHB solution was deposited into the nebulizer vial. After analyte extraction the fiber tip was placed 1.5 cm above the nebulizer vial, and by turning on the compressor very fine drops of the matrix DHB solution were formed and attached to the fiber tip. The 800 µm fiber was tested with the spray method for a 0.05 mg/mL TOAB sample solution. The times for matrix application were set at 45 seconds and 30 seconds, respectively, considering the lower analyte concentration. Two 3 minute air-dry times were applied before and after the spray of matrix.

Figure 27:
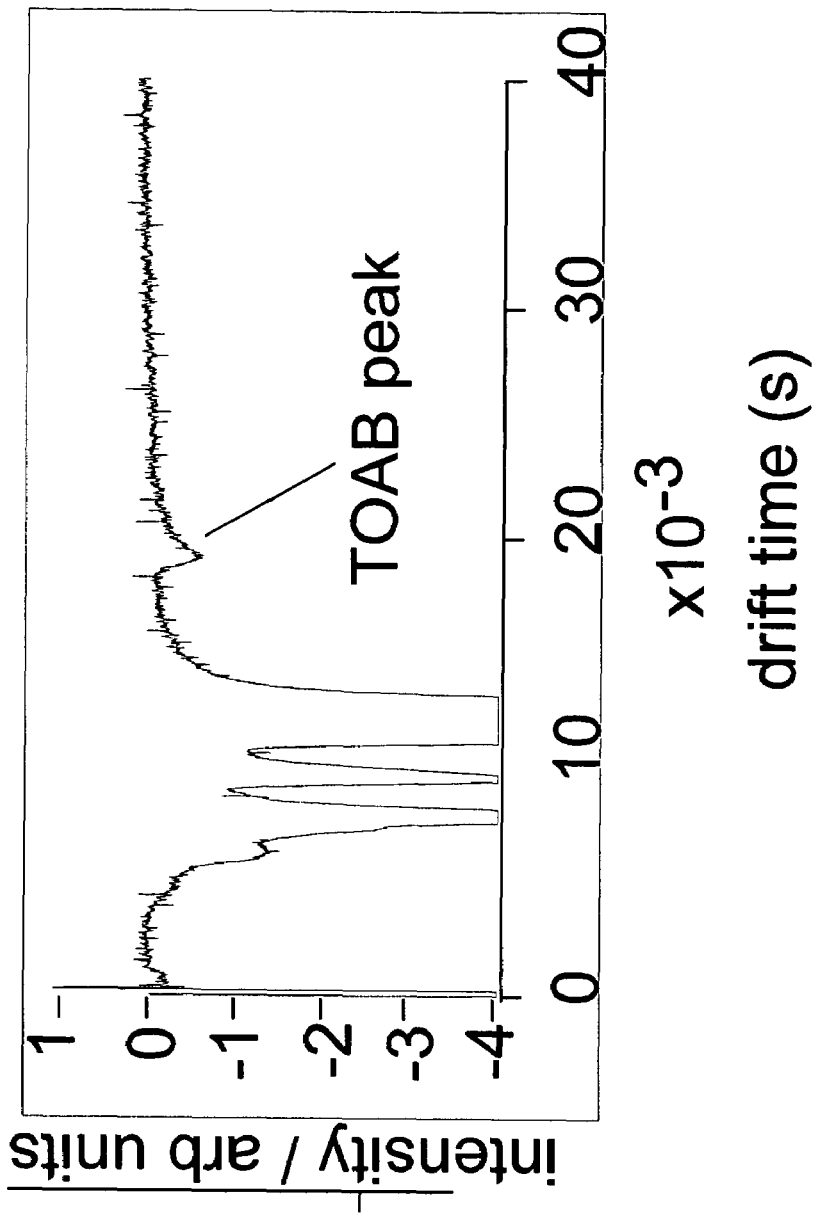
FIG. 27 shows an ion mobility spectrum obtained by matrix spray method at 0.05 mg/mL.

FIG. 27 shows an IMS spectrum from this analysis. The limit of detection was found to be 0.02 mg/mL with S/N ~2. This level is 10 times lower than the previous 0.2 mg/mL established by the 400 µm fiber using the pre-mixed method. The sensitivity has been increased dramatically. This great improvement was attributed to the larger surface area as well as the spray method.

In the work described above the laser pulse was shot down the core of the fiber. In addition to the advantages associated with reduced noise as described above, this is convenient as it is not necessary to carefully align the laser with the sample surface. The fiber itself accomplishes this. As an alternative however, it would still be feasible to conduct more of a conventional MALDI analysis where the laser is directed at the surface of the fiber. This would allow probes to be constructed from non-light conducting fibres, and would eliminate the need to optically couple the probe and the laser prior to analysis.

EXAMPLE 3

On-Fiber and In-Needle Laboratory

In micromachined devices, controlling flow is not simple since it requires pumps or electroosmontic flow means. In addition it is quite difficult to mix analytes in the small channels. A more efficient approach is to do sample processing on the surface or in thin layers adjacent to the surface. The structures chosen in this Example are the outer surfaces of fibers. Alternatively, the inside surface of a tube fiber could be used. This Example makes use of a small fiber to demonstrate a convenient sampling method to collect analytes from small objects. In this work capillary electrophoresis with fluorescence detection has been used to facilitate detection of small amounts of analytes extracted by the fiber.

Chemicals and materials. 4-fluoro-7-nitro-2,1,3-benzoxadiazole (NBD-F) was purchased from Fluka (Sigma-Aldrich Canada Ltd., Oakville, Ontario). Brij35® and all amino acids (glycine, L-phenylalanine, L-proline, L-glutamate and L-aspartate) were obtained from Sigma-Aldrich Canada Ltd. (Oakville, Ontario, Canada). Sodium borate was from Fisher Scientific (Nepean, Ontario, Canada). All of the solvents used were HPLC grade, filtered and degassed and all the aqueous samples were prepared with deionized water (NANOpure, Ultrapure water system). A manual SPME assembly and replaceable extraction fibers, coated with Carbowax-temprated resin (CW-TPR, 50 um) were purchased from Supelco (Canada).

Instrument. The high voltage power supply for the CE system was from Spellman High Voltage Electronics Cooperation, Plainview, N.Y., USA. The CE separation capillary and silica fibers were purchased from Polymicro Technologies LLC, Phoenix, Ariz., USA.

The fundamental components of the laser induced fluorescence detection (LIF) are the laser, focusing lens, objective lens, interference filter and photomultiplier tube. An Argon ion (Ar+) laser (~5 mW) was the excitation source. It provided an excitation wavelength of 488 nm (its maximum). The microscope objective lens (10×) and the low pass filter (530 nm) as an interference filter were from Melles Griot (Toronto, ON, Canada). The photomultiplier tube (PMT) and its socket including a high voltage power supply were purchased from Hamamatsu (R928 and C6271, Bridgewater, N.J., USA). In the design, the optical chopper and lock-in amplifier were used to enhance the signal indirectly. The optical chopper (SR-540) and lock-in amplifier (SR-510) were from Stanford Research systems (Sunnyvale, Calif., USA). The analog output signal from the lock-in amplifier was read by a plug-in data acquisition card (Star 4.5, Varian), which recorded at 20 Hz followed by the digitalization of the analog signal.

CE system set-up. The CE system was composed of a high voltage power supply and a separation capillary with an effective length of 45 cm (75 um I.D. and 385 um O.D.). The running buffer was 20 mM sodium borate, 10 mM Brij 35® and 2.5% methanol. The capillary was conditioned with 0.1 M sodium hydroxide (NaOH), water and running buffer for 15 minutes each. Between runs, the capillary was reconditioned with 0.1 M NaOH for 4 minutes followed by running buffer for 2 minutes. The running voltage was 12 kV. The injection was done hydrodynamically by raising the capillary inlet by 5 cm for 5 seconds.

In-solution derivatization reaction. The reaction solution was prepared by mixing 10 ul of each amino acid (0.01 mM in water), 10 ul of 1 mg/ml of NBD-F and 60 ul of 10 mM borate buffer at pH 8. This mixture was vortexed for 30 seconds and held in a 60° C. water bath for various periods of time (2, 5, 10, 30 and 60 minutes). The reaction solution was diluted to a final volume of 800 ul with running buffer and stored in an ice bath while waiting to be analyzed.

On-fiber derivatization reaction. A fiber was first cleaned by soaking it in ethanol. It was then dipped into a vial containing NBD-F (2-3 mg/ml in ethanol) for 10 min with magnetic stirring at 1000 rpm. After that it was transferred to a 1-ml Teflon centrifuge tube containing 200 ul of amino acids (0.1 mM) in sodium borate buffer (50 mM, pH 6.0) and dipped in the sample for 20 sec. A 4-ml amber vial containing 1 ml of triethylamine (TEA) was maintained in a 60° C. water bath. The headspace of this vial was basic. When the fiber with extracted analytes was exposed to it, the derivatization reaction took place (15 min).

Whole grape sampling with fiber/CE: interface and off-column desorption. The fiber/CE interface with off-column desorption was described previously. The desorption solvent (2 ul) was placed on the surface of the SPME fiber coating. This small droplet was manually rolled around the surface of the fiber coating. Finally this droplet was placed on top of a section of quartz tubing and it slipped down to the other end of the tubing where the capillary inlet was fixed. The capillary inlet contacted with this droplet for approximately 2 s. Since this quartz tubing was positioned 10 cm above the buffer vials, the droplet was hydrodynamically injected. The capillary electrophoresis was subsequently started. With such an interface, a commercial carbowax/TPR SPME fiber from Supelco could be used.

Fiber/CE interface: on-column desorption. On-column desorption has been described previously for a fiber/CE interface. The SPME micro fibers were made by attaching a 2-cm long silica fiber (100 um diameter) to a 10-cm polyimide coated silica capillary (100 um ID×365 um OD) with epoxy glue. The unit was air-dried overnight. The micro fibers were further etched to approximately 50 um diameter with 50% HF. These fibers were finally housed in stainless steel tubes and were sent to Restek Corporation, Bellefonte, Pa. for coating with carbowax.

Results and Discussion: Separation of amino acid derivatives. The critical micellar concentration (CMC) of Brij 35® is 0.9 mM. The CE running buffer used in these experiments had Brij 35® of 10 mM. Brij 35® not only forms micelles to improve the separation resolution, but also enhances the fluorescence intensity of the amino acid derivatives. Some studies have shown that Brij 35® will enhance the florescence signal of such derivatives by at least three times. The methanol (2.5%) in the running buffer functioned as organic modifier. It helped to increase the solubility of the solutes and enlarged the migration time window. As a result, a better resolution was achieved. Under these conditions, a mixture of five amino acid derivatives (phenylalanine, proline, glycine, glutamate and aspartic acid) was analyzed within 20 minutes.

On-fiber derivatization reaction of amino acids. The on-fiber derivatization of amino acids with NBD-F was first established with fibre/HPLC/fluorescence detector system described. On-fiber derivatization and a CE/LIF detection system has been described in the experimental section. The separation of amino acids derivatives was established. NBD-F reacts with to amines and nucleophilies under a mild basic condition. The peaks observed of sp-a represented the side products of the reaction of NBD-F and TEA. The peaks of sp-b observed are representative of the side products of the reaction of NBD-F with the aqueous buffer components and the sample matrix. NBD-OH is the major side product formed in the reaction of NBD-F with aqueous solution. Glycine could not be analyzed under these conditions because the glycine derivative co-eluted with one of the side-product peaks, sp-b. Glycine has an average migration time of 6.47 min (RSD=1.37%). Using a similar procedure, the fibre/CE/LIF detection system was used for the amino acid analysis. In this study, the CE/CE with off column desorption was used.

Whole grape sampling: Off-column desorption CE/CE interface. To demonstrate the application of this technology to the direct analysis of small living objects with on fiber derivatization coupled to a CE/LIF detection system, whole grapes were used as the samples. With a NBD-F doped fiber, the sampling procedure and derivatization reaction took 20 seconds and 20 minutes, respectively. The resulting electropherograms from this method with green grape (G) and red seedless grape (R) illustrate a glutamic derivative found at 7.05 min for the green grape sample and 7.01 min for the red seedless grape sample. These migration times corresponded to the L-glutamate standard 7.04 min. In the CE/CE experiments, most of the peaks were saturated such that phenylalanine and proline derivatives were hidden in the saturated signal. For further identification of amino acids in the sample, the juice from the grapes was analyzed. The glutamate was also found in the grape juice sample in the form of glutamic acid.

On-column desorption CE/CE interface. With the off column desorption, fibers with carbowax/TPR coating were used for sampling, while the on-column desorption was used with microfiber having thinner coating. These microfibers had a diameter between 75-50 um, and so could be used to sample smaller living objects. These microfibers were coated with carbowax. Electron microscopy was used to visualize the fibers and the fiber coating was found to be about 10 nm.

The feasibility of using these fibers for the on-fiber labeling reaction coupled to CE/LIF detection system was tested. First, the blank NBD-F solution was extracted with the fiber and desorbed on-column. The doping of NBD-F was successful. After the sampling of amino acid standard and reaction in the TEA headspace, no product was detected.

EXAMPLE 4

Instrument and Method Calibration Using Fibers Loaded with Calibration Compound

One of the main advantages of the invention is that it allows very convenient introduction of extracted components onto analytical instrumentation, such as gas chromatography, liquid chromatography, supercritical fluid chromatography, capillary electrophoresis, micro-channel devices and even directly to mass spectrometry and detection instruments. This feature can be further explored for delivering calibration standards to analytical instrumentation. Currently standards are delivered to the instrument by injecting the solvent mixture containing appropriate calibration compounds. However, presence of solvent frequently interferes with calibration procedure. Therefore, it would be to user benefit to eliminate solvents from the calibration procedure. It can be accomplished by desorbing standard loaded fiber into appropriate instrument.

The loading of the fiber can be accomplished by exposing sorbent-coated fiber (extraction phase coated) to the source of the standard. The standard is then adsorbed onto the fiber coating. Another approach is to immobilize chemical standards via chemical reaction onto the fiber, which then is released to the instrument under conditions of increased temperature, light, chemical potential, mobile phase, etc. The second approach ensures stability of the calibrant, but as this Example demonstrates the first approach can also be very effective.

Two calibration methods were used. The first approach used solid sorbent coated fibres. One of the methods is to deliver the calibration compound by utilizing SPME fiber to the analytical instrument. The standard is first extracted from the standard mixture using strong sorbent followed by introduction of the standards loaded fiber into analytical system requiring calibration. In this approach liquid injection is avoided and thus solvent interference to the determination of trace VOC (volatile components) is eliminated. Satisfactory calibration curves were obtained for the very volatile compounds namely methanol, acetone, dichloromethane and chloroform when a 75-um carboxen™/polydimethylsiloxane (CX/PDMS) fiber/coating was used. The standard gases or gas mixtures of VOCs were prepared using the NIST traceable certified permeation tubes combined with gas chambers or by microwave-assisted evaporation. "Stepwise" is the approach to the second calibration method developed during this work for on-site calibration of fibres. In this approach the CX/PDMS coated fiber was loaded with standard followed by exposure to the investigated system and then introduction into GC system for analysis. The accumulation time of analytes can be controlled equal to or different from that of the standard, and the response factors for the analytes can be adjusted accordingly. A good reproducibility of the response factors for BTEX was obtained with the stepwise method. Satisfactory results were obtained by using this method in quantitative analysis of BTEX in the gas station air. The introduction of standard via the stepwise procedure makes the technique more useful in field applications. This approach in some respects resembles standard addition, but also external calibration. It can be used to detect leaks, contaminations and losses from the time of standard loading onto the fiber to introduction to analytical instrument.

Preparation of standard gases or gas mixtures. Up to now several methods have been developed for preparation of standard gas. Two methods were employed in this work to prepare the required standard gases or gas mixtures.

Preparation of gas mixture of BTEX using NIST permeation tubes. The standard gas mixture of BTEX (benzene, toluene, ethylbenzene, p-xylene and o-xylene) was generated with the NIST traceable certified permeation tubes (Kin-Tech Laboratories, La Marque, Tex.) and the gas chambers build in our laboratory. It was a flow-through system with which a constant concentration of standard gas (or gas mixture) can be gained. The temperature was controlled at 50° C. and the air flow rate was at 300 ml/min. The gas mixture was sampled from the gas chamber.

Microwave-assisted generation of gas standards of VOCs. A domestic microwave oven (1000 W, Model MW5490W, Samsung, Korea) and 1-L gas sampling bulbs (Supelco, Bellefonte, Pa.) were used for preparation of standard gases and gas mixtures of the investigated VOCs with different concentrations. The inner walls of glass bulbs were deactivated by silanization and the bulbs were cleaned with flushing nitrogen before use. For preparation of standard gases or gas mixtures of BTEX, 1,3-dichlorobenzene, 1,1,2-trichloroethane and tetrachloroethylene, a clean piece of glass wool (ca. 10 mg) was set inside the sampling port of the bulb each time and was moistened with deionized water (15 µL). Water was used to absorb microwave energy and then to prompt the evaporation of the compounds that are poor absorbers of microwave. For preparation of standard gas mixtures of acetone, methanol, dichloromethane and chloroform, no glass wool and water were needed. The port of the glass bulb was sealed with a Teflon-faced silicon rubber septum through which a certain volume of liquid of target compound (or mixture of several compounds) was injected onto the glass wool. Finally, the bulb was placed into the microwave oven to receive microwave radiation for 90 s. The microwave output was always set to the maximum power level. After cooling the Supelco bulb to room temperature, analysis of the standard gas was performed through the sampling port of the bulb where a septum is located.

The device and the "stepwise" procedure. Fiber coatings and conventional samplers used were provided by Supelco (Bellefonte, Pa.). The coatings utilized included 75-µm Carboxen™/Polydimethylsiloxane (CX/PDMS), 85-µm Polyacrylate (PA), 100-µm Polydimethylsiloxane (PDMS) and 65-µm polydimethylsiloxane/divinylbenzene (PDMS/DVB).

The stepwise procedure was conducted as follows: first, the fiber was exposed to tetrachloroethylene standard gas in the bulb, then the fiber was withdrawn into the needle after 2-min extraction and a Thermogreen Septum (LB-2, Supelco) was used to seal the tip of the needle. When using the field SPME sampler, no separate sealing septum is needed. The tetrachloroethylene loaded fiber was then exposed to BTEX standard gas mixture in the chamber or to real air sample for a few minutes. Finally, the fiber was transferred to the GC injector to desorb the standard and analytes at the same time.

GC-FID analysis of analytes. A Varian model 3500 GC equipped with a flame ionization detector (FID) was employed for sample analysis. A SPB-5 capillary column (30 m×0.25 mm×1 µm) from Supelco (Bellefonte, Pa.) was used and hydrogen as carrier gas at 30 psi. The column was programmed as follows: 35° C. initial, held for 1 min, ramp to 135° C. at 10° C./min and held for 1 min. The detector was maintained at 280° C. For the PA, PDMS and PDMS/DVB fibers, the injector was controlled at 250° C. and desorption time was 1 min, while CX/PDMS fiber was desorbed for 2 min at 300° C.

Comparison of introduction of VOCs standards into GC system by syringe injection of standard solution and by standards-loaded fiber. Several very volatile compounds, namely acetone, chloroform, dichloromethane and methanol, were selected for investigation. A standard solution was prepared using methanol as the solvent and the concentration of acetone, dichloromethane and chloroform was 10 μg/ml for each compound. The GC-FID chromatogram obtained by injecting 0.1 μl of the standard solution into the GC system illustrated that the solvent peak was too large to be well separated from peaks of other compounds and thus made it difficult to accurately determine those trace components.

On a contrary, there was no big solvent peak appearing in the chromatograms obtained by injecting a standards-loaded fiber into the GC system and an ideal separation and identification of the VOCs were therefore achieved. The analysis of the standard gas mixture was conducted for 3 min using a 75-μm CX/PDMS fiber and the concentration of acetone, chloroform, dichloromethane and methanol in the standard gas mixture was 50.5 μg/L for each compound. Due to the avoidance of solvent injection, it became easy to get satisfactory chromatograms for the micro amount of VOC standards, even for the very volatile compounds that possess quite short retention times.

In addition, it is difficult to obtain a calibration curve by directly injecting pure liquid of individual VOC or liquid mixture of VOCs into GC system to avoid introduction of plenty of solvent due to the difficulty of accurate injection of a very small volume (<<0.1 μl) of liquid standards into the GC system to match the quantitative ranges of trace analysis.

Calibration curves obtained with this technique for GC analysis of some VOCs. Two different fibers were used to extract the standard gas mixtures of two different groups of VOCs. The very volatile compounds, including acetone, chloroform, dichloromethane and methanol, were extracted with a 75-μm CX/PDMS fiber, which has a high affinity towards to VOCs as described above. BTEX were extracted with a 100-μm PDMS fiber. It is known that the PDMS fiber extract target compounds by absorption while CX/PDMS fiber works by adsorption. By introduction of the VOCs standards into GC system with fibers, satisfactory calibration curves regarding the concentration-response relationship for SPME-GC-FID analysis of the mentioned VOCs were obtained and shown in FIG. 2. The related calibration equations were listed below:

Methanol: $A=767.69C+3564$, $R^2=0.9937$ (1-a)

Acetone: $A=3234.8C+22693$, $R^2=0.9952$ (1-b)

Dichloromethane: $A=1004.6C+7271.5$, $R^2=0.9965$ (1-c)

Chloroform: $A=980.46C+719.5$, $R^2=0.9993$ (1-d)

Benzene: $A=106.18C-1069.5$, $R^2=0.995$ (2-a)

Toluene: $A=326.42C-4320.8$, $R^2=0.9993$ (2-b)

Ethylbenzene: $A=711.53C-6136.8$, $R^2=0.9958$ (2-c)

p-Xylene: $A=868.43C-10704$, $R^2=0.9994$ (2-d)

o-Xylene: $A=995.98C-9588.1$, $R^2=0.9972$ (2-e)

where A is the chromatographic peak area (counts) and C is the concentration of VOCs standard gas (μg/L).

The experimental results demonstrated that the investigated fibers are efficient for introducing VOCs standards into GC system without solvent injection for getting calibration curves and GC-GC is a highly feasible method for quantitative analysis of VOCs, even for the very volatile compounds.

Moreover, it is also possible to establish the "mass: response" calibration curves for GC analysis of VOCs by introducing standards with SPME fibers. When absorption-type fibres are employed to extract analytes, there is a direct relationship between the initial analyte concentration in the sample ($C_0$) and the amount of the analyte extracted by the fibre at equilibrium (n) according to Equation 3-a:

$$n = \frac{K_{fs}V_sV_fC_0}{V_s + K_{fs}V_f} \quad (3\text{-}a)$$

where $K_{fs}$ is the fibre/sample partition coefficient, $V_f$ is the fibre coating volume and $V_s$ the sample volume. For adsorption-type SPME process, the amount of analyte A extracted by the fibre at equilibrium (n) also grows with the increase of the initial analyte concentration in the sample ($C_{0A}$) before saturated adsorption reached:

$$n = C_{fA}^\infty = \frac{K_A C_{0A} V_s V_f (C_{f\,max} - C_{fA}^\infty)}{V_s + K_A V_f (C_{f\,max} - C_{fA}^\infty)} \quad (3\text{-}b)$$

where $K_A$ is the adsorption equilibrium constant of analyte A, $C_{fA}$ is the concentration of analyte A on the fibre at steady state, $C_{fmax}$ is the concentration of active sites on the surface (corresponding to the maximum achievable analyte concentration on the surface), $V_s$ and $V_f$ are the volumes of the sample and the fibre coating, respectively.

Stability of VOCs on extraction phase coatings after exposing the coatings to zero air. Analytes present in a sample may absorb or adsorb to the extraction phase coating. However, similar to other extraction procedures, enrichment is followed by an opposite procedure, the release of extracted compounds from the coating phase. Therefore, when a coating loaded with some VOCs is exposed to pure air, a part of extracts will transfer to the air and then the extracts tend to reach an equilibrium distribution between the coating and air phases. The release of the extracts from the coating phase depends on a lot of factors, mainly the compounds' and coatings' properties, the temperature of the environment and the differences of the compounds' concentrations in the coating phase and in the sample or environment. It was shown in Table 2 that the remains of several VOCs (BTEX were included) on the 85-μm PA, 100-μm PDMS and 65-μm PDMS/DVB coatings ranged from 0 to 91.5% after exposing the coatings to zero air for 1 min at room temperature. However, the 75-μm CX/PDMS coating could store the extracts as much as 89.9%-97.2% even through a 6-min exposure to zero air under the same conditions. Actually, no obvious losses could be found for most of the extracts on the 75-μm CX/PDMS coating when exposure time was controlled within 4 min. Thus it is possible to allow a "stepwise" procedure conducted with the CX/PDMS coating—that is, this coating can be used to extract a compound in first step and then transferred to extract other compounds while the compound extracted previously still remains on the coating.

Selection of internal standard for BTEX analysis with stepwise Procedure. 1,3-dichlorobenzene, 1,1,2-trichloroethane and tetrachloroethylene were tested, respectively, as internal standards for BTEX analysis when a 75-μm CX/PDMS coating was used. The CX/PDMS coating has a strong affinity towards these compounds and their storage on the CX/PDMS coating was close to that of BTEX. Considering their chromatographic behaviors, tetrachloroethylene is the best internal standard for BTEX analysis since it can be well separated from BTEX and its peak is located in the central position of the chromatogram. Further investigation demonstrated that, under the selected conditions, the loading of tetrachloroethylene on the fiber did not affect the BTEX, and in turn, the BTEX did not affect the storage of tetrachloroethylene on the fiber either. Tetrachloroethylene as the internal standard for BTEX analysis has another advantage—that is, its background is generally not present in main BTEX sources like petroleum. However, tetrachloroethylene also has its drawbacks: it is a halogenated compound and the GC-FID response for it is not as sensitive as for BTEX. The problem involved in determination sensitivity for tetrachloroethylene can be solved by using selective detectors like MSD or FPD.

Response factors for BTEX when tetrachloroethylene was used as internal standard. For chromatographic analysis, the response factor (F) can be defined as the following form:

$$\frac{Ax}{Cx} = F\frac{As}{Cs}, \qquad (4)$$

where Ax and As are the peak areas of analyte X and internal standard, while Cx and Cs the concentrations of analyte X and standard after they have been mixed together. For the use of tetrachloroethylene as internal standard for BTEX analysis following the stepwise procedure described above, the standard is not mixed with analytes before they were extracted onto the SPME fiber. In such a case Cs stands for tetrachloroethylene's concentration of the standard gas and Cx is individual BTEX's concentration in the sample.

For the stepwise GC/FID analysis of BTEX, the response factors were measured. The time for of BTEX was 2 min, equal to that for the standard. It can be seen that the response factors highly coincided for duplicate tests in almost all cases. This reflects that the stepwise procedure is a feasible and practicable method to introduce internal standard for GC analysis of BTEX when the CX/PDMS coating is used.

Effect of extraction time on response factors for stepwise procedure. It should be noticed that the response factors discussed above are not only related to the sensitivity of GC-FID determination to individual BTEX but also depend on the SPME efficiency for them. Since the standard and BTEX were not extracted at the same time during the stepwise procedure, the time for BTEX can be controlled equal to or different from that for the standard. Obviously, time control will significantly affect the response factors. This is one of special features of the stepwise procedure distinguishing with the conventional way to use internal standards. In the conventional way, the extraction of analytes and internal standard is conducted simultaneously. It was found that the response factors varied linearly with the time for SPME of BTEX in the range of 1-5 min when SPME time for tetrachloroethylene (standard) was constantly controlled as 2 min. The linear equations obtained were as follows:

Benzene: $F=4.265t+1.301$, $R^2=0.9979$; (5-a)

Toluene: $F=5.776t+0.402$, $R^2=0.9981$; (5-b)

Ethylbenzene: $F=4.663t-0.031$, $R^2=0.9996$; (5-c)

$p$-Xylene: $F=4.623t-0.247$, $R^2=0.9993$; (5-d)

$o$-Xylene: $F=4.767t-0.703$, $R^2=0.9963$, (5-e)

where F is response factor and t is time in minute for BTEX.

The concentrations of both standard and analytes were within the linear ranges when the internal standard was used. GC-FID is known to have a linear response to VOCs during a very wide range and so is the inventive procedure with the CX/PDMS coating. The excellent linearity of the response factors for BTEX varying with the extraction time also reflected that the compounds' concentrations studied were located within the linear range.

Field application—analysis of BTEX in the air of a gas station. The VOCs (BTEX were the interests) were sampled from a gas station that is 5-min walk to our laboratory, using the home-made field sampler with a 75-μm CX/PDMS coating. It was a clear day and the temperature was ca. 24° C. when the sampling was conducted. The glass bulb holding the standard gas of tetrachloroethylene (8.1 μg/L) was carried to the field and analysis of tetrachloroethylene was performed prior to BTEX. The sampling time was 2 minutes for the standard and 4 minutes for the gas station air. As soon as the sampling was finished, the sampler was delivered to the laboratory and then the fiber was immediately introduced to GC-FID. The identification of individual BTEX was based on their retention times as well as GC-MS analysis using a Hewlett-Packard 6890 GC equipped with a 5973 MSD (Agilent Tech., USA). Tetrachloroethylene was not found in the gas station air itself. The separation of standard and BTEX from other components of the extracts was very good, only one peak might contain m- and p-xylenes, which couldn't be separated from each other under the selected chromatographic conditions. Finally, using the peak areas obtained (As and Ax), the standard concentration (Cs) and the response factors (F) given by Equations 5-a-5-e, the concentrations of BTEX in the air were calculated according to Equation 4.

Conclusion. For determining calibration curves using GC analysis of VOCs in air, fiber was successfully used to introduce VOCs standards into GC system without solvent injection. The avoidance of solvent injection with the inventive technique made it easy to obtain satisfactory chromatograms for micro amount of VOC standards, even for the very volatile compounds that possess quite short retention times. Moreover, a stepwise method was developed to introduce internal standard for GC analysis of BTEX in field application. The CX/PDMS was proved to be the only suitable coating to fit this method due to its extraordinary affinity towards VOCs. Tetrachloroethylene was selected as the internal standard for reasons such as its proper retention time compared with those of BTEX for GC analysis, similar behaviors to BTEX on the CX/PDMS coating and very low background in main BTEX contamination sources in the environments. Using the developed method, analytical results can be calibrated without a necessity to spike standard material into samples, hence it makes the inventive procedure even more advantageous in field applications.

However, since the standard is not directly added into the sample and the analysis of standard and analytes is conducted stepwise, this method may not meet the need of calibration of the air matrix's effects on the analysis of BTEX. This approach is also suitable to detected problems with fiber storage in filed devices, such as leaks, which will result in analyte and standard losses. Further development of the technology can include chemical immobilization of compounds, which will facilitate production of certified standards.

EXAMPLE 5

Electrophoresis in Non-Uniform Channel Modulated by Insert

Electrophoretic behavior of analyte in capillary consisted of two parts with different cross-section was investigated. The modulation of the separation path was achieved by inserting into the capillary a cylindrical fiber at different depth. The sample loaded at the end of lower cross-section and the appropriate zone, at it was demonstrated, spatially narrowed in the wide capillary part according to the electric field strength ratio in the two parts of the capillary. Additionally, the low conductive sample buffer can enhance the further signal narrowness and increase the total probe amount, introduced into the capillary by electroinjection. The applications of this concentration technique includes focusing after desorption from SPME fibers into the electrophoretic separation channel prior separation or prior to direct detection using for example UV-Visible, Fluorescence, electrochemical, NMR or mass spectrometry detection. Also, focusing of analytes present in a buffer is possible by inserting different shapes inserts prior to separation or direct detection. Periodic insertion of the insert into the channel will modulate the concentration of analyte, which facilitate separation and monitoring of the system connected to the separation channel. The modulation input could be random and the signal can be then analyzed by multiplex data processing techniques, such as cross-correlation. Modulation of the diameter of the channel can be also accomplished by applying external pressure or electrical pulses, which will also result in focusing without need for movement of the insert in and out of the channel. The results described below indicate that the focusing occur in a cross channel configuration since the channel cross-section diameter increasing substantially in the area where two channels meet. This can be used effectively to facilitate concentration of analyte prior to separation in the second channel, or in two-dimensional separation when the separation in the first channel is followed by focusing at the interface between the two channels prior to second dimension separation in the second channel.

Introduction. Non-constant form of a separation channel in electrophoresis is a way of providing the variance of some parameters (electric field strength, temperature, pH) which can play an important role for the process concerned. Smooth form changing is required should one need to obtain the appropriate smooth function. By varying a cross-section of electrophoretic camera one obtains an electric field gradient, this gradient can be used both in combination with some other force applied, what is used in so-called "gradient focusing techniques" or by itself provided the current density drop and the chamber design are appropriate to form sufficient temperature difference. The latter effect was used in IEF in thermogradients caused by internal Joule heating.

A separation channel, composed of few different parts but each one of constant form, can be used rather for sample introducing, detecting, multi step analysis development in microarray etc. The results described in this paper are also important for the methodologies where the sample application procedure is connected with a long object inserting (e.g. microfiber) into the separation capillary.

Experimental: Apparatus. The whole-column imaging detection (WCID) of UV absorbance was conducted in the iCE280 CIEF instrument (Convergent Bioscience Ltd., Toronto, Canada) with a fixed wavelength of 280 nm. A short fused-silica capillary (5.5 cm long) with an ID. of 100 um, internally coated with fluorocarbon (J&W Scientific, Folsom, Calif.), was assembled in a cartridge format (Convergent Bioscience Ltd.) The entire process of capillary conditioning, sample injection, data collection, and processing was implemented by a PC computer, and the electropherogram was recorded as absorbance versus the distance to the anode.

Materials and Chemicals. Optical fiber with a 50 and 61.5 um core (FHP050055065 & FVP60072082) was purchased from Polymicro Technologies Inc. (Phoenix, Ariz.). pI-markers and buffer chemicals were obtained from Bio-Rad. Water was purified using an ultrapure water system (Barnstead/Thermolyne, Dubuque, Iowa) and was used for all solutions.

Procedures. The fiber was inserted into the capillary at different distances and the capillary was filled with running buffer (Phosphate 5-100 mM, BioRad). Then, the sample was injected electokinetically, with the injection time being specially selected to achieve complete replenish of the first the first capillary part (containing an inserted microfiber). After, the electrode reservoirs were washed and the desired buffer was placed and the electrophoretic run performed.

Results and Discussion. The initial zone width is an important matter in CZE. For the case the sample concentration is insufficient to provide sensitive detection, a number of on-line preconcentration procedures is developed. The simplest electrophoresis-based techniques are connected with a special conductivity profile creation allowing us to achieve a higher electric field strength value in the sample zone place, although concentration mechanism may be different (e.g., CE- or ITF-based). The similar effect of electric field enhancing can be obtained due to stepwise cross-section change.

In these experiments, by inserting the cylindrical microfiber the cross-section of the separation channel was modulated. Sample was injected electrokinetically at 500v, the duration of voltage pulse was controlled to achieve complete filling of the first part of the capillary (up to the end of microfiber).

The initial starting zone was rather wide (taking into account the "dead" volume—around one half of the capillary). Then it was effectively compressed, in the same proportion as one could expect starting from cross section difference. In the case of two co-axial cylinders the cross-section ratio ($R=S_2/S_1$) is: $R=D^2/(D^2-d^2)$, where D is the diameter of the capillary and d is the one of the microfiber inserted. By the assumptions of constant conductivity, the electric field increase in the narrow part ($E_1/E_2$) is defined by $S_2/S_1$, and the initial zone length should be narrowed in the same proportion, approximately.

The effect of observed can be combined with methods traditionally used for sample preconcentration. With using low conductivity buffer it was possible to achieve an essential concentration sample increase in the plug introduced, although the peak width change was less evident.

This effect described above does not provide by itself any concentration increase in the introduced probe, since the volume of the sample zone should remain constant and the sample plug narrowing is due to it form change. But this simple and clearly visible effect still opens a lot of important applications to start with to start the separation from "initially wide" zone when it is necessary. For example, working with the inventive technique, one can insert a microfiber into the capillary and obtain a rather wide starting zone, with electric field application the initial zone can effectively be narrowed at the end of microfiber. The latter effect, obviously, depends on the relative size of microfiber inserted, and to achieve high zone narrowing the (D–d) difference should be small enough.

Solid phase microextraction and direct desorption of fluorescent labelled analytes into the separation channel was observed. The process is monitored by the fluorescence whole column imaging detection. The excitation light is delivered to the separation channel using the fiber. This work successfully demonstrates the stacking process that occurs in CE coupling interface with LIF imaging detection. Based on the enhancement in fluorescence intensity, concentration efficiency can be approximated to be as high as a 10-fold. Higher concentration efficiency could be expected with further optimization of configuration of the interface and the experimental conditions used, such as, dimensions of separation capillary and fiber, buffer concentration and applied voltage. The stacking effect generated by such an interface is beneficial to separation efficiency and detection sensitivity of CE separation.

EXAMPLE 6

Multi-Well Device for Performing Parallel SPME Operations

Multi-well devices, such as plates or trays may be used according to an embodiment of the invention. An embodiment of the invention is described below with reference to FIG. 28 to FIG. 38.

Figure 28:
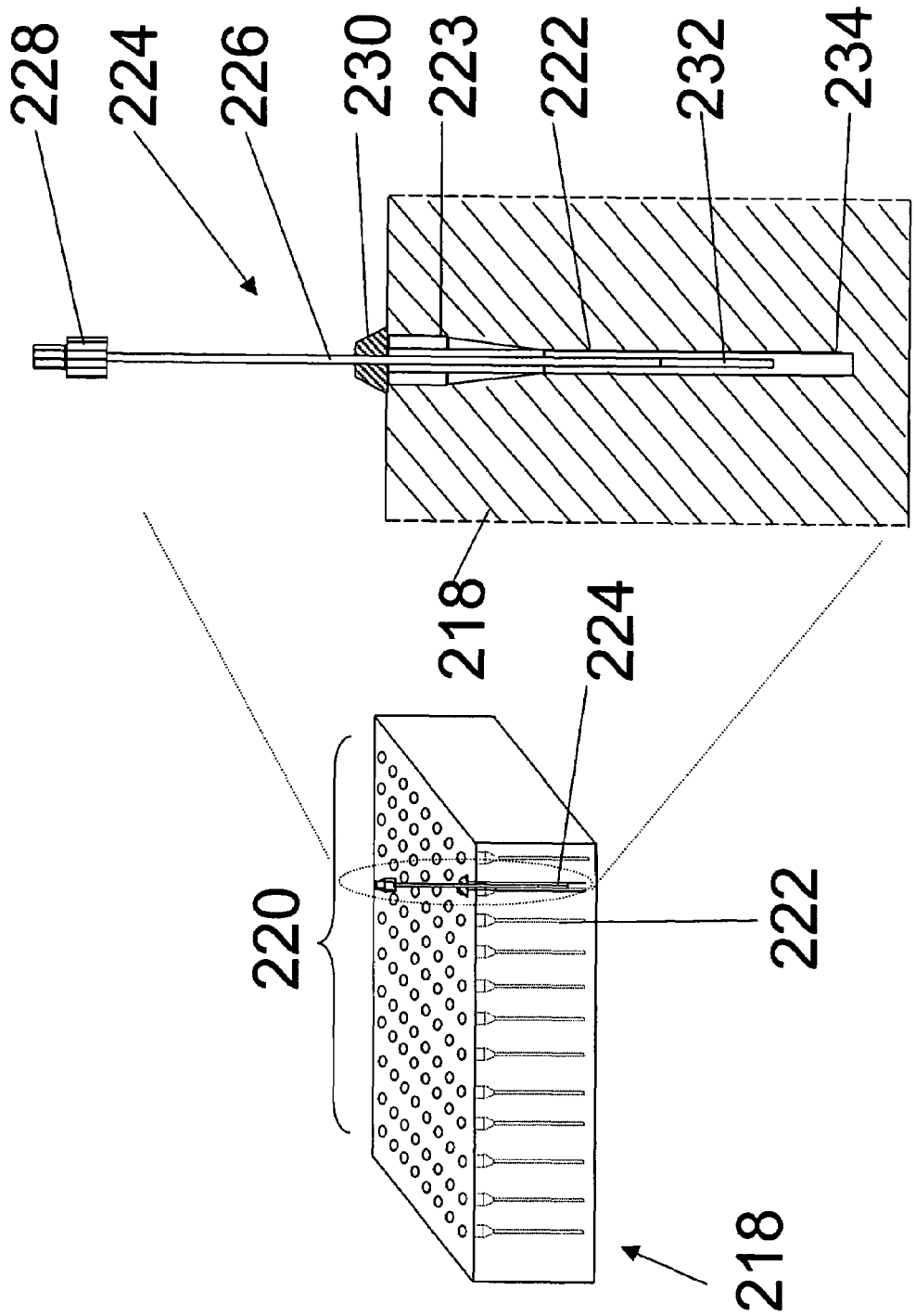
FIG. 28 shows a multiwell plate for performing parallel SPME fibre assemblies sealing operations.

FIG. 28 shows multiwell plate 218 having multiplicity of wells 220, each of the wells having the narrow part 222, which is able to seal needle 234 of the SPME fiber assembly 224. Each of the wells also possesses tapered guiding neck 223 in the upper portion of the well. The SPME module contains fiber 226 containing the coating 232 in the lower portion of the fiber located in the needle. The upper end of the fiber contains the attachment module 228, which can be used to operate the fiber assembly. The SPME fiber assembly also contains sealing septa 230, which seals the upper portion of the needle. As FIG. 28 indicates when the SPME fiber assemblies are placed inside wells of the multiwell plate, the coated part of the fibers are completely sealed in the needle and surrounded well. The sealing plate can be used after fiber has been exposed to investigated systems to prevent loss of analytes from the extraction phase. The plate can be placed in the robot to facilitate automated introduction of the fibers to the analytical instrument.

Figure 29:
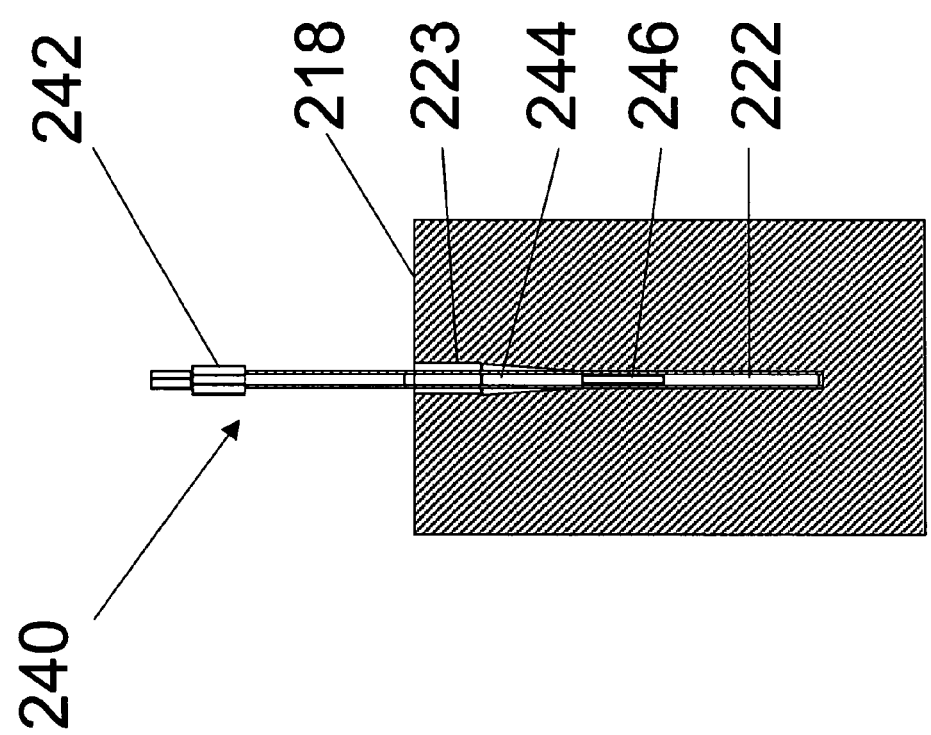
FIG. 29 shows a sealing application of a multiwell plate for internally coated needles according to an embodiment of the invention.

FIG. 29 shows application of the multiwell plate 218 of similar construction as in FIG. 28 sealing different version of SPME assembly 240 consisting of a needle 244 containing coating 246 in the needle. The upper portion of the needle is sealed with the attachment module 242.

Figure 30:
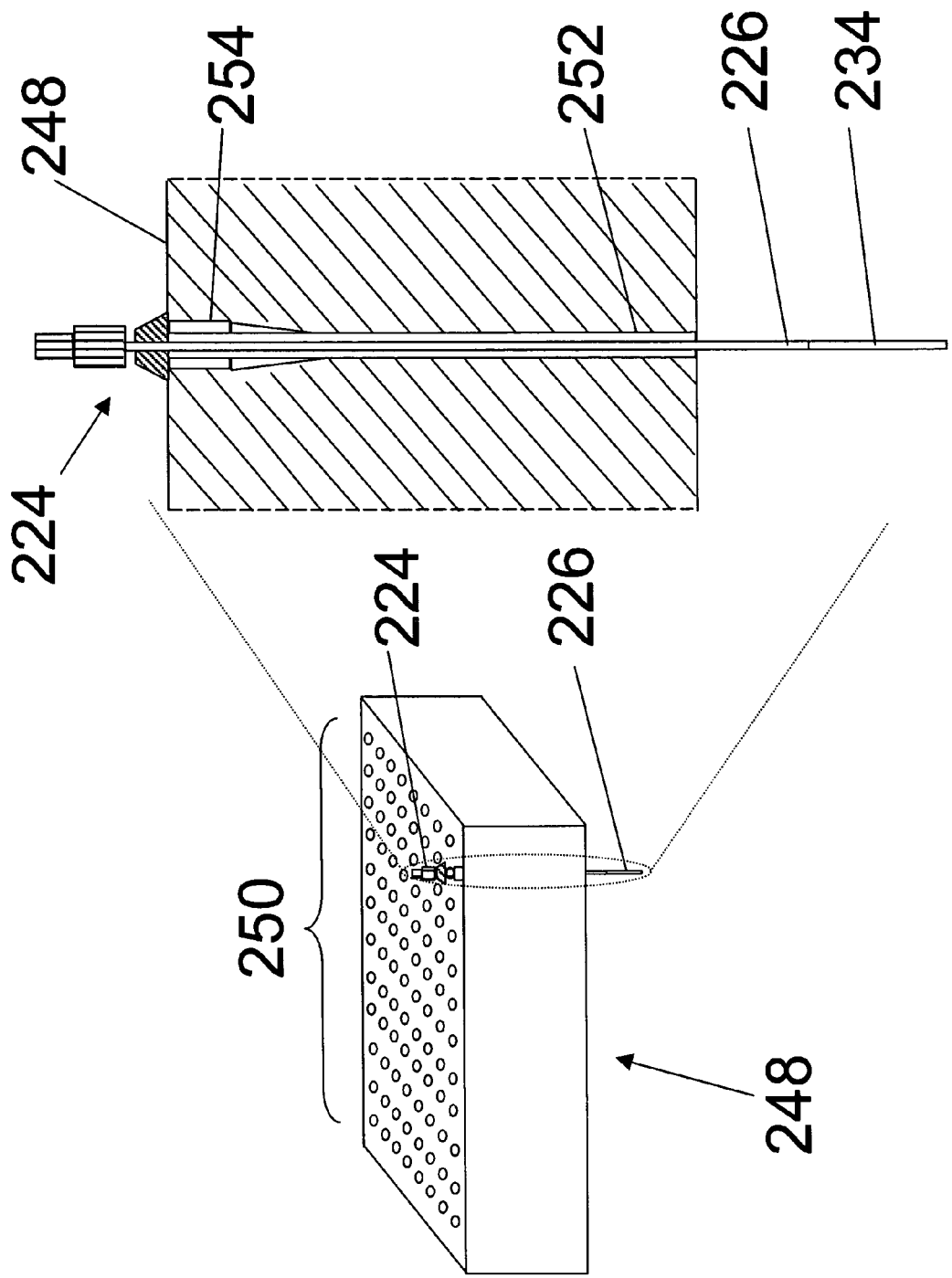
FIG. 30 shows a holding cover for a multiwell plate.

FIG. 30 illustrates holding cover 248 for the multiwell plates having multiple openings 250 consisting of a guiding portion 254 in the upper part of the well and lower portion 252 to position SPME fiber assemblies correctly with respect to multiwells containing samples. FIG. 30 illustrates the fiber exposed from the needle ready for placement in the well.

Figure 31:
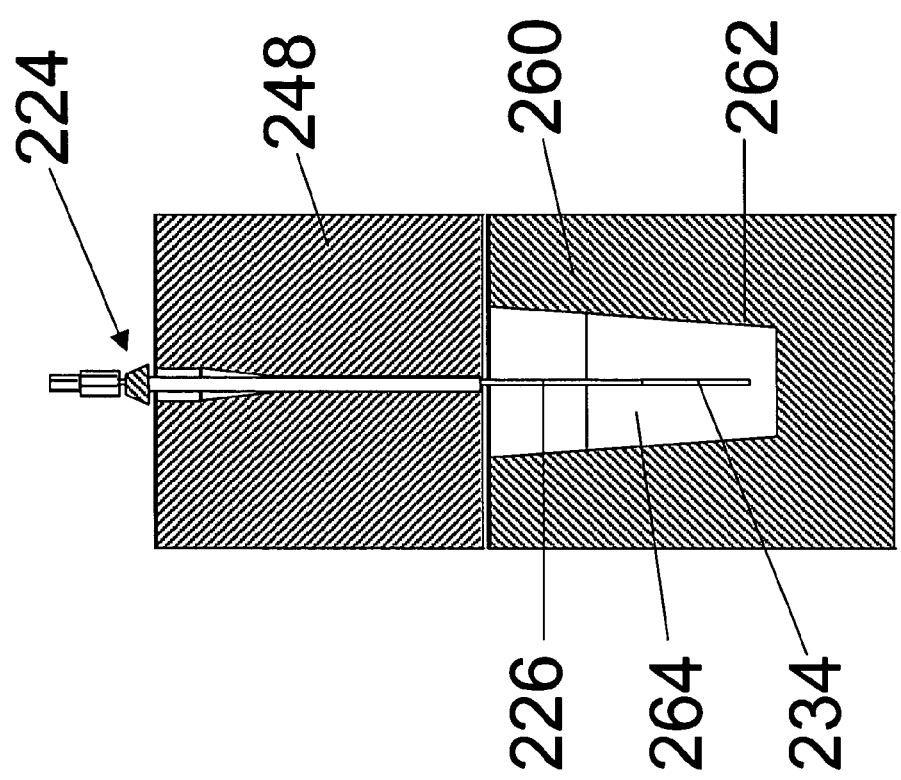
FIG. 31 shows an exposed fibre placed in a well of a multiwell plate.
Figure 32:
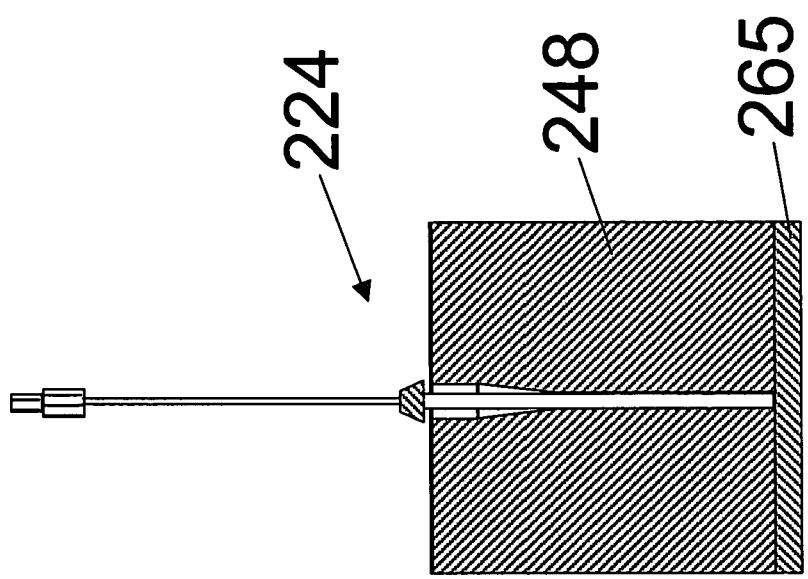
FIG. 32 shows a fibre retracted into a needle and sealed.

FIG. 31 shows the exposed fiber being placed in the well 262 of the multiwell plate 260 containing sample 264. After extraction the fibers containing analytes can be desorbed for determinations, or as FIG. 32 illustrates, the fiber 226 can be retracted into the needle located in the openings of the holding cover 248 and sealed by the sealing plate 265. In that arrangement the fibers are sealed in the holding plate. Then the sealed holing cover with the SPME devices can be transported to the multiwell plate containing desorption media and fibers can be desorbed by removing the sealing cover and lowering the fibers to the desorption media. The desorbed analytes can be determined by introducing the media containing analytes to analytical instrument. Alternatively the fibers can be desorbed directly into analytical instrument.

Figure 33:
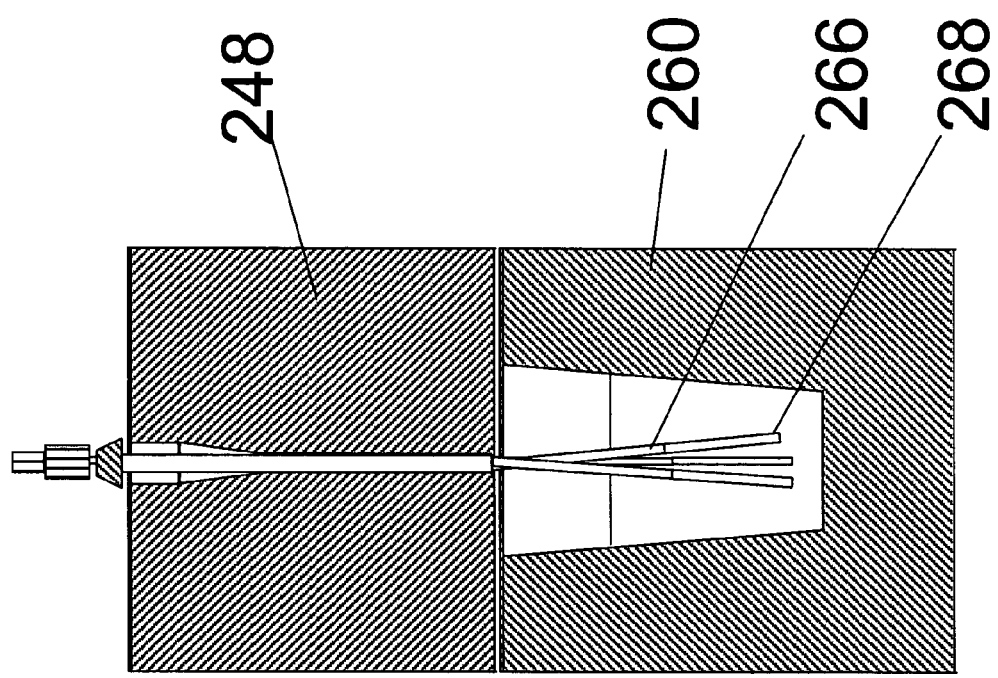
FIG. 33 shows a multi-fibre arrangement according to an embodiment of the invention.

FIG. 33 shows multi-fiber arrangement 266 containing coating 268, which can be used instead of a single fiber resulting in increased surface to volume ratio and faster extraction.

Figure 34:
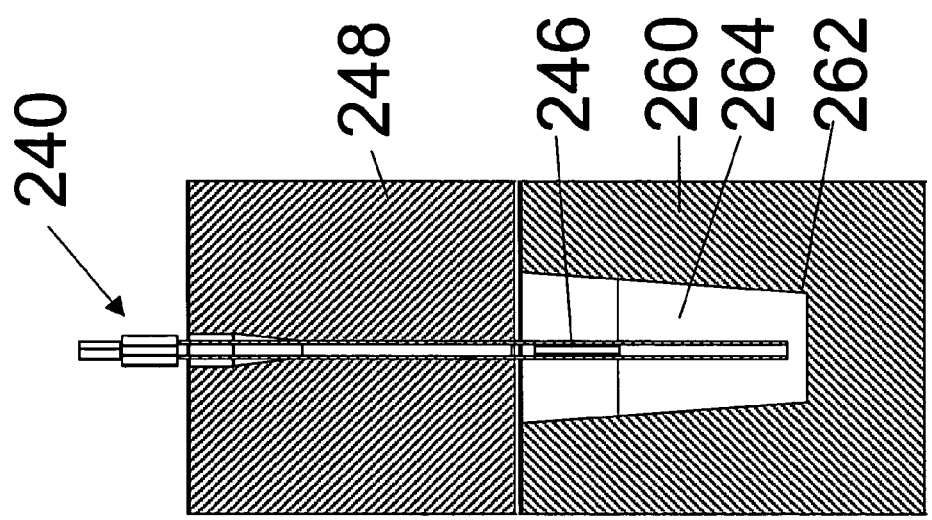
FIG. 34 shows a coated needle inserted in a well.
Figure 35:
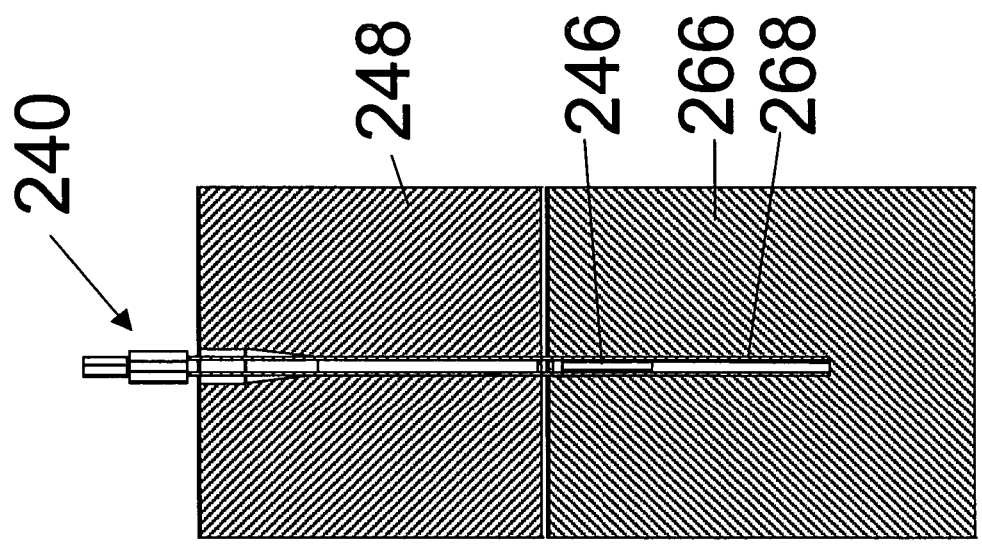
FIG. 35 shows a needle in a holding cover and a sealing plate

FIG. 34 and FIG. 35 illustrate operation of the holding cover and sealing cover for the SPME devices consisting of the coated needles. FIG. 34 illustrates the coated needle inserted in the well 262 of the multiwell plate 260. The sample can be drawn inside the needle 246 and ejected by applying differential pressure to the upper portion of the needle through the attachment module 242. FIG. 35 shows the application of the sealing plate 266 having sealing hole 268 to seal the SPME needle 246. The SPME needles can then be transported to analytical instrument for desorption or desorbed in the wells prior to determinations.

Figure 36:
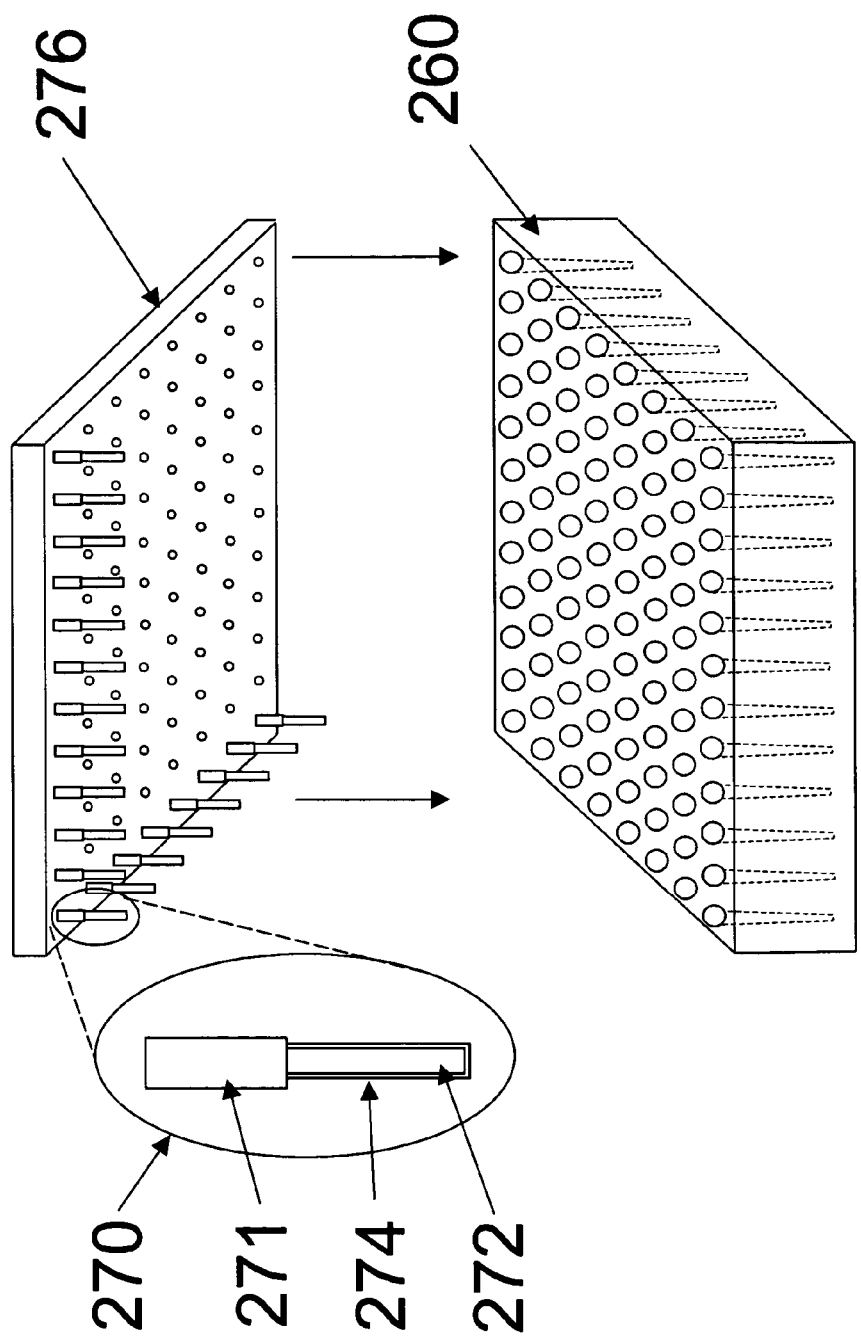
FIG. 36 shows a multiwell plate extraction arrangement.
Figure 37:
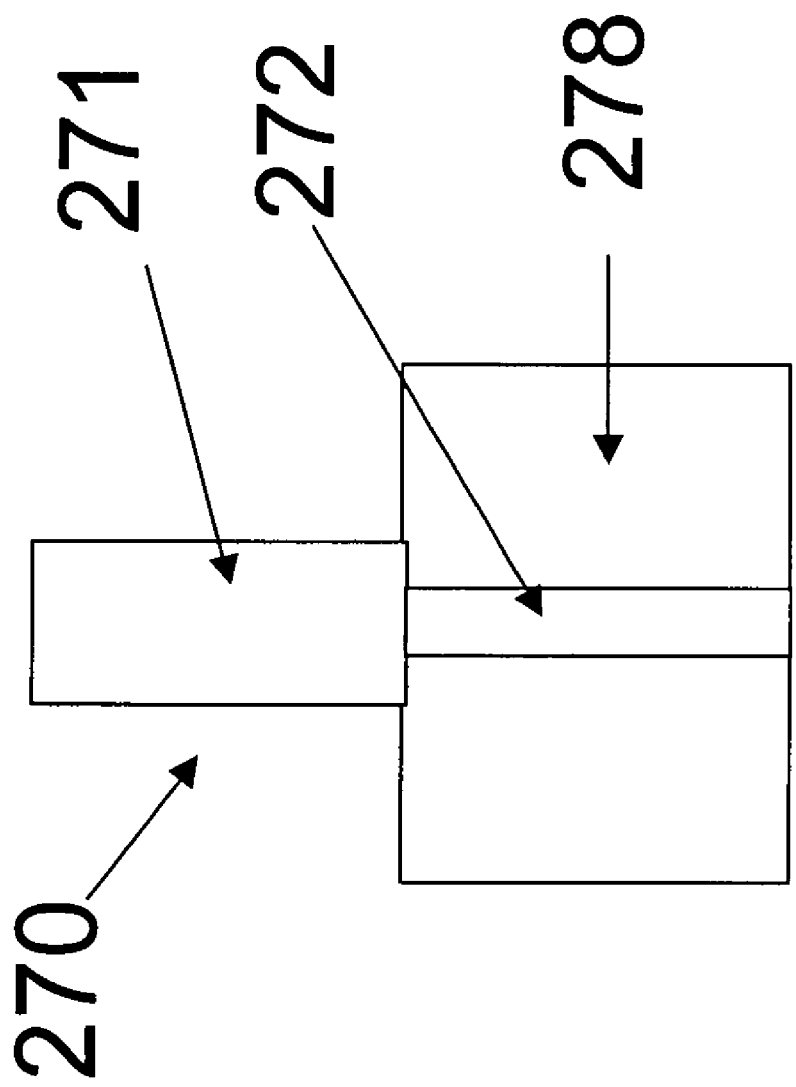
FIG. 37 shows a fibre having a fin attached thereto.

FIG. 36 illustrates alternative SPME multiwell plate extraction arrangement, where coated fibres are directly attached onto the mounting plate 276 which fits directly into the multiwell plate 260. The fibre 270 used in such arrangement typically consists of mounting head 271 and lower portion 272 coated by the extraction phase 274. The extraction phase can be in a form of a flat thin membrane 278 in a form of a "fin" attached to the lower portion of the fibre as FIG. 37 indicates. This high surface to volume arrangement facilitates rapid extraction rate and better agitation resulting in shorter extraction times. In some cases only tip of the fibres can be coated, if after extraction the fibres are desorbed into analytical instrument using MALDI process.

FIG. 38 illustrates part of the cover plate 284 containing multiple fibers used as a MALDI target after extraction process is completed. The laser light 286 irradiates the tips of the fibers 280 where the coating 282 is located facilitating introduction of analytes through orifice 288 to analytical instrument 290, such as mass spectrometer. After extraction and before MALDI introduction MALDI matrix can be added to the coating to facilitate better desorption efficiency.

During extraction and desorption agitation is applied to accelerate the mass transfer. The agitation approached which can be used includes magnetic stirring, sonication, shaking and vortex agitation.

Two exemplary approaches in handling desorption of the fibers in the wells are direct desorb and plate drying.

Direct Desorb. The direct desorb approach involves using a low volume narrow well containing desorption solvent. Subsequently, most of the solvent is introduced to the analytical instrument. For example, dispensation of about 20 microlitres of desrob solution into each well is then be followed by exposing a probe into each well for about 30 seconds or less. Following desorption, about 10 to 15 microlitres of the solution may be injected into the analytical instrument. Direct desorption may be used for volatile or thermally unstable analytes. However, the probe must be desorbed directly into the injection solution appropriate for the analytical instrument, for example 75% MeOH.

Plate Drying. The plate drying approach may use conventional large volume wells (for example, 0.5-1.0 mL) and a well drier. After desorption of the probe into solvent, the solvent is evaporated and a small amount of appropriate mobile phase is added to reconstitute (dissolve) analytes prior to injection into an analytical instrument. In this way, the analytes can become more concentrated. For example, dispensation of 0.55 mL of desorb solution into each well is then followed by exposing a probe into each well for about 30 seconds or less. The wells are evaporated to dryness for about 30 minutes, followed by reconstitution with 30 to 40 microlitres of an appropriate solvent. Subsequently, 10 to 15 microlitres of the reconstituted solution can be injected into an analytical instrument. An advantage of the plate drying approach is that more compatible solvent system can be used as the analysis required, for example the probe can be desorbed into methanol and reconstituted in an optimal injection solution appropriate for the analysis method. However this approach requires driers, which can add to the expense. Additionally, if analytes of interest are thermally unstable or volatile, some loss of analyte must be taken into account.

Advantageously, multi-well plates can be used to accommodate high throughput screening in SPME technology. Similar approach can be used in liquid phase microextraction.

EXAMPLE 7

Equilibrium In-Fibre Standardisation Technique for Solid-Phase Microextraction

This example describes an exemplary solid phase microextraction using a standard loaded into the fibre coating as a means of internal standardisation for the analysis of samples contained in vials. Reproducible amounts of standards were loaded into a SPME non-porous fiber. It was found that spiking a few microliters of liquid standards such as benzene, toluene, ethylbenzene, and xylenes (BTEX) and/or adding a few milligrams of solid standards such as naphthalene into few grams of pump oil sealed in a 20 milliliter vial provided an excellent standard generator, and allowed for reproducible loading of standards (RSD<4%) up to hundreds of times. When standards were introduced into a sample vial together with a fiber, extraction of analytes into the fiber and desorption of the standards into the sample matrix occured simultaneously. Quantification was then based on the equilibrium distribution of the standards and the analytes between the fibre coating and the sample matrix in the vial. A comparison of equilibration profiles obtained using traditional internal standardisation and the in-fibre approach generally showed the same equilibration behaviour. This method, according to one aspect of the invention was successfully used to correct for matrix effects in the BTEX analysis of a wine sample.

Introduction. Internal standardisation is a well known calibration approach in analytical chemistry that is used to improve the accuracy and precision of experimental data to account for such factors as sample matrix effects, losses during sample preparation, and irreproducibility in such parameters as sample injection in GC (Haefelfinger, Chromatogr, 1981, 218, 73-81). Solid-phase microextraction (SPME) as a sample preparation and extraction technique is no exception, with internal standardisation often used for quantification particularly when analysing complex samples. However, the addition of an internal standard provides an additional step in sample preparation. For completely automated analysis, two robotic arms are required, one to provide the standard spike and the other for SPME. There are also situations in which the addition of an internal standard is not practical, such as on-site or in-vivo applications.

SPME is a solvent free technique designed for rapid sampling and sample preparation. (Pawliszyn, J. Solid Phase Microextraction Theory and Practice; Wiley-VCH: Chicester, 1997; Chen et al, J. Analyst, 2004, 129, Advance Article). The most common form of the technique uses a fibre coated with a liquid polymeric film, which is exposed to the sample, extracting analytes from it until equilibrium is reached. The amount of analyte absorbed by the coating at equilibrium ($n_f$) is linearly proportional to the initial concentration in the sample ($C_0$) by eq 6 (Chen et al., J. Analyst, 2004, 129, Advance Article.):

$$n_f = \frac{K_{fs} V_f V_s}{K_{fs} V_f + V_s} C_0 \qquad (6)$$

where $K_{fs}$ is the fibre/sample distribution coefficient, $V_f$ is the volume of the fibre coating and $V_s$ is the volume of the sample. For analysis in a vial containing headspace this equation should be expressed as shown in eq 7 (Chen et al., J. Analyst, 2004, 129, Advance Article):

$$n_f = \frac{K_{fs} V_f V_s}{K_{fs} V_f + K_{hs} V_h + V_s} C_0 \qquad (7)$$

where $K_{hs}$ and $V_h$ represent the headspace/sample distribution coefficient and the volume of the headspace, respectively.

The fact that SPME is an equilibrium rather than an exhaustive extraction technique means that even after the extraction process has been completed a substantial portion of the analytes usually remain in the matrix. This presents an opportunity for quantification based on internal standardisation, namely that the standard is loaded onto the fibre prior to the extraction step, instead of spiked into the sample. Chen and Pawliszyn (Chen et al., J. Analyst, 2004, 129, Advance Article; Chen and Pawliszyn, Anal. Chem. 2004, 76 (19): 5807-5815 entitled "Kinetics and the On-Site Application of Standards on A SPME Fiber") have recently explored the kinetics of the technique, demonstrating that the absorption and desorption processes are isotropic, which allows for calibration of the rate of absorption using the rate of desorption.

The current example aimed to expand on this technique to fundamentally assess the in-fibre standardisation approach with systems reaching equilibrium. The in-fibre standardisation approach was developed for automated sampling from millilitre quantities of liquids in vials and used for the analysis of BTEX in a wine sample.

Theoretical Considerations. The equilibrium equation for SPME, most generally described by eq 7 is derived from the knowledge that the amount of analyte in the system will remain the same before and after the extraction. This mass balance equation can therefore be expressed by eq 8:

$$n_T = n_f + n_h + n_s \qquad (8)$$

where $n_T$ is the total number of moles of analyte in the system, and the remaining terms denote the amount of the analyte in the fibre, headspace and sample respectively at equilibrium. Using this form of expressing the mass balance, leads to eq 9:

$$n_f = \frac{K_{fs}V_f}{K_{fs}V_f + K_{hs}V_h + V_s}n_T \quad (9)$$

From this equation, it is apparent that no matter where the standard or analyte of interest starts in the system, at equilibrium the amount in the fiber should be the same.

A further consideration is the kinetics of the process. For traditional SPME the kinetics for both direct and headspace extraction can be described by eq 10 (Ai, J. Anal. Chem. 1997, 69, 3260-3266; Ai, J. Anal. Chem. 1997, 69, 1230-1236):

$$\frac{n}{n_f} = 1 - \exp(-at) \quad (10)$$

where n is the moles of analyte in the coating at time t, a is a constant that is dependant on the volumes of the fibre, headspace and sample, mass transfer coefficients, distribution coefficients and the surface area of the fibre. The kinetic processes involved for desorption of analytes from the fibre coating is defined by eq 11:

$$q = n_0 \frac{V_s}{K_{fs}V_f + V_s}[1 - \exp(-at)] \quad (11)$$

where q is the moles of the analyte lost from the coating at time t and $n_0$ represents the moles of the compound originally loaded. For the case of in-vial analysis the moles remaining on the fibre (n) at time t can be expressed as $$n = n_0 - q \quad (12)$$

From eqs 11 and 12 it is apparent that $$n = n_0 - n_0 \frac{V_s}{K_{fs}V_f + V_s} + n_0 \frac{V_s}{K_{fs}V_f + V_s}\exp(-at) \quad (13)$$

However, as the exponential term disappears as time goes to infinity, therefore $$n_f = n_0 - n_0 \frac{V_s}{K_{fs}V_f + V_s} \quad (14)$$

Substituting eq 14 into eq 13 and rearranging gives $$\frac{n - n_f}{n_0 - n_f} = \exp(-at) \quad (15)$$

Comparing eq 15 with eq 10, it can be concluded that for in-vial analysis the isotropy of absorption and desorption of an analyte from the fibre still maintains. A similar expression can be derived for headspace analysis with a suitable adjustment in the definition of a.

Experimental: Materials. Ethylbenzene-$d_{10}$ (99+%), ethyl benzene, o-xylene (98%, HPLC grade), naphthalene (99+%, scintillation grade) and carbon disulfide (99.9+%, HPLC grade) were purchased from Sigma-Aldrich (Milwaukee, Wis., USA). Benzene (analytical reagent) was from BDH Inc. (Toronto, ON, Canada), toluene (Guaranteed Reagent) from EMD (Gibbstown, N.J., USA), $D_8$-Naphthalene (99%) from Cambridge Isotope Laboratories Inc. (Andover, Mass., USA). HPLC grade methanol was obtained from Fisher Scientific (Nepean, ON, Canada), the vacuum pump oil was supplied by BOC Edwards (Wilmington, Mass., USA), and the poly(dimethylsiloxane) (PDMS) membrane material was supplied by Specialty Silicone Products Inc. (Ballston Spa, N.Y., USA). PDMS (100 μm) SPME fibres and Tenax (TA80/100 mesh) were purchased from Supelco (Bellefonte, Pa., USA). Water purified from a Barnstead ultrapure water system (Dubuque, Iowa USA) was used throughout. All gases were supplied by Praxair (Kitchener, ON, Canada) and were of ultra high purity. Ten or twenty millilitre sample vials were used for automated analysis with magnetic crimp caps and PTFE coated silicone septa (Microliter Analytical Supplies, Suwanee, Ga., USA). The dry white wine sample was obtained from a local liquor store.

GC Analysis. Gas chromatography was performed on a Varian™ (Mississauga, ON, Canada) 3800 gas chromatograph coupled with a Saturn™ 2000 MS system controlled by computer using Varian Saturn Workstation software (ver. 5.51) or with a FID detector using Star Chromatography Workstation (ver 5.51). Automated analysis was performed using a CTC CombiPal™ autosampler (Zwingen, Switzerland) using the associated Cycle Composer™ software (ver 1.4.0). The PAL was equipped with a SPME fibre holder, a temperature controlled six vial agitator tray and a fibre conditioning device. Separation was performed using a 30 m×0.25 μm×0.25 mm I.D. Rtx-5MS fused silica column from Restek (Bellefonte, Pa., USA). For analysis of BTEX the column was initially set at 40° C. for 4 minutes and then ramped at 15° C./min to 130° C. giving a total run time of 10 minutes. The injector was set at a temperature of 250° C. and helium was used as the carrier gas at a flow rate of 1 mL/min. For analysis of naphthalene, the column was initially set at 40° C. for 1 min and then ramped at 20° C./min to 220° C. giving a total run time of 10 min. The temperature of the injector was set at 250° C. and helium was used as the carrier gas at a constant pressure of 12 psi. For both analytes a 1 minute desorption time in the GC injection port was used, which was immediately followed by a 2 minute bake-out at 250° C. in the autosampler fibre conditioning device.

FID was used at a temperature of 300° C. with gas flows for hydrogen, high purity air and make-up gas (nitrogen) set at 300, 30 and 25 ml/min respectively. For the mass spectrometry detection experiments, electric ionisation was used with temperatures of 170, 50 and 260° C. for the trap, manifold and transfer line respectively. A scan range of 70 to 125 m/z was used and quantification was performed using 78 m/z for benzene, 91 for toluene, 98 and 116 for deuterated ethyl benzene and 91 and 106 for ethyl benzene and o-xylene. For naphthalene, a scan range of 100 to 160 m/z was used and quantification was performed using 128 m/z for naphthalene and 136 nm/z for deuterated naphthalene.

For the automated analysis a sampling temperature of 35° C. was used. The internal standard was loaded onto the fibre by exposure to the headspace of a 20 mL sample vial containing 4.00 g of vacuum pump oil spiked with deuterated ethyl benzene at a concentration of 0.47 mg/g. The loading time was 1 minute with an agitation speed of 500 rpm. The fibre was then immediately exposed to the headspace of a 10 mL vial containing the sample for 5 minutes, again using a 500 rpm agitation speed. The sample volume used unless otherwise specified in these experiments was 3.0 mL. A 6 minute pre-extraction equilibration of the sample was performed in the agitation unit at 500 rpm. For loading of naphthalene, a 2.00 g solution pump oil was used containing 2.0 mg/g naphthalene. All other conditions were the same as in the ethyl benzene experiments unless otherwise specified.

Addition of Standard Spike to Vials. Standards used for constructing calibration curves and sample "spikes" to test the method were prepared by spiking the sample with a standard of the target compounds prepared in methanol. Initially this was done after the vial had been capped by means of a 10 or 100 μL syringe. However, using this approach a steady decline in peak areas for the analytes was observed that was related to the amount of time between spiking and sampling. The decline was worse with ethyl benzene and xylene than with benzene and toluene. This suggested the behaviour was caused by absorption of the compounds into the small part of the vial septum silicone layer exposed through addition of the standard spike. To overcome this difficulty it was necessary to spike the solutions prior to capping. To minimise evaporation it was necessary to add the spike below the level of the solution in the vial, a similar approach to that adopted for standard preparation in EPA method 5021A (US Environmental Protection Agency, Method 5021A: Volatile Organic Compounds in Various Sample Matrices Using Equilibrium Headspace Analysis, 2003).

Results and Discussion: Internal Standard Loading on Fiber. The first challenge was to find a method that would allow, automated, fast and reproducible loading of the standard into the fiber. Development of an appropriate method was performed using ethyl benzene as the "standard" for loading. Sampling from the headspace of a vial containing pure ethyl benzene resulted in unmanageably high loading on the fiber coating even for extremely short absorption times. This was true even when cooled to 5° C. in the sample tray. The use of diluted solutions of ethyl benzene in water to reduce the loading to an acceptable level showed that the mass of ethyl benzene withdrawn from the vial during each loading step was a significant percentage of the total. This made it impossible to reuse a "loading" vial, which is not practical in terms of the number of standard solution vials required for a automated sample list. The use of alternative techniques, such as vials containing ethyl benzene absorbed onto Tenax, or PDMS membrane showed similar problems. Injecting the needle into a headspace of a vial containing pure ethyl benzene, but not exposing the fiber coating showed a workable and reproducible loading, except the needle sometimes being blocked with a piece of septum.

Finally, a system was adopted whereby the ethyl benzene was dissolved in vacuum pump oil, to reduce the $K_{fs}$ partition coefficient for the standard into the fiber. Using this method gave an acceptable and reproducible loading with 1 min exposure to the standard solution headspace. This also worked well for naphthalene. The amount loaded into the fiber can be further adjusted by spiking different amount of the standard into the vacuum pump oil and/or exposing the fiber for different time. Using this approach, each loading cycle only withdrew 0.0087% of the ethyl benzene in the vial, making it possible to use the vial for at least 115 injections before 1% of the vial contents had been removed. Reproducibility of the loading step for ethyl benzene determined by FID was 1.9% for 40 injection cycles, whilst the value was 2.6% for loading followed by equilibration with a vial containing 3 mL of water for 10 minutes in 20 injection cycles. For naphthalene loading reproducibility was 2.0% for 30 injection cycles, whilst the value was 3.6% for loading followed by equilibration with a vial containing 3 mL water for 10 min in 20 injection cycles. In theory, the standard solution can be used at least 300 times before 1% of the vial contents had been removed.

Figure 39:
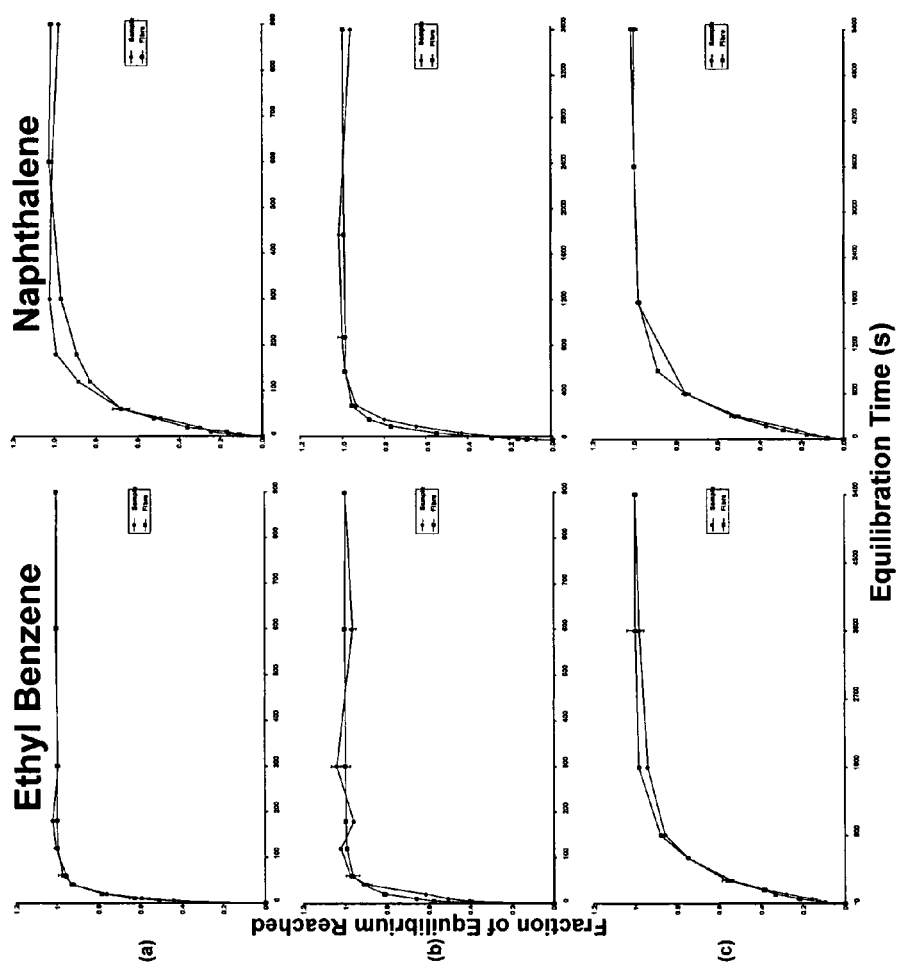
FIG. 39 shows a comparison of SPME equilibration profiles.

Comparison of Equilibration Curves. As a first investigation of the approach, equilibration profiles using traditional SPME and in-fiber standardisation SPME for ethyl benzene and naphthalene were compared when exposed to empty 10 mL headspace vials, (actual volume was determined to be 11.5 mL). The two processes were also investigated using direct immersion of the fiber in vials filled with water and headspace experiments in vials containing 3 mL of water. The results are shown in FIG. 39, with the profiles from the two approaches normalized according to eqs 10 and 15 respectively. Under the conditions studied the equilibration time was not influenced by the location of the standard at the beginning of the equilibration process.

FIG. 39 provides a comparison of SPME equilibration profiles with the analyte added directly to the sample vial and via the fiber coating using ethyl benzene and naphthalene as the test compounds. The graphs show profiles using (a) empty vials, (b) headspace analysis, and (c) direct immersion into vials full of water. Agitation speed was set at 500 rpm for all cases. For other conditions see text.

Applications to Real Sample Matrices. To test the in-fibre standardisation method, the technique was used to examine BTEX in spiked white wine with MS detection. The method was linear for BTEX compounds over the tested range of 0.09-73 μg/L. For all of the compounds, the linearity was higher than 0.9998 in both the calibration curves and the curves normalized by internal standard. The recoveries from wine spiked with 7.3 μg/L BTEX, calculated using external calibration and the in-fibre standardisation approach are given in Table 2. Deuterated ethyl benzene was used as the internal standard.

TABLE 2

Recoveries for BTEX in White Wine

| Compound | Recovery calculated using external calibration (%) | Recovery calculated using internal standard in the fibre (%) |
|---|---|---|
| Benzene | 81.2 ± 5.2 | 102.3 ± 5.8 |
| Toluene | 83.2 ± 0.7 | 105.1 ± 0.2 |
| Ethyl Benzene | 76.8 ± 1.0 | 99.3 ± 0.6 |
| o-Xylene | 72.1 ± 1.5 | 91.2 ± 1.3 |

It was demonstrated that the in-fibre technique gives improved recovery for the determination of these compounds than seen using external calibration. With $d_{10}$-ethylbenzene as internal standard, 99% recovery was obtained for ethylbenzene. The slightly higher deviations from 100% recovery for the other analytes can largely be attributed to differences in the interactions of these compounds with the matrix compared to the internal standard.

Conclusions. From this example, it is confirmed that the in-fibre standardisation approach works successfully under equilibrium conditions and can be easily automated. The developed procedure requires only a single arm autosampler, unlike SPME with traditional internal standardisation that requires a dual arm system. Equilibration time was not affected by where the standard commenced in the system. The technique was applied to the analysis of BTEX in wine, successfully correcting for matrix effects. This method can also be used with other equilibration extraction techniques, such as liquid phase microextraction (LPME) or membrane extraction.

EXAMPLE 8

Standards in Liquid Phase for Liquid-Phase Microextraction

This example describes the application of hollow fiber assisted liquid phase microextraction in the sample preparation with selected polycyclic aromatic hydrocarbons (PAHs) and chlorinated compounds as target analytes. 1-Octanol was used as organic solvent with $d_{10}$-fluoranthene added as internal standard. The Celgard™ hollow fiber gives higher enrichment factor than Accurel™ hollow fiber, while a longer equilibration time was needed. The internal standard concentration in Accurel™ hollow fiber decreased with equilibration, while that in Celgard™ hollow fiber changed little in the experimental uncertainty. The extraction process of analytes in aqueous phase and the back extraction behavior of internal standard in 1-octanol were found to be different.

Introduction. A new sample preparation technique called liquid phase microextraction (LPME) was introduced and reviewed recently (Rasmussen et al., Trends in Analytical Chemistry, 2004, 23, 1). The LPME technique has the possibility of tuning the selectivity of the extraction by chemical means just like liquid-liquid extraction (LLE), while has the advantage of effectively reducing the consumption of organic solvent. In order to increase the robustness and possibility of automation, a polymer membrane (either flat sheet membrane (Hauser and Popp, J. Sep. Sci., 2001, 24, 551) or hollow fiber (Ho et al., Journal of Chromatography A, 2002, 963, 3; Shen et al., Anal. Chem., 2002, 74, 648; Halvorsenet al., Journal of Chromatography B, 2001, 760, 219) was used in LPME.

Up to now, highly hydrophobic polymers such as polypropylene or polyethylene were used as membrane materials. Compared to the solid phase micro-extraction (SPME), the membrane in LPME acts as a filter to prevent the contamination from dirty sample matrix. Several ways of experimental setup have been developed. Obviously, the polymer material itself and its morphology have tremendous effects on the extraction process. In this example, two microporous hollow fibers of polypropylene and cellulose acetate with different dimensions and morphology were studied in the application of LPME. The internal standardization is widely used to increase the reliability of the measurement and a new approach to SPME calibration has been described with internal standard added in extraction phase before the sampling. In this publication, the internal standardisation was firstly studied by adding the internal standard in the organic extraction phase before the start of liquid phase microextraction.

Experimental. Materials and Reagents. Anthrane, fluoranthene, $d_{10}$-fluoranthene, and 5 mL screw cap vials were ordered from Supelco (Bellefonte, Pa., USA). Trichlorophenol, pentachlorobenzene, and 1-octanol were purchased from Sigma-Aldrich (Milwaukee, Wis., USA). HPLC grade methanol was from Fisher Scientific (Nepean, ON, Canada). The hollow fibres were from Membrana GmbH (Germany) and Hoechst (Germany) respectively. Water purified from a Barnstead ultrapure water system (Dubuque, Iowa USA) was used throughout. All gases were supplied by Praxair (Kitchener, ON, Canada) and were of ultra high purity.

Instrument Condition. Gas chromatography was performed on a Varian (Mississauga, ON, Canada) 3800 gas chromatograph coupled with a Saturn 2000 MS system controlled by computer using Varian Saturn Workstation software (ver. 5.51). The oven was kept at 40° C. for 1 min and then increased to 280° C. at 10° C./min and then kept for 3 min. The total run time was 28 min at a constant pressure of 12 psi with helium as the carrier gas. The injector temperature was set at 280° C. For the mass spectrometry detection, electric ionisation was used with temperatures of 170, 50 and 260° C. for the trap, manifold and transfer line respectively. A scan range of 100 to 270 m/z was used and quantification was performed using 198+132 m/z for trichlorophenol, 250 for pentachlorobenzene, 178 for anthrane, 212 for $d_{10}$-fluoranthene, and 202 for fluoranthene.

Sample Preparation and Data Processing. Methanol solution (60 mg/L) of selected analytes (trichlorophenol, pentachlorobenzene, anthrane, fluoranthene) was made and 5 μL such solution was spiked in 4 mL water in 4 mL vial, which was used as the sample solution. 1-Octanol was used as the acceptor organic solvent. One Celgard microporous hollow fiber (Hoechst) with pore size 0.03 μm, porosity 30%, wall thickness 28.8 μm and O.D. 440 μm and one Accurel PP Q3/1 hollow fiber (Membrana GmbH) with wall thickness 200 μm and O.D. 1000 μm were used. They were cut to 3 cm length and washed in methanol for 5 min by sonication. The dry fiber was then dipped in 1-octanol for 5 min by sonication. The 1-octanol immobilized fibre was then placed in the sample solution with one end connected to the tip of 10/100 uL syringe, which was stirred at a rate of 750 rpm. For internal standardization, $d_{10}$-fluoranthene was added to 1-octanol at 100 mg/L. The enriched sample in the lumen of hollow fiber was taken into the syringe and then injected in injector 1079 of GC/MS. The Accurel hollow fiber contains about 18.5 μL organic solvent in total and 8.5 μL in the lumen. The Celgard hollow fiber contains about 3.8 μL organic solvent in total and 3.4 μL in the lumen.

An exemplary set-up for hollow fibre assisted liquid phase microextraction includes a syringe contacting a porous hollow fibre suspended in a container, such as a beaker. The beaker contains an aqueous sample (a donor solution). Within the lumen of the porous hollow fibre, an organic solvent (an acceptor solution) is located. A stir bar is provided at the bottom of the beaker, which may be placed on a magnetic stirrer.

Results and Discussion. Basic Principle. During the membrane-assisted solvent extraction, the hydrophobic, organic compounds are extracted via the wall of porous hollow fiber to the organic solvent in the lumen. A two-phase system with 1-octanol as acceptor phase was used. 75 μg/L Aqueous solution was used as donor phase. According to the mass balance relationship, the total recovery R is defined as eq 16:

$$R = \frac{100KV_a}{KV_a + V_d} \tag{16}$$

$V_a$ is the total volume of acceptor solution including that in the pores of hollow fiber wall, and $V_d$ is the volume of donor solution. K is the ratio of analyte concentration in the two phases.

Because the organic solvent exists in the pores of the hollow fiber and some in the lumen cannot be transferred into the instrument, the true recovery R' is defined as eq 17:

$$R' = \frac{100KV'_a}{KV_a + V_d} \quad (17)$$

$V_a'$ is the volume of acceptor solution injected into the instruments. It should be pointed out that the high porosity (high percentage of organic solvent immobilized in the wall) increases the diffusion rate of analytes, while decrease the true recovery of the experiments. The enrichment factor is defined as eq 18:

$$E = \frac{C_a}{C_{d,initial}} = \frac{V_d R}{100 V_a} \quad (18)$$

$C_a$ and $C_{d,initial}$ is the analyte concentration in acceptor solvent and the initial analyte concentration in donor solution.

Theory. Consideration of Fiber Dimensions on the True Recovery. The conditions for extraction can be optimized according to above equations. As can be seen, the organic solvent volume ($V_a-V_a'$) left in the wall of the fiber should be as small as possible in order to increase the analyte recovery. This can be done by decreasing the porosity and the thickness of the fibre wall. Increasing the total volume $V_a$ can also increase the recovery. Figure II-2 is a simulation result of recovery vs. total volume $V_a$ with parameters of K=120, $V_d$=4 mL, $V_a/V_a'$=1, 1.2, 1.4, 1.7, 2.2, 3 respectively.

Figure 40:
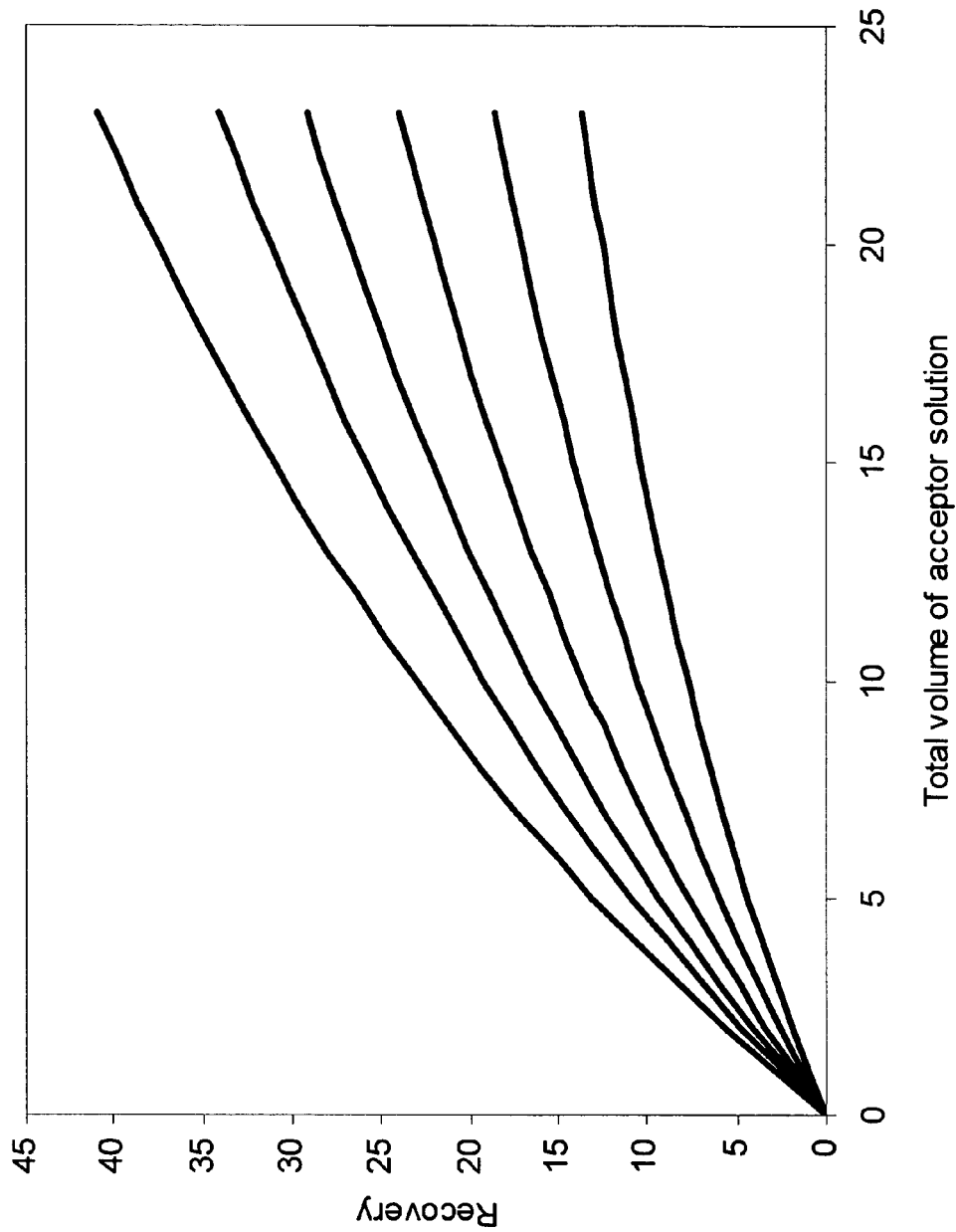
FIG. 40 simulates true recovery vs total volume of acceptor solvent.

FIG. 40 illustrates a simulation result of true recovery vs total volume of acceptor solvent. This figure shows that with the same total volume of organic solvent, the true recovery decreases with increasing the percentage of organic solvent immobilized in the wall of hollow fiber.

Effects of Changing Hollow Fibers. The Accurel and Celgard hollow fibres are different considerably both in dimensions and porosity. Compared to Accurel hollow fiber, Celgard hollow fiber has much lower wall thickness and porosity (i.e. $V_d/V_a'$ is close to 1). The enrichment factor as a function of extraction time was evaluated for the two fibers.

Figure 41:
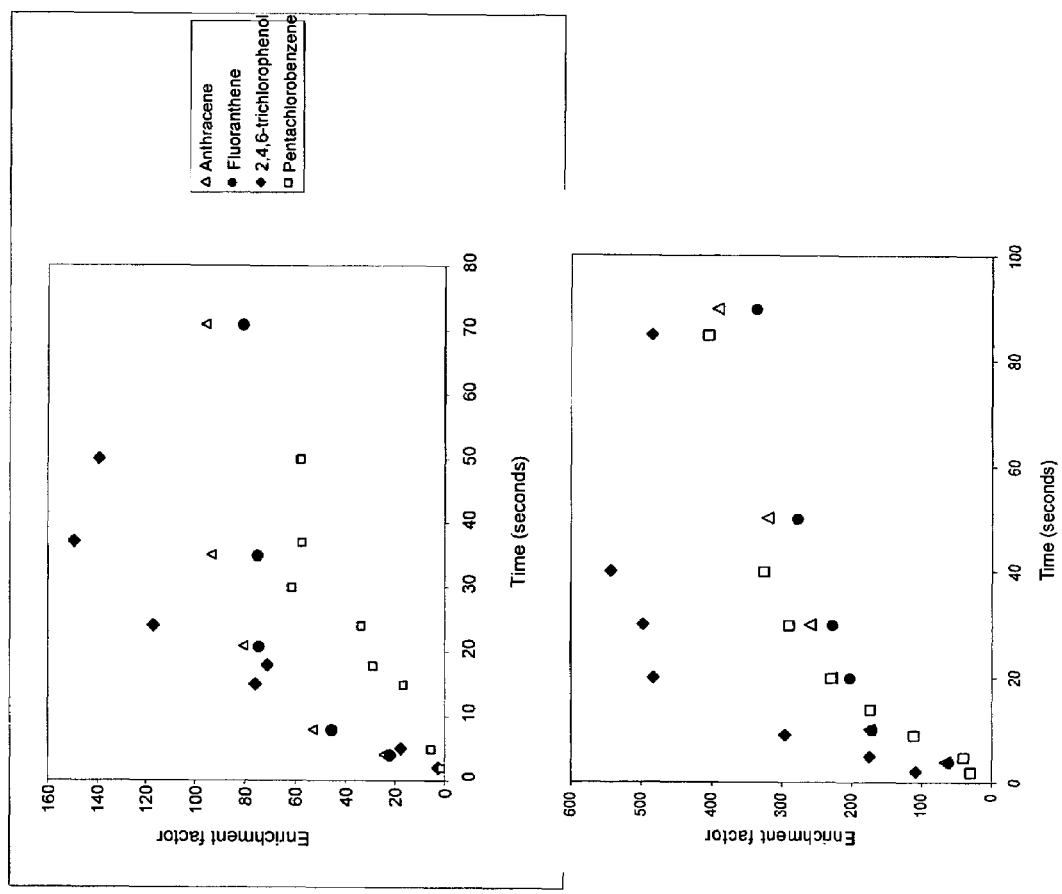
FIG. 41 shows extraction behaviour of microporous hollow fibres.

FIG. 41 shows the extraction behavior of the Accurel PP Q3/2 and Celgard microporous hollow fibres. This figure illustrates that the Celgard membrane gives a higher efficiency of enrichment with extraction time, while very long equilibration time (there is no equilibration at about 90 min). The Accurel hollow fiber gives lower enrichment and equilibration is reached at about 40 min.

The extraction process depends on the partition coefficient between the organic acceptor solution and the aqueous donor solution (eq 19):

$$K_{eq} = \frac{C_{a,eq}}{C_{d,eq}} \quad (19)$$

where $C_{a,eq}$ and $C_{d,eq}$ are the analyte concentration in the acceptor phase and donor phase after equilibration respectively.

Table 3 lists the highest total recovery and true recovery in the range of extraction time used. It can be seen that the true recovery of Celgard fiber is higher than that of Accurel fiber even though its total recovery is lower. The equilibration time of Celgard fiber is slower than Accurel fiber because of its low porosity even though its wall is thinner.

TABLE 3

Analyte Recovery Obtained from Two Hollow Fibers

| | Accurel | | Celgard | |
|---|---|---|---|---|
| | Total recovery | True recovery | Total recovery | True recovery |
| 2,4,6-trichlorophenol | 68 | 33 | 47 | 43 |
| pentachlorobenzene | 42 | 21 | 38 | 35 |
| Anthrane | 42 | 20 | 37 | 34 |
| Fluoranthene | 35 | 17 | 32 | 29 |

Behavior of internal standard in different hollow fibers. For the study of internal standardisation, $d_{10}$-fluoranthene was added in the acceptor phase before the extraction. The extraction and back extraction seem not to be symmetric.

Figure 42:
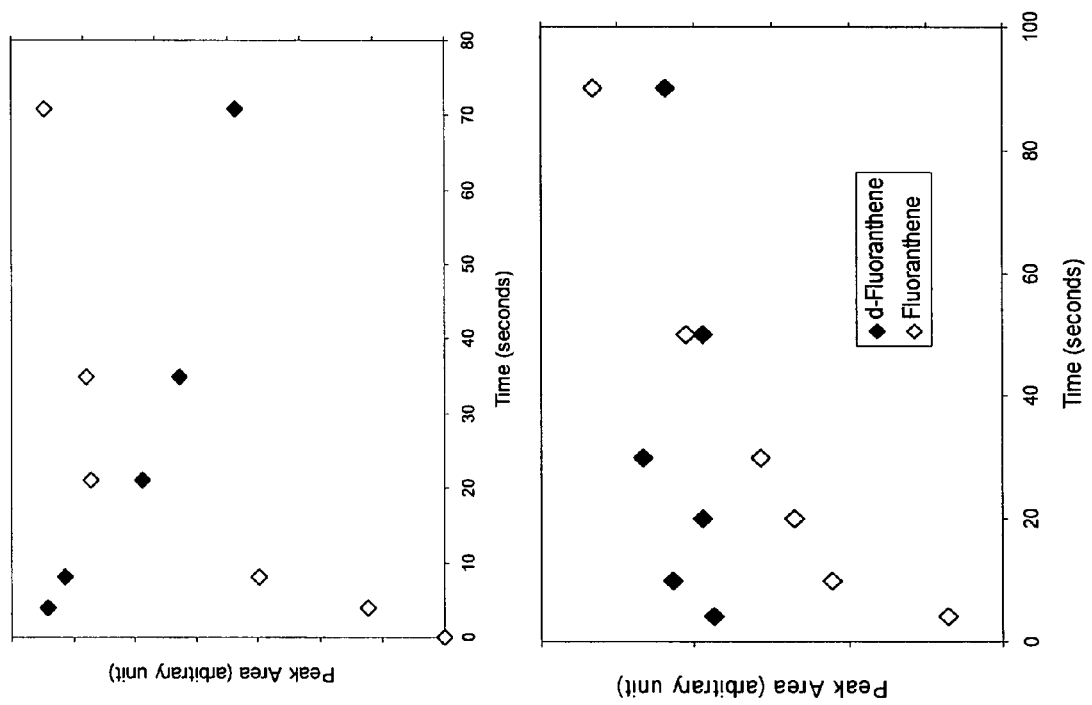
FIG. 42 shows extraction behaviour of microporous hollow fibres.

FIG. 42 illustrates the extraction and back extraction behavior with the Accurel PP Q3/2 and Celgard microporous hollow fibre. These data show that a relatively constant internal standard concentration was found for Celgard hollow fiber. The internal standard concentration in Accurel hollow fibre decreased with equilibration.

For the Celgard hollow fiber, the equilibrium quantification isn't practical because of the long equilibration time. But the stable concentration of internal standard may indicate that we can make quantification using the dynamic behavior. Also, the experimental condition may be optimized to increase the reproducibility of the experiments.

The two hollow fibers show considerable difference in the extraction and back extraction behavior. The Celgard hollow fiber shows better extraction efficiency than Accurel fibers, but both illustrate good results. Except for the difference in hollow fiber dimensions and morphology, a possible loss of organic solvent to aqueous solution should also be considered in their application in LPME.

EXAMPLE 9

Membrane Extraction with Calibrant in the Stripping Phase

In this example, membrane extraction is conducted with the calibrant present in the stripping phase.

Figure 43:
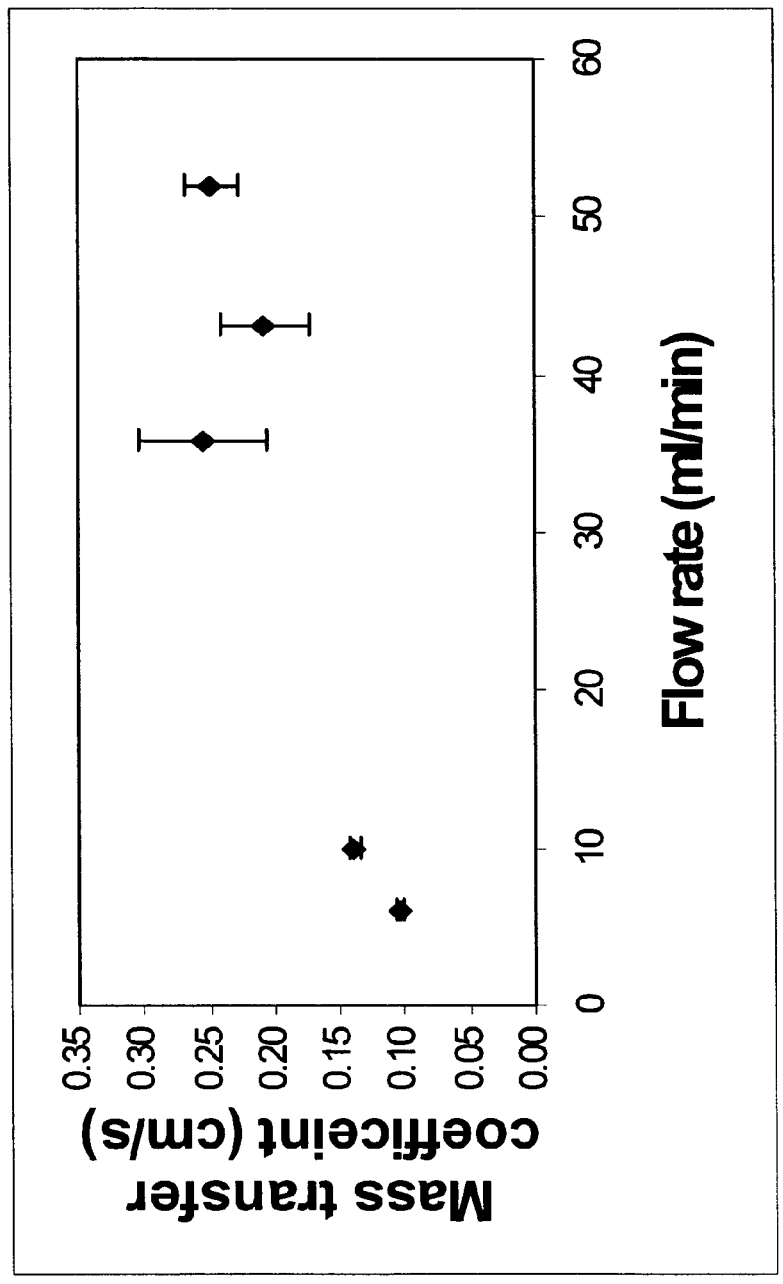
FIG. 43 shows the impact of flow rate on mass transfer coefficient of p-xylene.
Figure 44:
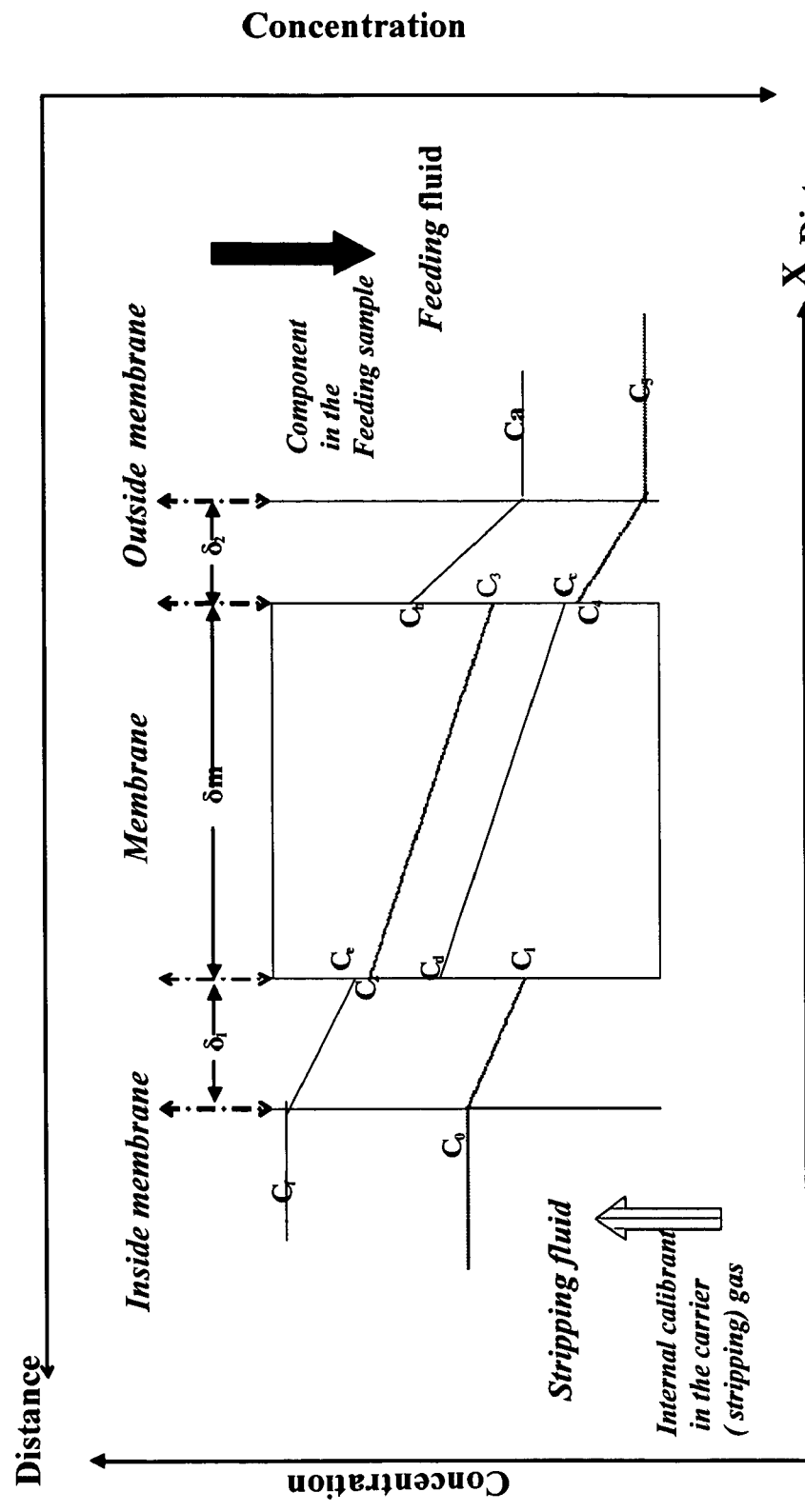
FIG. 44 illustrates concentration profiles in membrane extraction.
Figure 45:
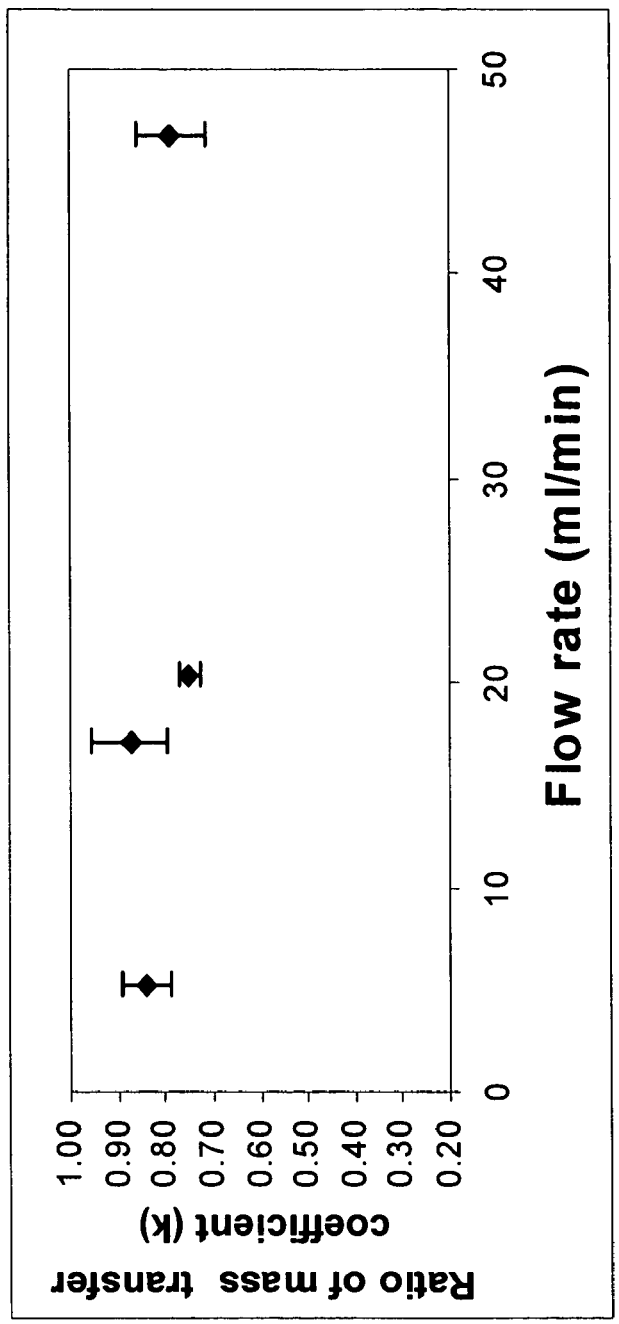
FIG. 45 shows mass transfer coefficient ratio between p,o-xylene.

FIG. 43 illustrates the dependence of sample flow velocity on the receiving end of the membrane and the mass transfer coefficient for p-xylene. The results in FIG. 43 were obtained for Membrane Extraction with Sorbent Interface (MESI) system. The strong dependence between the mass transfer and the flow rates indicates that the mass transfer through the boundary layer at the sample side controls the extraction rate, as illustrated in FIG. 44. FIG. 45 illustrates that this strong dependence can be successfully corrected by introducing the calibrant in the striping phase and then using ratio between the mass transfer rates corresponding to target analyte (p-xylene) and the calibrant (o-xylene). This is another example how the standard in the extraction phase can be used to calibrate on-site extractions.

EXAMPLE 10

Automation of SPME on a Multiwell Plate Format

Studies has been performed to evaluate feasibility of the automation of solid-phase microextraction (SPME) on a multi-well plate format. Four polycyclic aromatic hydrocarbons (PAHS) naphthalene, fluorene, anthracene and fluoranthene were chosen for extraction on polydimethylsiloxane (PDMS) extraction phases as they possess large partition coefficients $K_{fw}$ allowing differences in the extraction profiles to be easily determined whilst their semi-volatility reduced evaporative losses. Initial studies have involved the design of an array of SPME devices that can simultaneously be placed into a 96-well plate for parallel extraction. Extraction profiles were performed using 3 different SPME configurations. These included a PDMS membrane, a multi-fiber device containing 14 lengths (2 cm) of PDMS coated flexible wire and PDMS coated flexible metal fiber assemblies supplied by Supelco. Of these configurations, the PDMS membrane followed by multi-fibre device exhibited the greatest extraction rate and sensitivity and was related to the increased extraction phase surface area that this geometry provides. The inter-well variation of the 96-well plate was determined using parallel extractions in representative well locations and the reproducibility was found to be similar for intra- and inter well replicates ranging between 3.7 and 10.3%. Different agitation methods were assessed during the extraction process and included magnetic stirring, sonication, and orbital shaking at different speeds. It was found that using orbital shaking at 1400 rpm whilst holding the SPME device in a stationary position provided the optimum agitation conditions. Furthermore, solvent desorption was investigated on a 96-well plate format and provides exciting possibilities for automated high-throughput SPME analysis compatible to liquid chromatography.

Introduction. Automation of an analytical method provides a number of advantages including reduced analyst time both for routine analysis and method development, faster sample throughput and greater reproducibility. Without automation, acceptance and the range of potential applications for a new technique can be significantly reduced. Multiple samples are generated for analysis in real time environmental or in-vivo monitoring. In such cases, efficiency results from performing parallel extraction, desorption and sample introduction procedures, which are typically the time consuming steps of the SPME analytical procedure. The use of multiwell plates is a convenient, popular and easily automated means of performing a large number of replicates in a parallel fashion.

Experimental. Chemicals and Materials. Naphthalene (>99%) fluorene (>99%), anthracene (>99%), and fluoranthene (>99%) were purchased from Sigma-Aldrich (Missasauga, ON., Canada) and a 1 mg/mL stock standard was prepared in acetone and kept refrigerated in between use. Each day a fresh 200 ng/mL working standard was prepared by spiking 10 µL of the stock standard solution into 50.0 mL of water purified on a Nanopure ultrapure water purification system (Barnstead, Boston, Mass.).

Apparatus and Analytical Conditions:

GC-TOF/MS. Instrumentation: GC-TOF/MS instrument Pegasus 4D from LECO, Co. (USA) consisted of Agilent 6890N gas chromatograph with split-splitless injector, and time-of-flight mass spectrometer LECO Pegasus III (10 ml/min pumping capacity).

Gas chromatography: Column: RTX-5 (10 m×0.18 mm×0.2 µm), Restek, USA; oven temperature program: 50° C. for 2.0 min, 50° C./min to 250° C.; helium flow: 1.0 ml/min; injection mode: splitless; the injector was purged after 120 sec at 50 mL/min with the purge vent open to clean the injector; injection temperature: 250° C.; syringe injection volume: 1 µL; SPME liner: 0.75 mm ID SPME injection sleeve (Supelco, Bellefonte, Calif.).

Mass spectrometric detection: Acquisition rate: 10 Hz; mass range: 35-220 amu; ion source temperature: 200° C.; transfer line temperature: 250° C.; detector voltage: −1700V. Total analysis time was 6.0 min. ChromaTOF software (LECO, Co.) was used for the processing of collected data.

ATAS-GC/Q-MS: Instrumentation: The ATAS-GC/Q-MS instrument consisted of an Agilent 6890 gas chromatograph with a pneumatically controlled Direct Thermal Desorption (DTD) Optic 3 injection system (ATAS International, Veldhoven, The Netherlands), a CombiPAL™ robotic autosampler (CTC analytics, Zwingen, Switzerland) and Agilent 5973N single quadrupole Mass Selective Detector (MSD).

Gas chromatography: Column: Varian CP-Sil-8 (10 m×0.25 mm×0.25 µm), VWR International, Mississauga, ON, Canada; oven temperature program: 40° C. for 13 min, 15° C./min to 250° C. then held at 250° C. for 3 min; helium flow: 1.0 ml/min; injection mode: (see ATAS injection system below); injection temperature: 280° C.; syringe injection volume: 1 µL; Direct Thermal Desorption liners: 4 mm ID, 8 cm long DTD crimp top liner with frit used for pin and multifiber analysis, and 4 mm ID, 8 cm long DTD liner without frit used for PDMS membrane analysis (ATAS GL, Veldhoven, The Netherlands).

ATAS injection system: Column flow: 1.0 mL/min; pressure 18 psi; injector temperature program: Initially the injector is at 35° C., then ramped to 280° C. at a rate of 4° C./sec and remains at 280° C. until the completion of the GC method. Split: 0 mL/min for the first 800 sec and then a split of 20 mL/min is used until the end of the GC method to clean the injection port.

Cryotrap: The cryotrap was temperature programmed at 0° C. for 720 sec, then ramped at 15° C./sec to 280° C. for chromatographic separation to occur.

Autosampler: The CombiPAL autosampler software controlled the pneumatic pump which opened and closed the DTD liner exchange system. The robotic arm was programmed to transfer the liners sitting in the cooled liner tray into the injection port via the magnetic crimp top seal placed on the top of the DTD liner.

Mass spectrometric detection: Acquisition rate: 20 Hz; mass range: 90-220 amu; MS electron ionisation source temperature: 200° C.; MS quadrupole analyzer temperature: 150° C.; ionization energy: 70 eV. Total analysis time was 30.0 min. HP Chemstation™ Version C software was used for the processing of collected data.

Preparation of SPME Devices. Commercial metal fiber assembly: 100 µm and 30 µm film thickness PDMS-coated metal fibers were supplied by Supelco (Bellefonte, Calif.). The fibers were conditioned at 250° C. for 30 minutes in the injecton port of the GC prior to use.

PTFE top-plate: A block of PTFE was machined in the Scientific Technical Services workshop (University of Waterloo, ON., Canada) to the dimensions 8.0 cm×12.4 cm×1.0 cm. 96 holes were drilled through this at 9 mm intervals to align with the centre of the wells of a 96-well plate. Commercial metal fibre assemblies were placed in the drilled holes to align the fibres with the 96 well plate.

PDMS membrane: A PDMS membrane (Specialty Silicone Products Inc. Ballston Spa, N.Y.) was cut in the shape of an elongated pentagon of sides 2.0, ×2.0, ×2.0, ×1.5, ×1.5 cm of surface area 5.0 $cm^2$ on each side. The film thickness is 127 µm. This was placed inside the 3.5 cm loop of a folded 10 cm length of 19 guage stainless steel wire so it could be handled without contaminating the membrane. The membrane was conditioned at 120° C. overnight and then for 2 hours at 250° C. using a constant flow of carrier gas at 0.8 mL/min.

Multi-fiber brush: A multi-fiber "brush" was constructed out of 14 individual 2 cm lengths of PDMS-coated (100 µm film thickness) flexible nickel-titanium alloy wire which were glued using a high temperature epoxy resin into a 0.5 cm metal tube. On the opposite side of the tube a 3 cm stainless steel wire (19 guage) was attached for handling the multi-fiber device. The multifiber brush was conditioned at 120° C. overnight and then for 2 hours at 250° C. using a constant flow of carrier gas at 0.8 mL/min.

SPME Conditions. Extraction: SPME was performed in all cases from a 1.0 mL, 200 ppb aqueous solution of naphthalene, fluorene, anthracene and fluoranthene. The working standard was kept in an amber screw-top vial and the solution was transferred using a Hamilton gastight syringe through the 15 mm PTFE coated silicone septa to avoid analyte loss from the vial's headspace. ABgene 96-well deep well plates were purchase from Ultident (St Laurent, Canada). These plates possessed round wells with a U-bottom of volume 1.2 mL. Three agitation mechanisms were investigated. Sonication was performed in a water bath maintained at 30° C. using a Branson 5510 sonicator. Mechanical stirring was performed on a VWR Dyla™ Dual stirrer/hotplate set on "high" at room temperature. Circular magnets encased in PTFE molded into the shape of a triangle were placed at the bottom the wells of the 96 well plate to provide stirring within the well. Orbital shaking was performed on an Orbit™ P2 shaker from Labnet International Inc. that was capable of rotating between 100-1400 rpm at a horizontal orbit of 3 mm. When the stationary fiber technique was used the SPME device was inserted into a PTFE block, which was clamped via the use of a retort stand.

Desorption: Thermal desorption of the commercial SPME fiber assemblies were performed on the GC/TOF-MS at 250° C. for 2 minutes. For the SPME devices which did not fit into a standard GC injection port, the ATAS-GC/Q-MS was used in the direct thermal desorption mode at 280° C. for 13 minutes using cryofocussing at 0° C. This allowed a direct comparison of the extraction profiles on differing SPME geometries.

Liquid desorption was performed by placing the SPME fiber into 200 μL of acetonitrile after the extraction process had taken place. ABgene 200 μL skirted 96-well plates were used for the liquid desorption process and agitated at 900 rpm for 40 min using orbital shaking whilst holding the fiber stationary. 100 μL were silanized overnight using a 10% solution of dichlorodimethylsilane in toluene, then rinsed with toluene, then methanol and dried in the oven at 120° C. for several hours. Nitrogen evaporation was performed using an in-house built device capable of delivering a slow stream of nitrogen to all locations in a 96-well plate. Reconstitution was performed using a Hamilton gas-tight syringe prior to injection.

Results and Discussion.

Different SPME Designs for Automation on a Multi-Well Plate Format.

SPME is typically performed using commercial fiber assemblies which consist of a silica rod coated with a stationary phase. This has been shown to be a particularly compatible format for thermal desorption in the injection port of a GC instrument. However other geometries exist which increase the volume and/or the surface area of the extraction phase which can lead to improvements in the sensitivity of the analytical procedure and increase the rate of extraction which in turn reduces the total analysis time. In this study four different configurations were investigated for their extraction characteristics. These include a 127 μm PDMS membrane of surface area 5 cm², a multi-fiber "brush" constructed from 14 cm lengths (2 cm) of a flexible metal alloy coated with a film of PDMS (100 μm thick), a 2 cm silicone hollow fiber membrane of 360 μm thickness placed over a stainless steel pin and metal fiber assemblies coated with various PDMS film thicknesses provided from Supelco. The extraction characteristics of these SPME phases were assessed under identical agitation conditions (900 rpm orbital shaking). After the extraction was performed, each SPME phase was inserted into a liner compatible with a CombiPAL™ robotic liner exchange system for automated transferral into an ATAS injection port for thermal desorption. A cryotrap was used to focus the desorbed analytes over a period of 13 minutes before the temperature was increased allowing separation and detection to occur. Carryover studies were performed by reanalysing the SPME phase and it was determined that greater than 99% of the analytes were desorbed using this method.

Comparison of the extraction characteristics of the different SPME geometries used leads to the following order of decreasing extraction rate:

membrane>multifiber>PDMS (100 μm) metal fiber

The rate of extraction is related to the surface area of the SPME phase in contact with the sample solution and also the thickness of the extraction phase which slows the diffusion of analytes into the extraction medium. Furthermore, by increasing the volume of the extraction phase, the sensitivity of analysis is also improved. The SPME phases can also be ranked based on their extraction capacity and the order is the same as was stated above for the extraction rate. Thus, the PDMS membrane has the highest volume and hence extracts the greatest amount of target analyte from the well.

However both the membrane and the multifibre device are much more difficult to produce then a single fibre unit.

Choice of the Method for Agitation. Several methods of agitation were investigated to assess which required the least amount of time to reach equilibrium. Extractions were performed from a 200 ppb aqueous standard solution using 100 μm film thickness PDMS-coated fibers. Following extraction methods were compared: no agitation (static); orbital shaking of both the 96-well plate and the exposed fiber at 100 rpm and 900 rpm; orbital shaking of the 96-well plate at 900 rpm and 1400 rpm whilst the fiber was clamped stationary in position; magnetic stirring; and sonication.

Increasing the rate of orbital shaking improves the equilibration time. Moreover, using 1400 rpm (the upper limit of the multi-well plate shaker) whilst the fiber was held stationary allowed equilibrium to be reached most quickly at approximately 20 minutes. Holding the fiber stationary gave an added stirring effect to the agitation mechanism which allowed the analyte to be extracted at a faster rate.

Sonication was comparable to orbital shaking at a rate of 900 rpm and reached equilibrium after approximately 40 minutes. However, practically sonication is more difficult to perform as the water must be replaced at regular intervals to avoid irreproducible data due to temperature variations over the course of the experimental procedure. Magnetic stirring was performed by placing a small triangular magnetic stirrer wedge in the well and performing the extraction in the liquid above the magnet. This was not found to improve the rate of extraction as markedly as orbital shaking methods at higher rotational velocity. Another disadvantage of agitation by magnetic stirring was the non-uniform rate of stirring for different magnets in different well locations due to the inhomogeniety of the magnetic field provided by the magnetic stirrer. As expected, extraction under static conditions provided the slowest extraction rate of all the techniques tested due to slow rate of diffusion through the boundary layer surrounding the extraction phase.

Liquid Desorption for Automated Syringe Injection. Thermal desorption is the most common method for introducing volatile analytes extracted by SPME into the injection port for gas chromatography. However, solvent desorption is a viable alternative for semi-volatile and non-volatile analytes whereby the analytes can be removed from the SPME phase by immersion in an appropriate solvent. Polar solvents such as methanol or acetonitrile are suitable solvents for PDMS phases since non-polar solvents damage the extraction phase. The ability to perform solvent desorption from the SPME phase provides the potential for automated liquid injection in GC or LC systems. This is particularly desirable for LC where relatively few automated SPME techniques exist in comparison to GC due to the difficulty associated with the automated introduction of analytes onto the LC column using the typical SPME fiber format.

If an array of SPME fibers is used, the time consuming extraction and solvent desorption steps can then be performed in parallel on a multi-well plate format. The top plate is engineered so transferral of the SPME array between multi-well plates can be performed manually by means of a handle or it can be mounted onto a robotic system for automation.

Preliminary investigations showed acetonitrile to extract a larger proportion of the PAHs used in this study than when methanol was used. As the partition coefficient of the analytes increase, the ability of the solvent to remove the analyte from the extraction phase is reduced. A 96 well plate filled with 200 μL of acetonitrile was found to desorb greater than 92% of the analytes.

The volume of the desorption solution must be minimised as typically only a small proportion of this solution will be injected into a GC or LC for analysis. Another approach is to evaporate the solvent by blowing an inert gas such as nitrogen onto the contents of each well. Once evaporated, the sample can be reconstituted into an appropriate solvent volume for analysis increasing the sensitivity of the analysis.

Table 4 shows that analyte remains bound to well walls. When nitrogen blowdown and reconstitution in 10 μL of solvent was performed in a 200 μL conical shaped well the recovery for fluoranthene was only 27% indicating that most of the analyte remained bound to the wall of the well through hydrophobic interactions during the blowdown procedure. Furthermore, it is not possible to rinse the walls of the well with a small volume of solvent (10 μL) in an automated fashion. Hence a silanized glass insert was used to reduce the affinity of the hydrophobic analytes for the wall and the recovery was increased to 87% for anthracene and fluoranthene. Ideally, when performing automated liquid desorption, evaporation and reconstitution, an internal standard is best added to quantitate the loss of semi-volatiles through evaporation.

Conclusions. Preliminary investigations into the automation of SPME on a multi-well plate format have indicated it to be a viable technique for semi-volatile and in particular non-volatile compounds. Using an array of SPME devices which are housed in a top-plate that fits over the multi-well plate to perform the time consuming extraction and solvent desorption steps in parallel presents a time efficient method for the evaluation of multiple samples.

The inter-well variation during the extraction process across three representative locations of the 96-well plate were found to be negligible which is essential for reproducible results to be obtained when using an array of multiple fibers for extraction. Of the different geometries assessed for the extraction process, the thin (127 μm thick) PDMS membrane offered the fastest extraction rate and the highest sensitivity due to its increased surface area and volume. Different agitation methods were investigated for extraction on a format and orbital shaking of the multi-well plate at 1400 rpm when the fiber was clamped in a stationary position achieved the fastest rate of extraction. By holding the fiber stationary, an added stirring effect allowed faster equilibration than when orbital shaking was used with the fiber attached to the top of the 96 well plate.

Of the analytes used in this study fluoranthene exhibited limited volatility and did not evaporate during nitrogen evaporation however silanized glass inserts were required to reduced the adsorption of the analytes to the wall of the well. Future work will analyse PAHs in real water samples on a multi-well plate format utilizing internal standards to quantitate the loss of semi-volatiles through evaporation.

EXAMPLE 11

High Performance SPME/AP MALDI System for High Throughput Sampling

This example presents the performance characteristics for a multiplexed solid phase microextraction/atmospheric pressure matrix-assisted laser desorption ionization (SPME/AP MALDI) source configuration for a hybrid quadrupole-linear ion trap (QqLIT) instrument. The results demonstrate that thorough optimization of parameters such as SPME coating material, optics configurations, extraction solvents, and fiber capacity provides dramatic sensitivity improvements (>1000x) over previous reports in the literature. The multiplexed SPME plate is capable of simultaneous extraction from 16 different wells on a multiwell plate, eliminating the need for extensive sample preparation. Subfemtomole sensitivity is demonstrated for peptide standards and protein digests with run-run reproducibility ranging from approxi-

TABLE 4

Sample enrichment using nitrogen evaporation and reconstitution in acetonitrile.

| Analyte | Recovery after $N_2$ evaporation and reconstitution in 200 μL (%) | Recovery after $N_2$ evaporation and reconstitution in 10 μL (%) | Recovery after $N_2$ evaporation and reconstitution in 10 μL using a 100 μL silanized glass insert (%) |
|---|---|---|---|
| Naphthalene | — | 1.7 | — |
| Fluorene | 41.3 | 51.7 | 65.8 |
| Anthracene | 69.2 | 30.0 | 87.4 |
| Fluoranthene | 107.8 | 27.1 | 86.5 | mately 13-31%. This high performance SPME/AP MALDI system shows potential for high throughput extraction from biological samples.

Introduction. Matrix-assisted laser desorption ionization (MALDI) has become a powerful technique for the analysis of proteins and peptides by mass spectrometry (MS) since its introduction in 1987. Though MALDI has enabled the routine identification of biomolecules, the need to increase the throughput of the method has been recognized. Sample preparation for MALDI is still the time limiting step, since it dictates the quality of the MS spectra. Efforts have focused on trying to produce more uniform co-crystals between the analytes and the matrix to improve the performance and reproducibility. Others have attempted to combine the sample extraction onto the MALDI target. Surface enhanced laser desorption ionization (SELDI) protein chip arrays are commonly used in proteomic research. These SELDI devices still require substantial sample preparation and the automation is also expensive.

As a simple and efficient sample preparation technique, solid phase microextraction (SPME) has been widely used with gas chromatography (GC) and more recently with liquid chromatography (LC). Recently several research groups have coupled SPME to other types of mass spectrometers. Meurer and coworkers demonstrated direct coupling of SPME with an electron impact (EI) mass spectrometer. Referred to as fiber introduction mass spectrometry (FIMS), this method was used to analyze volatile and semi-volatile compounds by direct insertion of a poly(dimethylsiloxane) (PDMS) coated SPME fiber into the ion source after headspace extraction. Teng and Chen reported the combination of SPME with MALDI-MS. A sol-gel-derived 2,5-dihydroxybenzoic acid (DHB) film was employed as the SPME extraction coating and the substrate to help ionization without the addition of matrix. After extraction, the SPME fiber was attached on a MALDI plate with double-sided carbon tape. This procedure was not amenable to automation and only the analytes on one side of the SPME fiber could be introduced to the MS. Direct coupling of an SPME fiber to a laser desorption mass spectrometer has also been described with ion mobility and time-of-flight (QqTOF) instruments. The SPME/MALDI fiber was employed both as the SPME extraction phase and MALDI substrate, however, the sensitivity was poor (pmol/mL detection limits). This paper further investigates the coupling of SPME/MALDI to mass spectrometry. A multiplexed SPME plate was coupled to a high performance hybrid quadrupole-linear ion trap (QqLIT) with a modified AP MALDI source. Since extraction time is typically the rate limiting step for SPME/AP MALDI analyses, the sample throughput can be improved by a factor approaching the number of fibers on the device. In this case, the multiplexed plate permits 16 simultaneous extractions from a 96 well plate. In addition, a number of operational parameters were optimized to improve the system performance. Optimization of the laser illumination geometry provided more than a 100-fold improvement in the S/N ratio for peptides. The addition of a-cyano-4-hydrocinnamic acid (a-cyano) matrix to the extraction solvent gave improvements of approximately 100× and 32× for the absolute signal and S/N ratio for peptides, respectively. Analytical performance was also improved by using extraction fibers with increased surface areas (larger extraction capacity) and an improved atmosphere-vacuum interface. The combination of all these improvements gave detection limits of less than 500 amol/mL for protein digests with typical fiber-fiber reproducibilities on the order of 13-31%. For these studies 2 different SPME coatings were evaluated (polypyrrole and polythiophene) and the extraction efficiency was determined. This system presents a low cost, easy to use high throughput sample preparation tool for AP MALDI-MS analysis.

Experimental.

Chemicals. Pyrrole, thiophene, anhydrous ferric chloride, isopropanol, formic acid, angiotensin II, angiotensin I, bradykinin and glufibrinopeptide b were purchased from Sigma-Aldrich (St. Louis, Mo.). Isopropanol and ammonium persulfate were purchase from VWR (Toronto, ON, Canada). The a-cyano-4-hydrocinnamic acid MALDI matrix was purchased from Agilent (Palo Alto, Calif.). Bovine serum albumin (reduced and carboxymethylated BSA) was purchased from Sigma Chemical Co (St. Louis, Mo.). Prior to digestion, protein samples were prepared at 5 mg/mL in 50 mM ammonium bicarbonate (BDH Chemicals, Toronto, ON, Canada) buffer adjusted to pH 8.5 with ammonium hydroxide (Fisher Scientific, Nepean, ON, Canada). Digestions were carried out with a ratio of 20:1 protein:trypsin. Proteins were digested for 4 hours at 37° C., and the digests were stored at −20° C. prior to use. Digests were reconstituted in water with 0.1% formic acid. Nanopure deionized water was exclusively used in these experiments. A 4-peptide mixture containing angiotensin II, angiotensin I, bradykinin, and glufibrinopeptide b was prepared in water with 0.1% formic acid.

Preparation of the SPME Fibers. High OH silica optical fibers with core diameters of 600 μm were purchased from Polymicro Technologies Inc. (Phoenix, Ariz.) for the assessment of performance with different optical configurations. The connector ferrule, F-112 epoxy glue, polishing disc and polishing films (5, 3, 1 and 0.3 μm) were purchased from Thorlabs Inc. (Newton, N.J.). The silica optical fibers were cut into 1-meter sections with a capillary cutter from Restek (Bellefonte, Pa.). One end of the optical fibers was glued to a connector ferrule with F-112 epoxy glue from Thorlabs Inc. (Newton, N.J.). After 24 hours curing time, this fiber connector end was polished with polishing films to ensure the maximum light throughput. The other end of the optical fiber, hereafter called sampling end, was coated with polymer coating and used for extraction. About 1 cm of the optical fiber was first cut from the sampling end to have a fresh clean surface to work with. Then the fiber tip was etched with 400-grit silicon carbide polishing paper. The etching step ensured that the polymer adhered to the fiber tip. The tip was then sonicated in methanol to remove the impurities on the fiber tip. After rinsing with water, the fiber tip was ready for the coating process.

Preparation of Multiplexed SPME/MALDI Plate. Glass rods with 2 mm diameter obtained from the University of Waterloo glass shop were used to prepare the SPME fiber tips for the multiplexed SPME/AP MALDI plate. The glass rods were cut into 3 cm sections, and then one tip and the sides of the rods were etched with 400-grit silicon carbide polishing paper. The tip was then cleaned with the same procedure described above.

A standard ABI stainless steel MALDI plate (AB/MDS SCIEX, Concord, ON) was used to prepare the multiplexed plate. A total of 16 holes were drilled on the plate and sixteen coated SPME tips were glued into place. The tips were cut so that the sampling ends protruded from the flat surface of the plate by approximately 5 mm. The tips were positioned to provide alignment with the wells on a 96-well plate to permit simultaneous extraction from multiple wells.

Preparation of Polypyrrole (PPY) Coated Fibers and Tips. Polypyrrole was prepared by chemical oxidation of pyrrole monomer with ammonium persufate. All the solutions were prepared fresh prior to the coating procedure. Up to ten fibers or glass tips could be prepared simultaneously. First the fiber tips were immersed in 20 mL of 0.4 M ammonium persulfate aqueous solution. Then 20 mL of 0.4 M pyrrole solution in isopropanol:water (50:50) was added dropwise. The mixture was stirred for 3 hours. After stopping the reaction, a layer of black polymer coating could be observed on the fiber tips. The tips were then rinsed with deionized water and left to air dry.

Preparation of Polythiophene (PTH) Coated Fibers and Tips. Polythiophene (PTH) coated fibers and tips were prepared using the following chemical polymerization method. 11 A total of 2.4 g of $FeCl_3$ was first thoroughly dried at about 100° C. in a reaction flask for one hour under reduced pressure with the presence of dry nitrogen gas. This was followed by the addition of 50 mL of dry chloroform. Up to 10 optical fibers or glass tips were prepared in the same flask by dipping the tips in the $FeCl_3$ and $CHCl_3$ mixture. Subsequently 0.42 g of thiophene monomer was added dropwise into the mixture with stirring. The reaction mixture was then stirred for 48 hours at room temperature under a continuous flow of nitrogen. The fibers were then removed and rinsed with methanol. A dark-red color could be observed after rinsing off ferric chloride from the fiber tips.

Extraction Process. Samples were diluted to various concentrations in water containing 0.1% formic acid. Various concentrations of a-cyano-4-hydrocinnamic acid MALDI matrix were mixed with a 1:1 ratio with the samples prior to extraction. For some experiments, no matrix was added to the extraction samples.

The extraction process involved immersion of the SPME fiber tips in the sample solutions. Extraction times were typically 2 minutes unless otherwise stated (Wang et al., J. Rapid Commun. Mass Spectrom. 2004, 18, 157-162, herein incorporated by reference). The tips were air dried for 2 minutes after extraction. Experiments showed that an aqueous rinse was insufficient to prevent carry-over, so after every run, the PPY fiber tips were cleaned by soaking in methanol for one minute followed by a rinse with methanol. The PTH tips were cleaned by soaking in acetonitrile/water (50:50) followed by methanol/water (50:50) for 30 seconds each. Different rinse procedures were used for the 2 coatings to account for differences in stability with organic solvents.

The preliminary coating evaluation was carried out with a SRI 9300B GC system with a FID detector (SRI instruments, Torrance, Calif.). The column used was a 1 m×0.53 mm MXT-5 silicosteel™ GC column (Restek, Bellefonte, Pa.) with a 1.00 µm coating thickness. The GC oven was initially held at 70° C. for 0.5 min, then ramped to 300° C. at 20° C./min. The hydrogen carrier gas flow rate was set at 10 ml/min. After extraction from tetraoctylammonium bromide (Sigma-Aldrich, St. Louis, Mo.) solution, the extracted analyte was then desorbed in methanol and injected into GC for analysis. Both coatings were evaluated for comparison.

SPME/AP MALDI coupled to a QqLIT. SPME devices were coupled to a modified 4000 QTRAPTM mass spectrometer (MDS SCIEX, Concord, ON, Canada) with a modified AP MALDI ion source as reported previously (Schneideret al., J. Am. Soc. Mass Spectrom. 2005, 16, 176-182, herein incoporated by reference). The instrumental modifications involved increasing the gas throughput of the interface by a factor of 4 with a larger orifice plate aperture (0.6 mm). In addition, a QJETTM was incorporated to replace the standard skimmer in order to reduce the gas load on subsequent vacuum stages. (Javaheri et al., Proceedings of the 53rd ASMS Conference on Mass Spectrometry, Jun. 5-9 2005, San Antonio, Tex., herein incorporated by reference). This configuration improved AP MALDI performance for peptides by a factor of approximately 2 over previous iterations (data not shown). The laminar flow chamber temperature was maintained at 200° C. for all experiments. A nitrogen laser from LSI (Frankin, Mass.) was used for all experiments with 10 Hz repetition rate. The AP MALDI source stage was repositioned by removal of shims so that the tips of the SPME rods could be placed approximately 2 mm in front of the laminar flow chamber entrance. Approximately 2000 V was applied to the stainless steel sample plate. For experiments with the optical fibers, the standard source flange was removed and the fibers were placed approximately 2 mm from the inlet of the laminar flow chamber. An alligator clip was fastened to the SPME fiber about 1 cm from the fiber tip to provide a potential onto the electroconductive polymer to improve the sampling efficiency for ions. The voltage used in these experiments was 2 kV.

Using the coated optical fibers, performance comparisons were made using 2 different laser illumination geometries. The first geometry involved attachment of the laser directly to the opposite end of the coated optical fiber in a similar fashion to experiments described in the literature (Wang et al., J. Rapid Commun. Mass Spectrom. 2004, 18, 157-162). With this configuration (hereafter referred to as transmission geometry), the laser light was transmitted through the optical fiber (600 mm), conductive polymer, and then sample extraction surface. The second optical configuration (hereafter referred to as reflection geometry) involved attachment of the laser to the standard optics in the AP MALDI source (200 mm fiber) such that the light was directed at approximately a 28° angle to the fiber surface as described previously (Schneider et al., J. Am. Soc. Mass Spectrom. 2005, 16, 176-182).

Results and Discussion.

Optimization of Performance: Comparison of Transmission and Reflection Geometry. In previous direct couplings of SPME and AP MALDI, only transmission geometry was employed. Experiments were conducted with samples of BSA digest to compare the performance with the 2 illumination geometries. Much higher laser power settings (give values for 10% vs 60%) were required when using transmission geometry.

Figure 46:
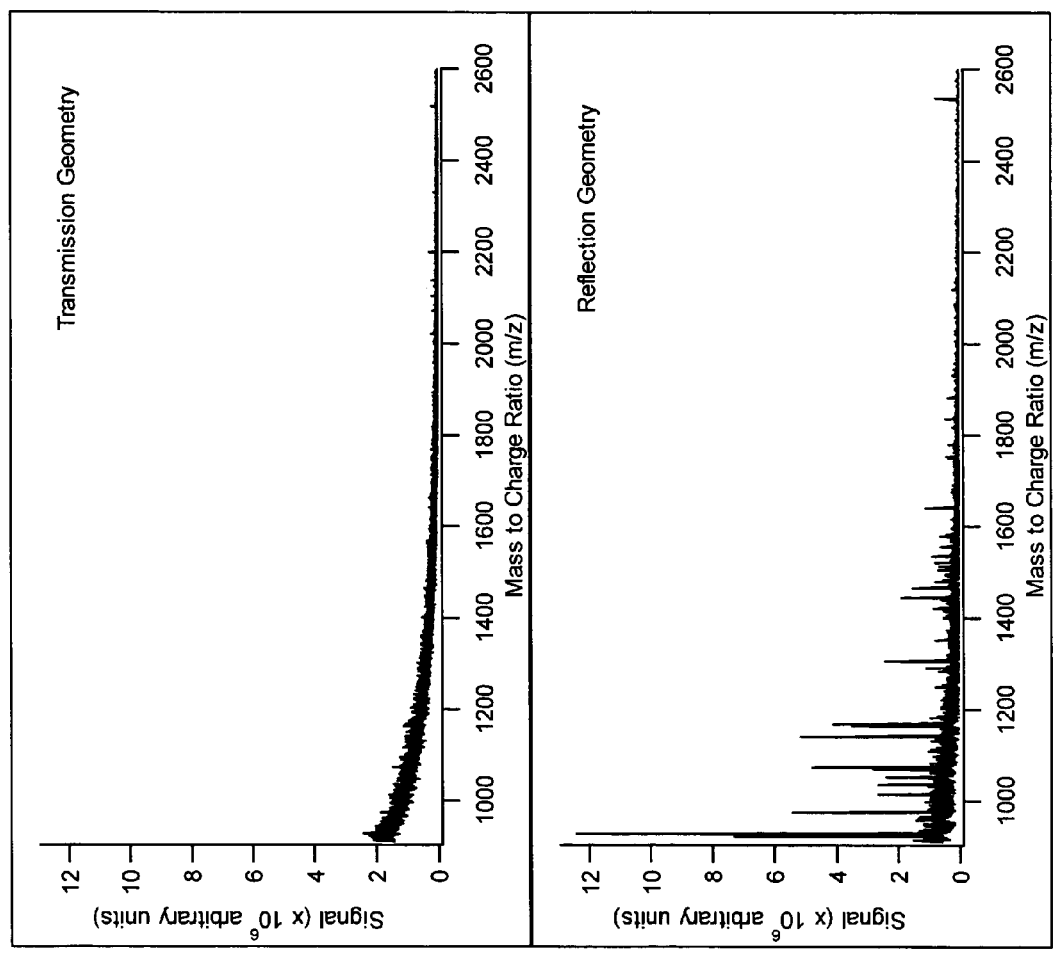
FIG. 46 shows a performance comparison for a 5 minute extraction from a sample of 10 fmol/mL BSA digest using a single PTH fibre.

FIG. 46 shows an example of the performance comparison for a 5 minute extraction from a sample of 10 fmol/mL BSA digest using a single PTH fiber. The data illustrates a comparison of performance for a 10 fmol/mL sample of BSA digest with transmission and reflection geometry. The extraction time was 5 minutes and a PTH fiber was used for these experiments. Trap operational parameters: Scan speed=4000 Da/s and fill time=150 ms.

The Y axes were scaled identically for the 2 sets of data so that they could be compared directly. Although these data were generated using a PTH fiber, similar trends were observed using PPY fibers as well. There was a substantial background when using transmission geometry, however peptide peaks could not be observed at the 10 fmol level. In contrast, a large number of peptide peaks could be observed with S/N ratios ranging up to 17 when using reflection geometry even though the optical fiber was positioned in the same location within the source region for both experiments. In order to achieve similar S/N ratios for this sample using transmission geometry, the BSA digest concentration had to be increased to greater than 1 pmol/mL. For these experiments, the sample surface was illuminated until no further ion current was generated (quantitative removal of analyte from the fiber surface). Since the entire surface was illuminated simultaneously with the transmission geometry, sample depletion from the surface required approximately 10 s. However with reflection geometry, the ablation area was much smaller than the fiber surface area. Quantitative removal of analyte required rastoring around the fiber surface. Under these conditions, analyte signals were observed for approximately 3 min. Reflection geometry was used for all other experiments described in this paper.

Ionization Efficiency for Conductive Polymers. Matrix addition to the extraction sample was also evaluated to try to improve the analytical performance of the SPME/AP MALDI system. Extractions were carried out using a sample of 100 fmol/mL angiotensin II. Data were collected sampling directly from the acidified aqueous sample solvent, sampling from solvent prepared by mixing the sample solvent directly with undiluted a-cyano matrix (1:1 ratio), and mixing the sample solvent directly with a-cyano matrix (1:1 ratio) that was diluted by a factor of 10 with water containing 0.1% formic acid. For each of the 3 extraction conditions, 4 separate runs were conducted with different tips.

Figure 47:
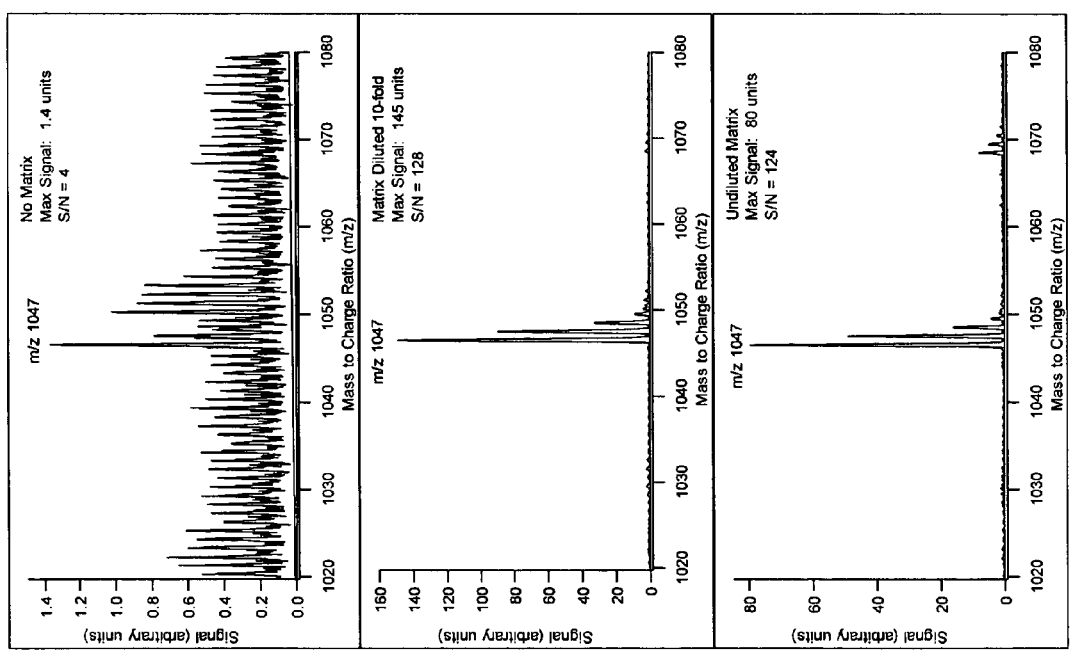
FIG. 47 shows average data obtained using PPY fibers, with the Y axes scaled identically for comparison purposes.

FIG. 47 shows average data obtained using PPY fibers, with the Y axes scaled identically for comparison purposes. Comparison of performance for 100 fmol/mL angiotensin II using direct ionization from the surface of the PPY fiber (no matrix addition) and incorporating various amounts of matrix to the extraction solvent. Trap operational parameters: Scan speed=250 Da/s and fill time=150 ms. The addition of matrix to the extraction solution provided a dramatic improvement in SPME/AP MALDI performance. The addition of undiluted matrix provided increases of 57× and 31× for the absolute signal and S/N for the molecular ion of angiotensin II. Dilution of the matrix provided an additional signal improvement (approximately a factor of 2), but the S/N ratio was essentially unchanged. The increased ion intensity with matrix dilution was likely due to the resulting increase in aqueous content of the extraction solution (50% aqueous→95% aqueous) since the matrix was diluted with acidified water. This may increase the distribution constant for the analyte in the extraction phase. In addition, the decrease of the total amount of matrix in the extraction solution may decrease the competition for the surface, allowing more peptides to be adsorbed. Therefore, for all further experiments in this paper aqueous samples were mixed with a 1:1 ratio with a-cyano matrix diluted 10×. Similar behavior was observed with SPME devices coated with PTH.

Comparison of PPY and PTH Coatings. Conductive coatings of PPY and PTH were evaluated. GC experiments were initially conducted to compare the extraction ability and reproducibility for the 2 polymer coatings. GC experiments showed signal improvements of 1.9× for the PPY fibers as opposed to the PTH fibers. In addition, the run to run reproducibility (as measured by the relative standard deviation) was 9% for the PPY fibers and 21% for the PTH fibers. Experiments with the QqLIT also showed poorer performance and reproducibility with the PTH fibers. Differences in performance and reproducibility may be related to differences in the fiber surface morphologies.

Figure 48:
FIG. 48 illustrates the homogeneity of extraction surfaces using SEM to evaluate the homogeneity of the extraction surfaces with PTH coated devices.
Figure 49:
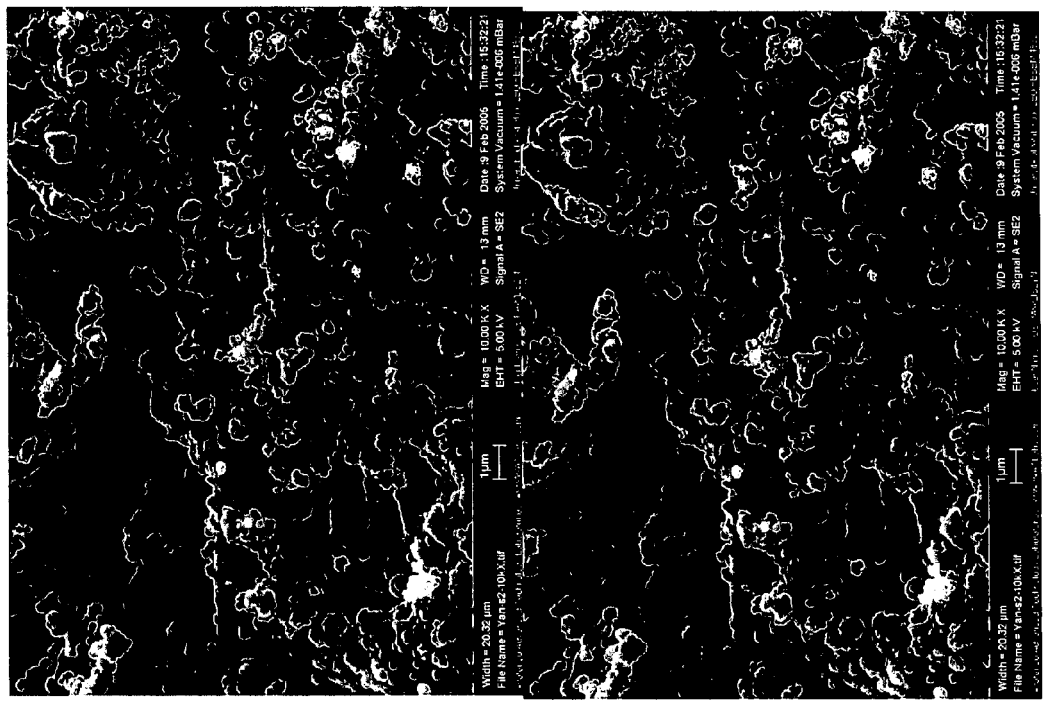
FIG. 49 illustrate homogeneity of extraction surfaces using SEM to evaluate the homogeneity of the extraction surfaces with PPY coated devices.

FIG. 48 and FIG. 49 illustrate homogeneity of extraction surfaces using Scanning Electron Microscopy (SEM) to evaluate the homogeneity of the extraction surfaces with coated devices for PTH and PPY, respectively.

FIG. 48 shows the scanning electron microscopy images of the PTH coating (upper pane) and the PTH coating after extraction from a mixture containing 10 fmol/mL BSA digest and matrix (lower pane). Operational parameters were 5000 V and 10 000× for the accelerate voltage and magnification.

FIG. 49 illustrates scanning electron microscopy images of the PPY coating (upper pane) and the PTH coating after extraction from a mixture containing 10 fmol/mL BSA digest and matrix (lower pane). Operational parameters were 5000 V and 10 000× for the accelerate voltage and magnification.

Similar conditions were used for the acquisition of the images with the 2 coatings, and the magnification was 10 000×. In each Figure, the top image depicts the surface of the coated fiber prior to extraction and the bottom image depicts the surface of the coated fiber after extraction from a mixture containing 10 fmol/mL BSA digest. The surface of the PTH coated fiber shown in FIG. 48 demonstrates a lack of surface uniformity with areas of filament-shaped particles and areas with alternate morphologies. The picture taken after extraction shows the presence of a number of areas where there appear to be gaps in the extracted material. The surface of the PPY coated fiber shown in FIG. 49 illustrates a more homogeneous morphology (ball-shaped structures). In addition, there appeared to be a more uniform and continuous layer of material on the surface after the extraction procedure. This difference in surface structure may be the reason for the improved performance with the PPY coated fibers. PPY coated fibers were used for all of the rest of the experiments described in this paper.

A number of PPY coated tips were also examined with blank extraction from the 10× diluted matrix solution to look for the presence of extra peaks resulting from ionization of various subunits of the PPY polymer. It was not possible to observe any peaks that corresponded to polymer ions. These results suggest that the polymer coatings might not be able to be ionized with the current laser fluence (380 J/m$^2$). Another possible explanation for the lack of PPY related ions in the mass spectra was that the proton affinity of the matrix was substantially higher than the proton affinity of PPY related molecules.

Evaluation of Analytical Performance.

Extraction Efficiency. The capacity of the SPME coating limits the amount of analyte that can be extracted from a particular sample. Typically this means that the actual amount of sample adsorbed on the fiber surface is very much lower than the amount of sample initially present in the extraction solution. Therefore, experiments were conducted with a 4 peptide mixture to evaluate the extraction efficiency using the large diameter (2 mm) fibers mounted on the surface of the multiplexed SPME plate. In order to evaluate the extraction efficiencies, 1 mL of a sample containing 20 fmol/mL of 4 different peptides was spotted onto the tip of 4 separate SPME fibers. Data were accumulated from each fiber until the sample was depleted from the surface and the 4 runs were averaged. After cleaning, the same 4 fibers were used to extract from wells containing 40 mL of the same mixture (20 fmol/mL). Data were accumulated from each fiber until the samples were depleted from the surface and the 4 runs were averaged. The peak intensities were compared for the 4 peptides and the extraction efficiencies were calculated using Equation 20:

$$\text{Extraction Efficiency} = \frac{\text{Signal Intensity}_{Extracted\ Sample}}{\text{Signal Intensity}_{Deposited\ Sample}} \times \frac{20\ fmol/\mu L \times 1\ \mu L}{20\ fmol/\mu L \times 40\ \mu L} \times 100\%$$

The extraction efficiencies were 0.3%, 0.2%, 0.1%, and 0.4% for angiotensin II, bradykinin, angiotensin I, and glufibrinopeptide b, respectively. The differences in peptide structure likely account for differences in the extraction efficiencies.

Reproducibility and Sensitivity. Tip to tip reproducibility was evaluated with the PPY coated tips using samples of the 4 peptide mixture.

Figure 50:
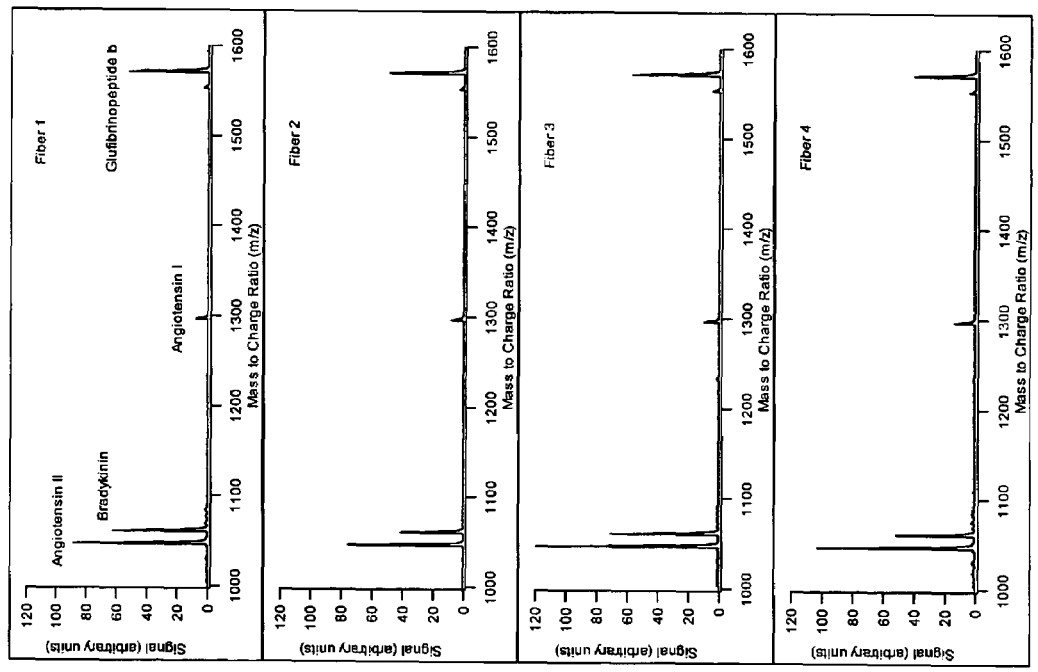
FIG. 50 shows an example of mass spectra obtained for samples with the 4 peptide mixture containing 20 fmol/mL of each peptide.

FIG. 50 shows an example of mass spectra obtained for samples with the 4 peptide mixture containing 20 fmol/mL of each peptide. Fiber to fiber reproducibility data for extraction from a sample containing 20 fmol/mL of angiotensin II, bradykinin, angiotensin I, and glufibrinopeptide b with 10-fold diluted matrix. The extraction time was 2 minutes. Trap operational parameters: Scan speed=4000 Da/s and fill time=150 ms. In each case, data were acquired until the sample was completely depleted from the tip of the fiber. As demonstrated in FIG. 50, separate SPME tips (labeled Fibers 1-4) were used for simultaneous extraction from 4 different sample wells. The 4 spectra were qualitatively similar showing the presence of the molecular ion for the 4 peptides as well as a small peak corresponding to the dehydration of glufibrinopeptide b.

Table 5 presents a quantitative comparison of the signal and S/N ratio for the 4 peptides. Typical RSDs (N=4) for the signal intensity and S/N ratio ranged from 13-31% and 11-27%, respectively. This was a substantial improvement over previous iterations and was likely due to a number of factors such as the improved control with simultaneous sampling, improved SPME technique, improved laser optics, and the more stable atmosphere to vacuum interface. In addition, the multiplexed plate allowed all extractions to be conducted simultaneously, reducing the total analysis time. The S/N ratios from these experiments can be used to estimate detection limits of 362 amol/mL, 619 amol/mL, 2.2 fmol/mL, and 295 amol/mL for angiotensin II, bradykinin, angiotensin I, and glufibrinopeptide b, respectively. These detection limits represent improvements on the order of 1000-7500× over previously published data.

fiber for 5 minutes, 10 minutes, and 10 minutes, respectively. Trap operational parameters: Scan speed=4000 Da/s, fill time=20 ms, and Q0 trapping enabled.

Figure 51:
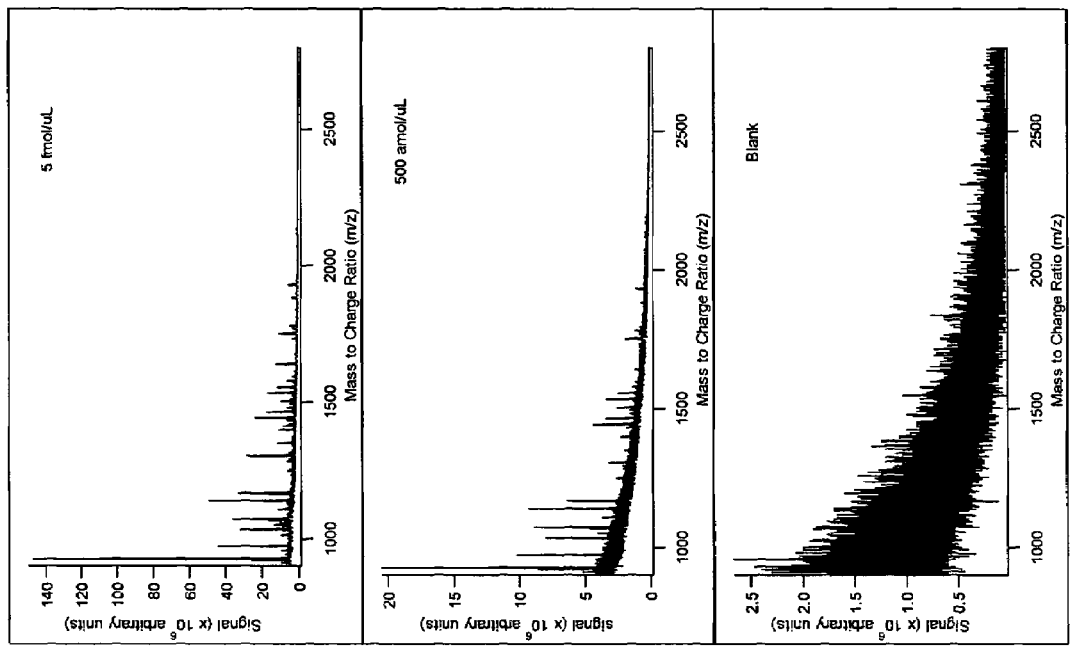
FIG. 51 shows analytical performance for BSA digest samples.

FIG. 51 shows data acquired (average of 8 runs each) for samples of 5 fmol/mL BSA digest, 500 amol/mL BSA digest, and a blank sample containing only matrix mixed with acidified water. The extraction times were 5 min, 10 min, and 10 min, respectively. Blank runs were taken before and after each of the measurements with the fibers to ensure that carry-over was not an issue. On average the peak heights and S/N ratios were approximately 6× and 5× greater for the 5 fmol/mL extractions than the 500 amol/mL extractions, respectively. These data suggest that the data generated with the lower concentration may have benefited from the extended extraction time. Future research will be focused on improving performance further with extended extraction times, as well as improving the homogeneity of the extraction material on fiber surfaces with the goal of achieving quantitative analysis. New extraction materials such as antibody coating are also in investigating for this purpose.

Conclusion. A new multiplexed SPME/AP MALDI plate was designed and evaluated on a QqLIT with a modified AP MALDI source. The experimental parameters were optimized to obtain a significant improvement in performance. The incorporation of diluted matrix to the extraction solution improved the absolute signal and S/N by 104× and 32×, respectively. The incorporation of reflection geometry for the laser illumination improved the S/N ratio by more than 2 orders of magnitude. Reproducibility was also improved as a result of these changes and the improved atmosphere-vacuum interface used for these experiments. The fully optimized high throughput SPME/AP MALDI configuration described in this paper generated detection limit improvements on the order of 1000-7500× those achieved prior to these modifications. This system presents a possible alternative for qualitative proteomics and drugs screening.

EXAMPLE 12

Development of Biocompatible SPME Fibers

The complexity of biological samples demands a powerful sample preparation technique and is usually the most critical and time-consuming step for drug analysis in biological matrices. Although extraction strategies such as solid-phase extraction (SPE) and liquid-liquid extraction (LLE) have been extensively used, it has become widely recognized that these sample preparation approaches can suffer from lengthy extraction times, excess use of solvents and poor automation capabilities. Solid-phase microextraction (SPME) is a relatively new approach to sample prepa-

TABLE 5

Quantitative comparison of fiber to fiber reproducibility for extractions from 4 different sample wells

| Fiber Number | Angiotensin II | | Bradykinin | | Angiotensin I | | Glufibrino-peptide b | |
|---|---|---|---|---|---|---|---|---|
| | Signal (×10$^7$ arbitrary units) | S/N Ratio | Signal (×10$^7$ arbitrary units) | S/N Ratio | Signal (×10$^7$ arbitrary units) | S/N Ratio | Signal (×10$^7$ arbitrary units) | S/N Ratio |
| 1 | 8.9 | 153 | 6.2 | 108 | 0.81 | 26 | 5.2 | 224 |
| 2 | 7.6 | 201 | 4.1 | 109 | 0.83 | 31 | 4.9 | 257 |
| 3 | 12.0 | 180 | 7.1 | 106 | 1.0 | 25 | 5.7 | 199 |
| 4 | 10.0 | 129 | 5.2 | 64 | 1.5 | 30 | 4.1 | 130 |
| Average | 9.6 | 166 | 5.7 | 97 | 1.0 | 28 | 5.0 | 203 |
| RSD (%) | 19 | 19 | 23 | 23 | 31 | 11 | 13 | 27 |

Analytical performance was also evaluated for protein digests.

FIG. 51 shows the analytical performance for protein digests for samples of BSA digest in which the Y axes have been scaled identically for comparison purposes. Analytical performance for samples of 5 fmol/mL BSA digest (top pane), 500 amol/mL BSA digest (middle pane) and a blank (bottom pane). Samples were extracted using a PPY coated ration, initially developed for the determination of volatile and semi-volatile organic pollutants in water. With respect to the use of SPME for drugs and poison detection from biological samples, the main advantages of SPME are high sensitivity, solventless extraction, small sample volume, simplicity, and speed. Successful automation and interfacing of SPME to high-performance liquid chromatography (HPLC) can be accomplished by arranging the fibers in a 96-well plate format.

However, commercially available SPME coatings lack biocompatibility and therefore the direct SPME extraction of drugs from biological samples often requires additional sample preparation, such as ultra-centrifugation, to eliminate the protein component of the sample. Direct exposure of the extraction coating to biological samples, is complicated by the presence and adsorption of interferents such as proteins and has conventionally limited the wide application of SPME for bio-analysis.

Herein is described a useful strategy to overcome the problem of biofouling by passivating conventional extraction phases by creating a thin biocompatible interface (or film) through the coupling of certain neutral and hydrophilic macromolecules, such as polyhydroxyethyl methacrylate, polyacrylamide, poly-N,N-dimethyl acrylamide, dextran, polyacrylonitrile (PAN) and polyethylene glycol (PEG). These protective layers repel proteins and allow extraction of small molecules of target analytes. The modified SPME fibers can also be easily prepared by physical or electrostatic adsorption of the biocompatible polymer onto the surface of regular extraction phases.

Steps in Biocompatible Fiber Preparation: Fibers with polyacrylonitrile protective layer. Biocompatible fibers were prepared by protecting commercial CW/TPR fibers (Supelco, Bellefonte, Pa.) with PAN (polyacrylonitrile, Sigma/Aldrich, Mississauga, ON).

Figure 52:
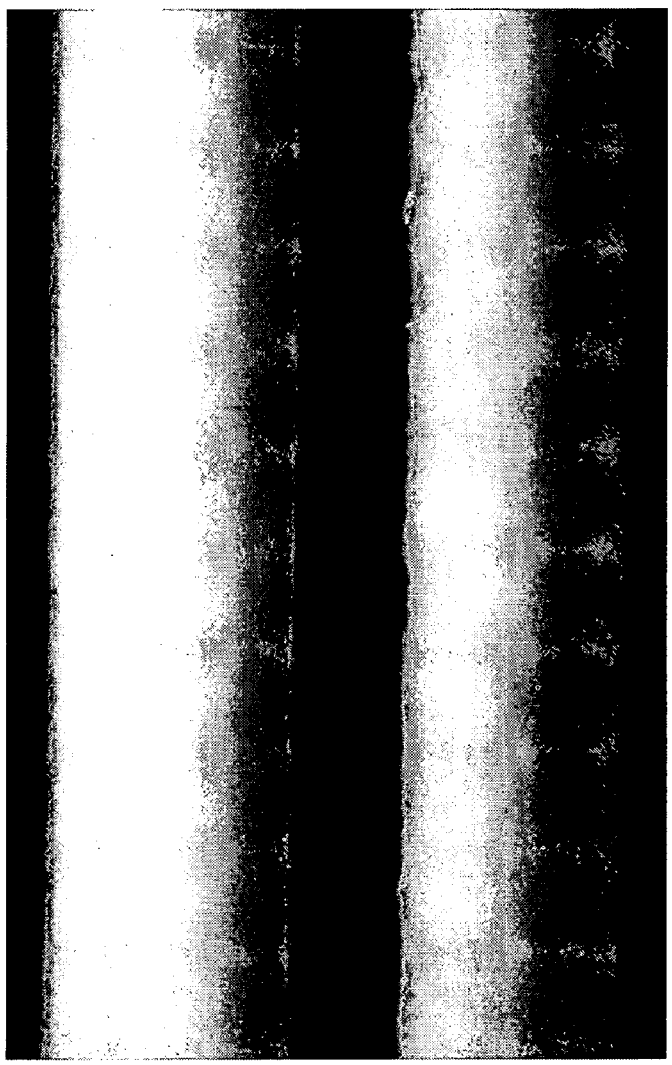
FIG. 52 shows a fiber with PAN membrane and an uncoated fiber.

FIG. 52 illustrates a fiber with PAN membrane (shown at top) and an original CW/TPR fiber (before coating). In order to obtain the coating, a solution of 2-10% PAN in dimethylformamide (DMF) is prepared. Existing fibers with conventional extraction phases are then coated with PAN by dipping them for 2 min in the solution of PAN. The fibers are removed slowly from the solution, are allowed to dry under flowing nitrogen, and are finally cured by a short exposure (5 s) to a flow of nitrogen at 200° C. The thickness of the PAN protective layer is controlled by the concentration of the solution of PAN in DMF.

In addition to biocompatibility, the resulting fibers offer almost the same extraction capacity as the initial ones.

Figure 53:
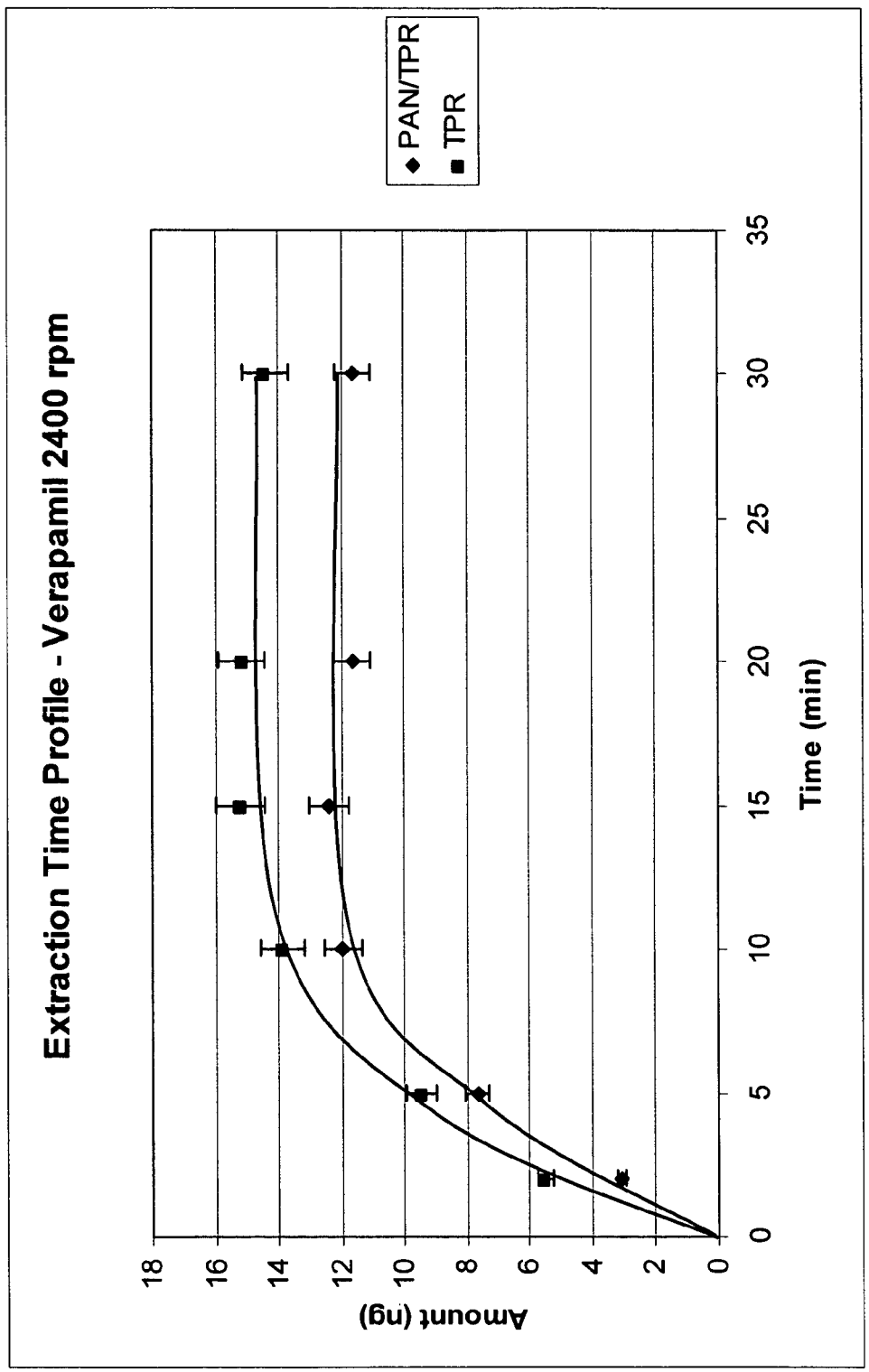
FIG. 53 illustrates the extraction time profile for Verapamil over 30 minutes.

FIG. 53 illustrates the extraction time profile for Verapamil over 30 minutes.

Fibers with C18-Silica Particles Incorporated in PEG. Stainless steel wires (0.005") are first etched by sanding the wires lengthwise in the area to be coated, with 600 grit silicon carbide sanding paper. Wires are then treated sequentially by: sonication in acetone for 20 min; sonication in 6M nitric acid for 20 min; sonication in water for 5 min; coating with a mixture of PEG and C18-silica (both from Supelco, Bellefonte, Pa.), by passing the wires through a pipette tip containing the mixture; and heating at 200° C. for 1 h.

It was noticed that the mixture of C18-silica and PEG produces a much more stable coating than PEG alone. The procedure is not limited to C18-silica. Any particles that are useful as extraction phases in solid-phase extraction and solid-phase microextraction can be used. If some of the non-biocompatible materials (for example C18-silica) still remain exposed on the surface, a new layer of biocompatible polymer (PAN, PEG) can be applied.

Figure 54:
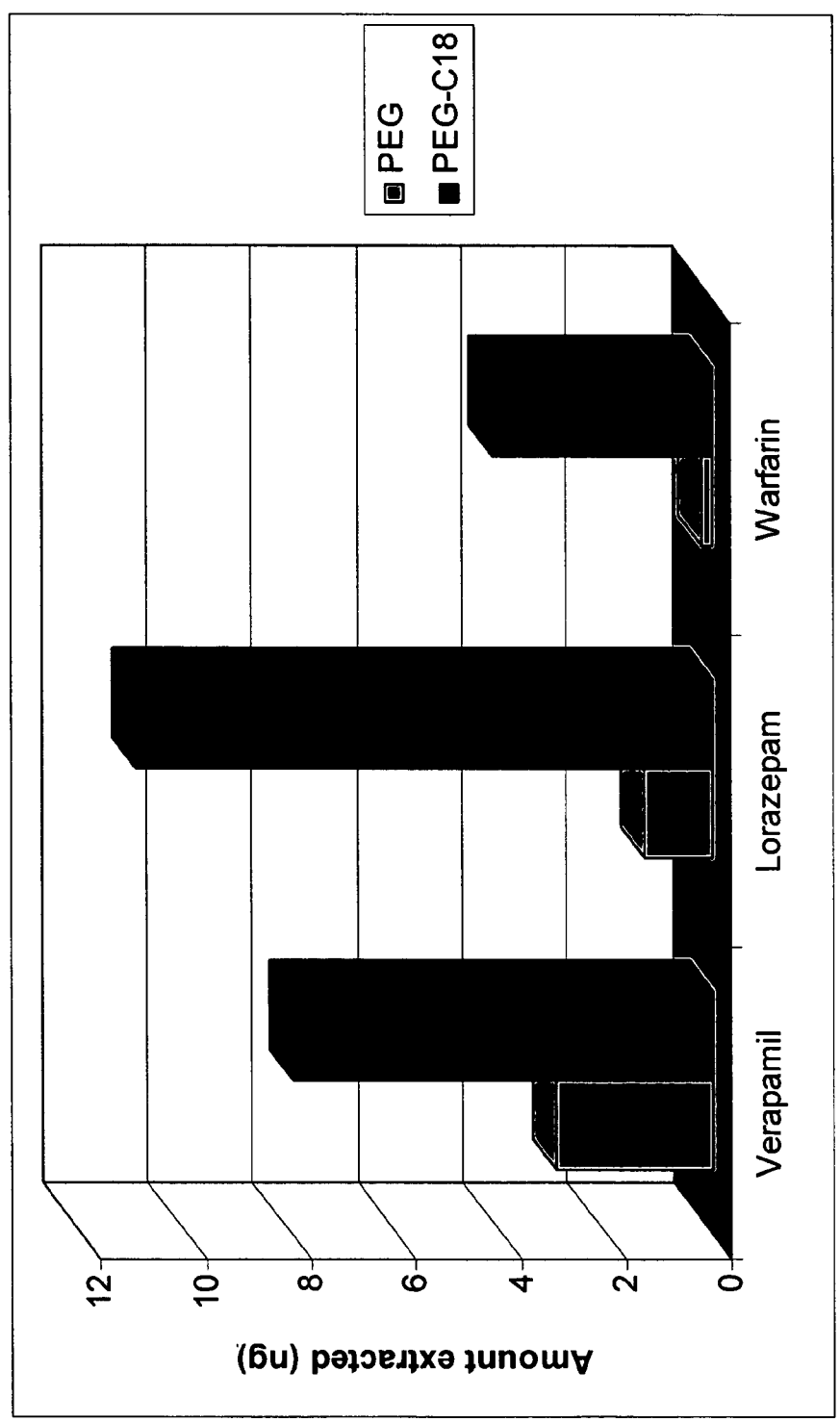
FIG. 54 shows extraction capacity of fibers having C18-silica particles incorporated into a PEG coating.

FIG. 54 illustrates that the fibers containing C18-silica show a significantly higher extraction capacity than fibers prepared with glue only. Extraction of verapamil, lorazepam and warfarin is illustrated.

Many aspects of this technique according to the invention are advantageous. The technique of obtaining biocompatible SPME fibers by enclosing conventional fibers in a protective layer of PAN is unique to this invention. Further, the technique of stabilizing the PAN layer on SPME fibers by heating it at 200° C. under nitrogen flow has not been used previously. The technique of obtaining biocompatible SPME fibers by mixing conventional silica particles with PEG glue and then protecting them further with a PAN or PEG layer is also new. Further, the mixing of coated silica particles with PEG glue in a certain ratio (for example, 1:4 by weight), for obtaining good stability and reproducibility of SPME fiber preparation has not been previously conducted by others.

The PAN solution and the PEG glue can be supplied together with etched stainless steel wires, to allow immobilization of any custom-made particles. The technique would allow the user to transform any extraction phase into a biocompatible one.

The PAN/CW/TPR fibers have a stable-flex silica core and the coating according to this example has a thickness of 70 μm. These fibers offer a high extraction capacity and are perfectly suited for direct off-line extraction of biological samples. For example, when this fiber is used for analysis of verapamil in plasma, the detection limit is 100 pM free verapamil or 1 nM total verapamil.

The PEG/C18 fibers have stainless steel core, are highly flexible and thin (in this example, the core is 63 μm radius and the coating 10 μm thick). These features make them suitable for in-vivo extraction of drugs. For example, when verapamil is analyzed in plasma, the detection limit is 1 nM free verapamil or 10 nM total verapamil. These concentrations are well below the useful therapeutic concentrations, and allow an accurate assay of verapamil, both ex vivo and in vivo.

Analysis of biological samples with these fibers greatly reduces the amount of time required when using standard sample preparation techniques, and limits the exposure of the analytical personnel to infectious bio-fluids.

EXAMPLE 13

Immunoaffinity Coatings

In this example, probes comprise coatings aimed at immunoaffinity detection. A method of attaching of antibody or aptimer to metal or metal alloy surface is described. The method comprises the steps of: pre-treating the metal or metal alloy surface to accept a polymer; coating the surface with a polymer primer solution and heating at successively higher temperatures to form a primed surface; coating the primed surface with a polymer solution followed by heating at successively higher temperatures to form a coated surface having carboxyl groups available for immobilization of an antibody or aptimer thereon; immobilizing an antibody or aptimer to the carboxyl groups to form a probe; and deactivating unbound active sites by soaking the probes in a deactivation solution.

Polyimide Wires for Antibody Immobilization. Antibodies have been immobilized to solid-phase microextraction probes for the purpose of extracting chemicals or other compounds of interest from samples, in order to quantify the amount of the compound of interest present in the sample by the technique of solid-phase microextraction. The immobilization is by covalent attachment rather than surface adsorption, as this provides a more robust and reliable probe.

To date antibodies have been immobilized to the surface of a glass rod using standard techniques (Yuan et al. (2001) Analyst 126, 1456-1461). While this produces an acceptable probe, it is not particularly robust. For some applications, for instance in automated use or for in vivo analysis, it is preferable to have a more durable product, typically by applying the coating to a metal wire. There are, however, no standard techniques for immobilizing antibodies covalently to a metal surface. Also, a bare metal surface will itself adsorb many chemicals from a sample, which would compete with the antibody sorption. A metal surface must be passified against this sorption as well. For all of these reasons the coating of antibodies to a metal wires is significantly more involved. We have developed a procedure to coat wires with the polymer polyimide and chemically modify it to allow covalent attachment of antibodies. The polymer itself significantly passifies the metal surface from competitive adsorption of analytes. In addition we have developed a final passivation method to deactivate the active sites remaining after antibody immobilization.

Steps in Polyimide Probe Preparation. In the procedure, stainless steel wires (304 grade, 0.005"-0.01") are first etched by sanding the wires lengthwise in the area to be coated, with 600 grit silicon carbide sanding paper. Wires are then treated sequentially by 1) sonicating in acetone for 20 minutes, 2) stirring in 5M nitric acid (60° C.) for 20 minutes, 3) stirring in 60° C. acetone for 20 minutes, 4) soaking in N-methyl-2-pyrrolidinone for at least 2 hours, 5) coating three times with primer solution, followed by 6) coating twice with Torlon® AI-10 coating solution. The primer solution consists of 200 mg Torlon® AI 10 powder dissolved in 4 mL NMP. The Torlon® AI-10 coating solution is prepared by dissolving Torlon® AI-10 powder in N-methyl-2-pyrrolidinone to a polymer concentration of 24%. This is then mixed with pyridine in the ratio of 2:1 Torlon® solution to pyridine. Torlon® AI 10 is a product of Solvay Advanced Polymers (Alpharetta, Ga.).

In each of the three primer solution coating steps, wires are soaked in primer solution for 5-10 minutes, heated at 75-85° C. for 20 minutes and then heated at 95-100° C. for 2 minutes. In each of the two Torlon® coatings wires are dipped in coating solution for 2-5 minutes. Excess solution is allowed to run off and remaining solution is spread along the lower half of the wire by passing it back and forth through a narrow orifice for 10-20 times, or until the coating is smooth. Wires are then heated at 75-85° C. for 20 minutes and then heated at 95-100° C. for 20 minutes. Coated wires are then soaked in water for a minimum of two hours. All temperatures quoted are approximate (+/−10° C.) as the equipment used did not have an accurate temperature readout at the location of the probes.

To immobilize antibodies, wires were first soaked in 1 mL of EDC solution for 15 minutes to activate the surface: EDC 2 mM, sulfo-NHS 5 mM in MES buffer. EDC is 1-ethyl-3-(3-dimethylaminopropyl)carbodiimide hydrochloride and sulfo-NHS is N-hydroxysulfosuccinimide. MES buffer is 0.1 M 2-[N-morpholino]ethane sulfonic acid, 0.5 M NaCl adjusted to pH 6.0 with 5M NaOH. After activation wires were briefly rinsed with water and placed in 1 mL of MES containing 1.4 uL of β-mercaptoethanol for 5 minutes. Wires were rinsed with water and placed in the antibody solution (0.4 mg/mL) in phosphate buffered saline (PBS) for two hours. Wires were again rinsed with water and placed in 0.05M Trizma overnight. Wires were stored in PBS containing 0.05% sodium azide at 4° C.

The nature of the antibody solution used depends on the analysis to be performed, ie. if the goal is to measured drugs from the class 'benzodiazepines' an anti-benzodiazepine antibody would be immobilized. Wires are used to extract compounds of interest from an aqueous sample by soaking the wires in the sample for a period of time, normally 10-30 min. After being removed from the sample wires are briefly rinsed and soaked in a solution to desorb extracted analyte from the surface. Desorption solution is typically 75% methanol in water. This desorption solution may then be introduced to an analytical instrument to determine nature and amount of compound extracted. The amount of compound extracted may be related to the concentration of analyte in solution by way of an appropriate calibration.

There is a literature method for coating metal sensor chips for Surface Acoustic Wave Sensors with poly(imide), for the purpose of passivating the metal surface and permitting covalent attachment of antibodies (Wessa et al., (1999) Biosensors & Bioelectroics, 14: 93-98). In this case the authors used non-commercially available polymer starting materials. When their techniques were applied for the above probe preparation using the commercially available polyimide polymer, the immobilization of antibody was entirely unsuccessful.

Using polyimide wires for antibody immobilization has a number of advantageous aspects. The technique involves coating the polymer evenly on the wire surface, including pre-treatment of the surface to accept the polymer, priming of the wire surface with polymer primer solution including coating and heating at successively higher temperatures for certain times at each temperature, followed by coating of the wire with polymer solution followed by heating at successively higher temperatures for certain times at each temperature.

The technique allows for optimising the degree of curing, through heating at successively higher temperatures for certain times at each temperature to produce a polymer that retains a sufficient number of carboxyl groups. This allows efficient immobilization of antibodies, while also attaining sufficient curing to be stable and robust to the manipulations and treatments by chemicals required for use of the final probes.

The technique permits deactivation of remaining active sites in the polymer so as to eliminate non-specific binding of analyte or other sample components by soaking the probes in a deactivation solution for a set period of time.

The polymer, as supplied and prepared by the manufacturer may not coat very well on the stainless steel wires. The polymer solution forms into beads and so the resulting coating is quite uneven. The technique described herein solves this problem, producing a smooth, even thickness coating. In the previously published technique for immobilizing proteins to Surface Acoustic Wave Sensors by means of a polyimide coating, the polymer was completely cured, followed by a chemical treatment to re-expose carboxyl groups. By this previous technique, only a small amount of protein may be immobilized, and certainly not enough to allow it to be used for quantification. The technique according to the instant invention permits a greater surface binding density of antibody, in line with literature methods. Finally, the treatment with 50 mM Trizma after protein immobilization deactivates any remaining active sites on the polymer, to produce an extremely inert surface, which exhibits little if any non-specific binding of analyte or other sample components. In the previous report of Wessa et al., (1999) Biosensors & Bioelectronics, 14:93-93, the authors did not address the issue of deactivating the polyimide after protein immobilization. Several compounds are recommended in the literature for deactivation of a surface, but not all of them work well with the activated polyimide surface and some actually increase the degree of non-specific binding in the polymer.

The probe preparation as described could be marketed as a probe with the antibody of interest pre-loaded, or as a pre-activate surface to which the end user could immobilize a protein of interest, depending on whether the activated surface produced can retain its activity for long periods. The active carboxyls on the polymer surface can, for example, be converted to glutaraldehyde functionality in order to achieve a longer activity period. A glutaraldehyde activated surface is stable at room temperature for very long time periods. The chemistry for this modification would be clear to those of skill in the art. This would allow the marketing of a stable pre-activated surface, to which an end user could easily immobilize a desired protein.

Further advantages of the immobilized antibody probe are its specificity (will not extract non-target analytes) and sensitivity. The specificity of the probe is determined by the nature of the antibody bound and can be user-determined or tuned for a specific application by a supplier. This will allow the analysis of the presence of compounds at very low concentrations in the presence of other substances at higher concentrations because competitive extraction is effectively eliminated. Additionally, the probes are suitable for analysis of compounds at concentrations significantly below that achievable by other techniques. For instance, in the analysis of 7-aminoflunitrazepam from urine (analysed for to verify drug assisted sexual assault) antibody probes are capable of detecting levels as low as 0.01 ng/mL, which is three to four orders of magnitude lower than conventional tests available in hospitals and in line with the most sensitive tests available. Because of its simplicity, such a technique could be used in a variety of clinical and law enforcement settings, as compared to the specialty laboratories presently required to conduct high sensitivity testing. This would reduce the time required to verifying a drugging from the current time of up to a week or more, to allow for fast screening in a clinical setting.

A probe so coated would be beneficial for use in analysis of complex samples where co-extraction of various sample components is problematic by other methods, and for determination of extremely low analyte concentrations that are difficult to analyse by other methods. An advantage of a polyimide coated probe over other competing techniques for similar analyses is the simplicity of this technique, which can save time and money required for an analysis. Finally, because of the possibility of making probes of small dimensions, there is potential application for use in a 'brush-like' device for parallel extraction from many samples at once, or for sampling of very small volumes or spaces for in vivo analysis. For instance the probe may be used for monitoring analyte concentrations directly from the effluent line in microdialysis experiments.

EXAMPLE 14

Hydrophilic Polypyrrole Coatings on Wires, Standards in the Extraction Phase, and Fabrication of Fiber-in-Hypodermic-Needle for Use in a Biological System An alternative method is described herein, encompassing the preparation of hydrophilic PPY coatings, new samplers based on fiber-in-hypodermic-needle and in-vivo calibration based on the standard on the fiber approach. Use of PEG/ C18 coatings as described in Example 12 is also presented. Methods used herein that are identical to those in Example 1 are not described.

PPY coating technology is the same as in Example 1, except for the addition of triethylene glycol to the coating solution. This modification results in the preparation of a more hydrophilic and porous PPY; whereas the equilibration time for PPY fibers described in Example 1 is 30 min, hydrophilic PPY fibers reach equilibrium in as little as 2 min, at a low blood flow rate.

Figure 55:
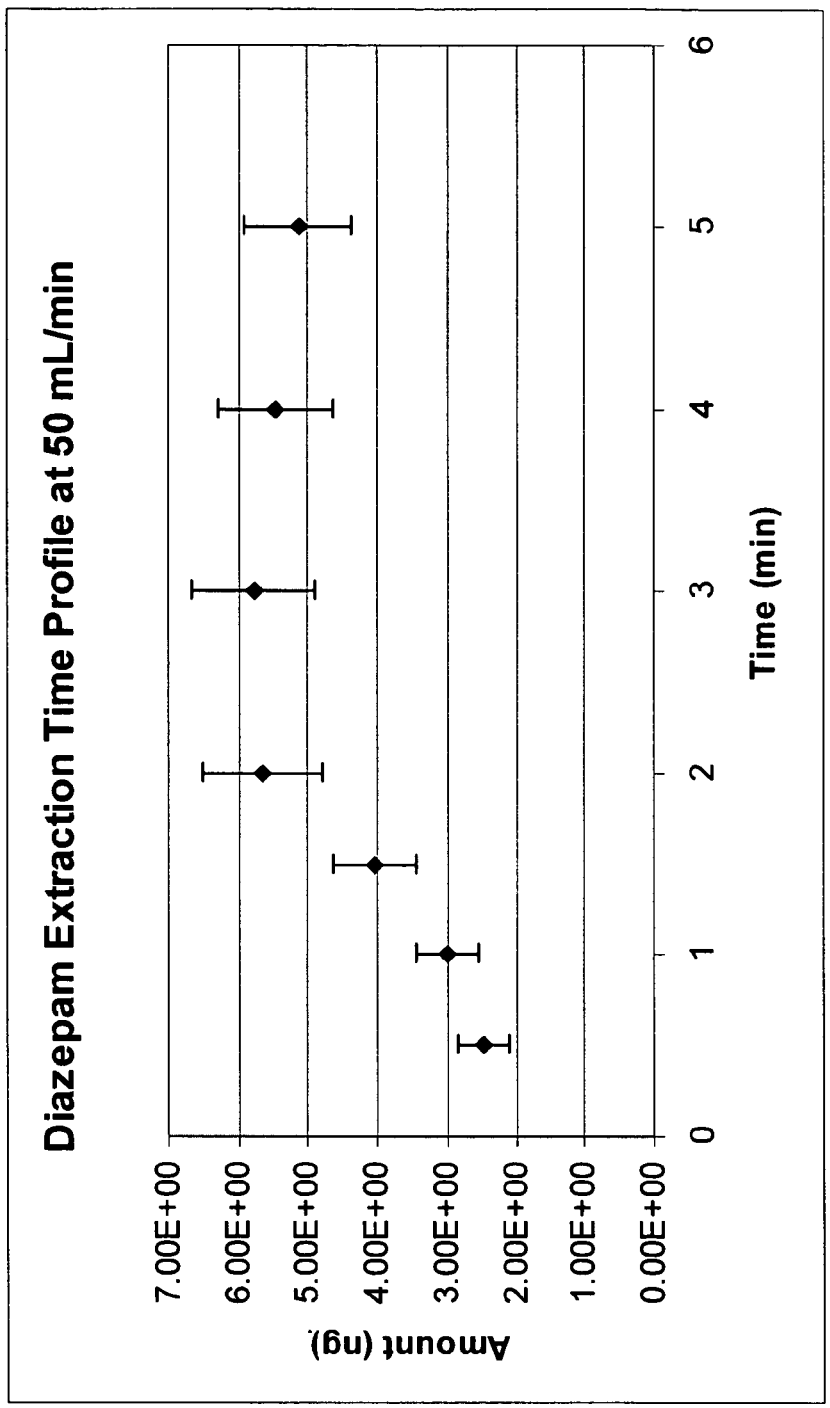
FIG. 55 illustrates Diazepam extraction at an intermediate to low flow rate of 50

FIG. 55 illustrates Diazepam extraction at an intermediate to low flow rate of 50 mL/min. Normal blood flow rate in the cephalic vein of the beagle dog can be as high as 300 mL/min. Accordingly, 2 min extraction time ensures that the coating reaches equilibrium.

The reduction of the sampling time to 2 min provides many advantages: convenience of sampling, possibility to monitor drugs with short in-vivo life time, and better correlation with conventional plasma analysis.

An in-vivo sampling device was built inside a stainless steel hypodermic needle (21 G by 2 in, BD Canada). The 0.005" wire coated with polypyrrole was introduced in a suitable hypodermic tube for reinforcement, leaving the coated part outside. The hypodermic tube was then introduced inside the needle, sealed with silicone glue, and the upper part was formed into a handle. The new device build in medical-grade hypodermic needles offers sampling convenience, guaranteed biocompatibility, minimal exposure to blood, and ease of use in conjunction with the "Multi-Well Device for Performing Parallel SPME Operations" described in Example 6. In particular, FIG. 28 illustrates how the fiber assemblies 224 consisting of the fiber contained in the needle are transported in multiwell plate 218 to the sampling site in the sealed position to prevent contamination of sterile fibers and to prevent loss of calibrant if present in the coating. After the experiment is completed the fiber assemblies can be placed in the holding cover 248 sealed by the holding plate 265 as FIG. 32 illustrates. The sealing prevents loss of extracted components of interests or contamination of the fiber. The fibers are then transported to laboratory in this state. In the laboratory the sealing plate 265 is removed and placed on top of the multiwell plate 260 as FIG. 31 illustrates each well containing desorption solvent. The fibers are lowered to the desorption solvent simultaneously. The desorption can be accelerated by agitating the holding cover/multiwell plate system using for example the orbital shaker. Then the desorption solvent with desorbed components of interest is introduced to LC/MS instrumentation or optionally reconstituted to be more compatible with the mobile phase. Optionally, the fibers could be desorbed directly into an analytical instrument.

Calibration was done by using two procedures: (1) a comparison with results from an external calibration in whole blood similar to that shown in FIG. 12; and (2) a standard on the fiber approach. For the second approach, the fibers (PPY and PEG/C18 described in Example 12) were pre-loaded with labeled diazepam (diazepam-D5, Cerilliant, Austin Tex.) by extraction from a solution with 50 ng/mL diazepam-D5 in PBS. On average, PPY fibers were pre-loaded with 129 ng and PEG/C18 fibers with 770 ng diazepam-D5.

The fibers pre-loaded with standard were exposed to the blood flow for 0.5 min in the case of PPY and 1 min in the case of PEG/C18 fibers. Even though the equilibration time is a little longer for PEG/C18, these fibers offer a 5-fold increase in sensitivity because of higher capacity of the coating.

Figure 56:
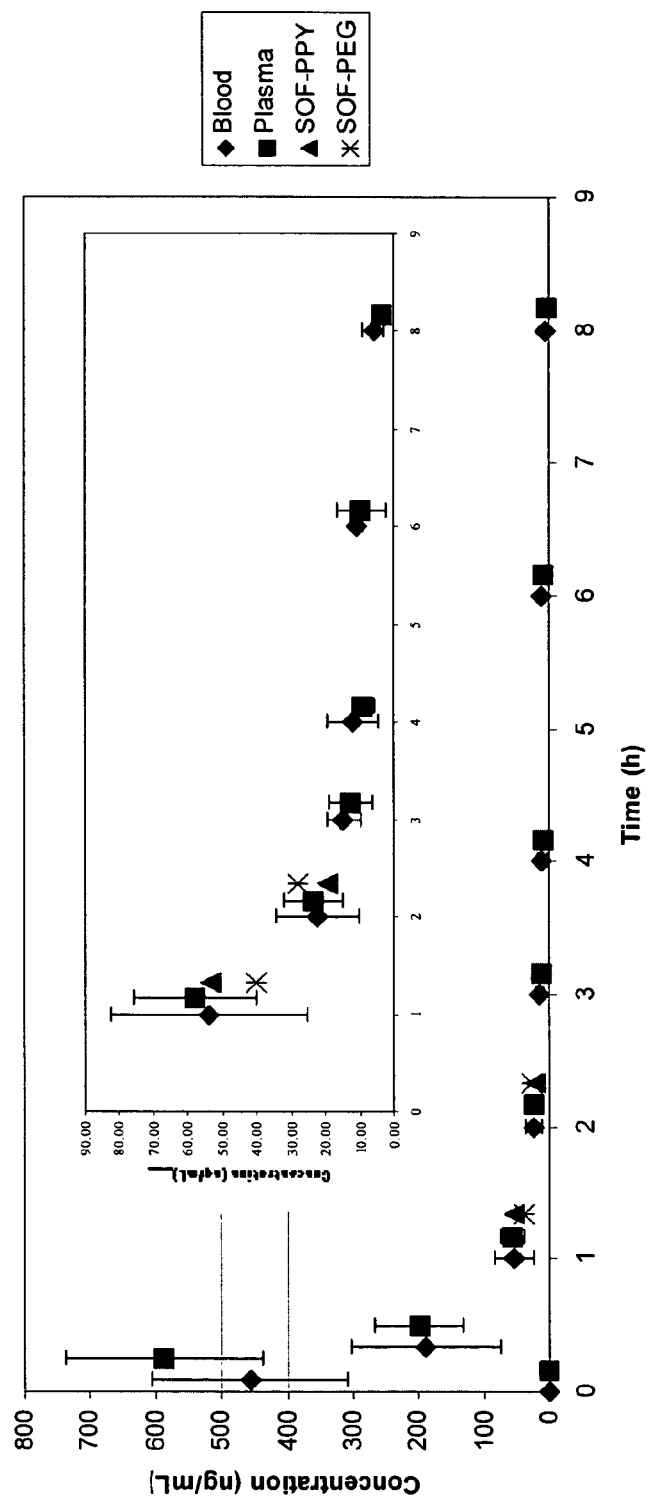
FIG. 56 illustrates a pharmacokinetic profile for Diazepam.
Figure 57:
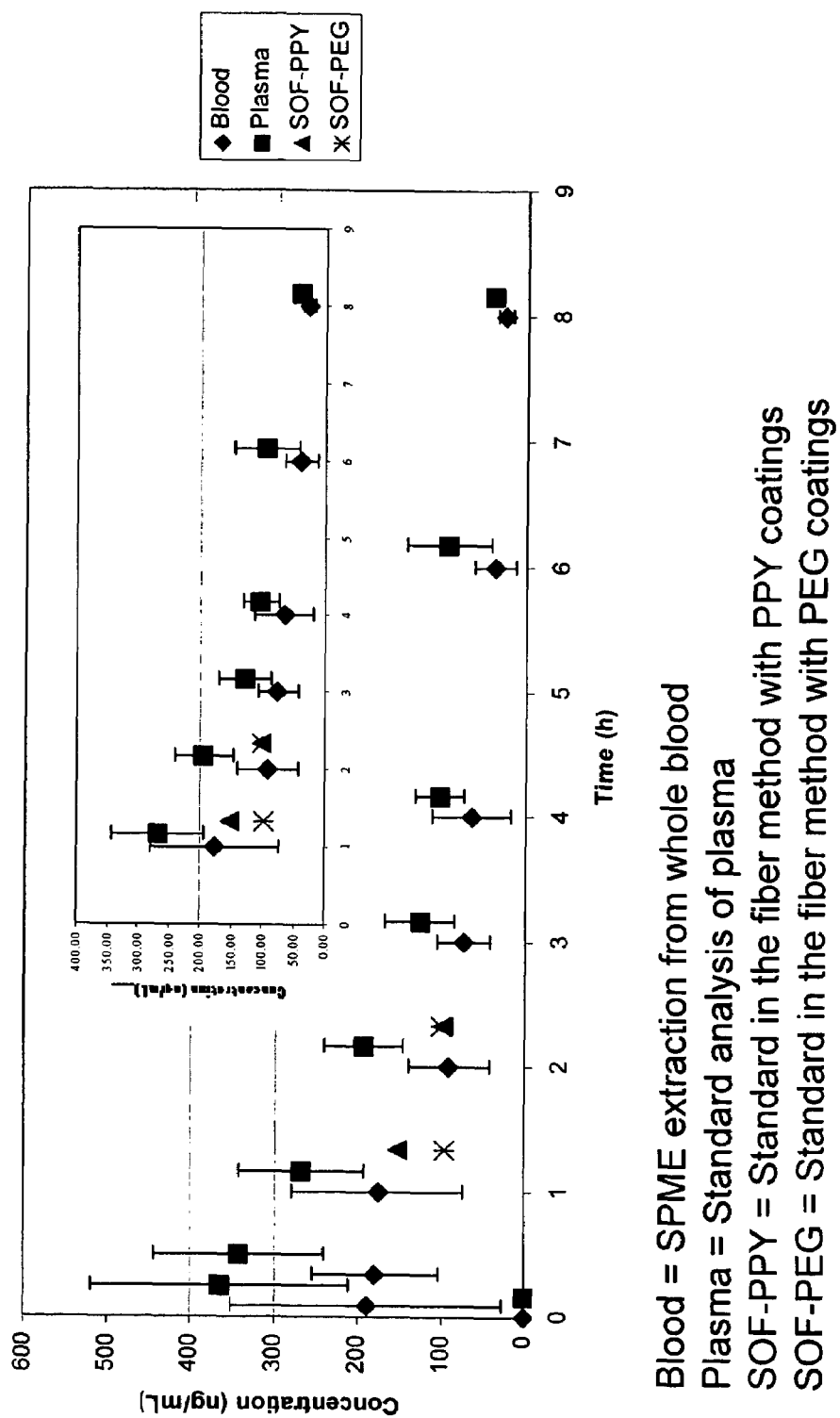
FIG. 57 illustrates a pharmacokinetic profile for Nordiazepam.
Figure 58:
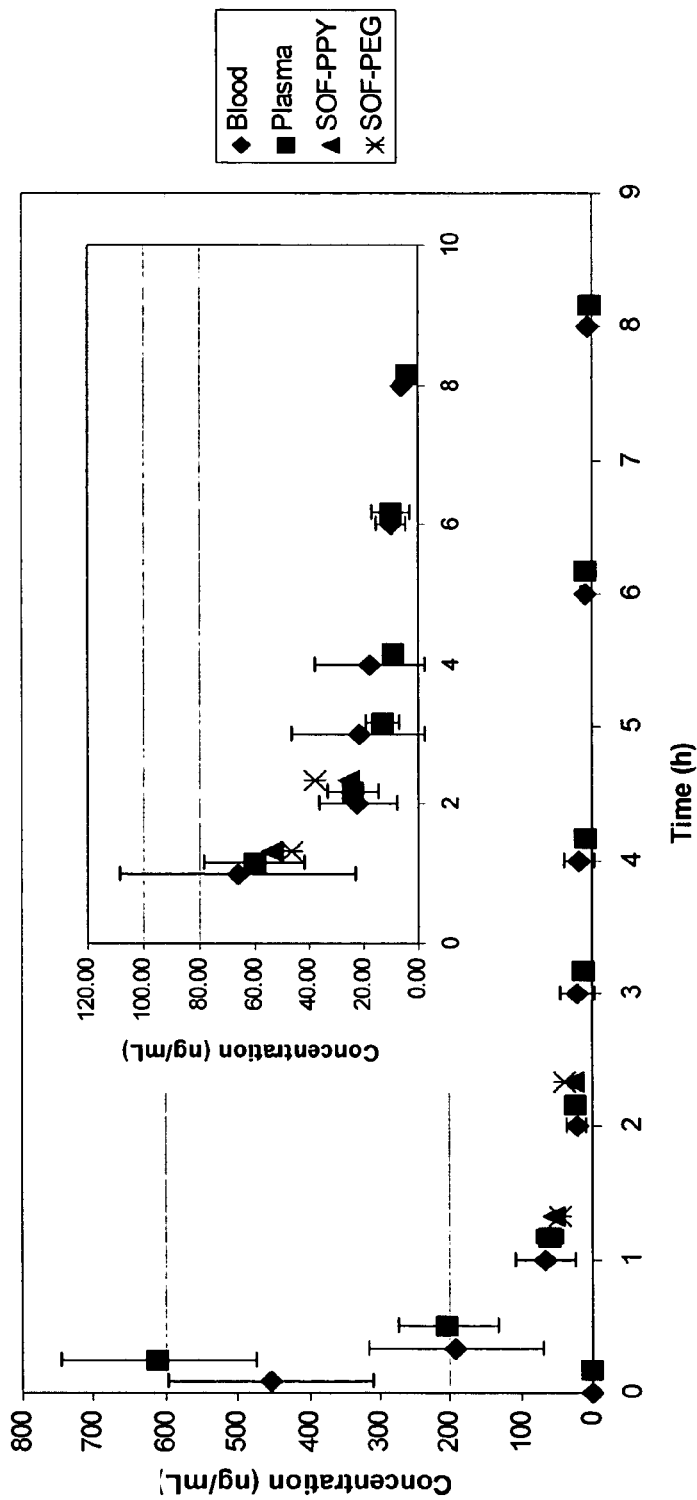
FIG. 58 illustrates a pharmacokinetic profile for Oxazepam.

FIG. 56, FIG. 57 and FIG. 58 show the results of the use of the fiber-in-hypodermic needle device for the catheter sampling method described above, for a pharmacokinetic study in dogs. In this case dogs were dosed with 0.5 mg diazepam per kg at time 0:00. Multiple samplings were performed from a catheter over an interval of 8 hours. Besides the results obtained with external calibration and standard on the fiber calibration, also shown is a comparison to results obtained by multiple blood draws over the same time period, with conventional sample preparation and analysis.

FIG. 56 illustrates a pharmacokinetic profile for Diazepam based on an average of 9 experiments (3 times on 3 dogs). FIG. 57 illustrates a pharmacokinetic profile for Nordiazepam based on an average of 9 experiments (3 times on 3 dogs). FIG. 58 illustrates a pharmacokinetic profile for Oxazepam based on an average of 9 experiments (3 times on 3 dogs).

These results demonstrate that the device is useful for the application described and that the method described produces results in good agreement with devices and methods using more invasive prior art sampling techniques. PEG/C18 phase showed similar biocompatibility during the experiment compared to PPY coating. The calibrant in the fiber approach was investigated for both PPY and PEG/C18 coating for quantification of concentration of components of interests (Diazapam, Oxazepam and Nordiazepam). The internal standard calibration with calibrant (Diazapan D5) in the fiber coating gave results similar to that obtained by using external calibration in blood matrix within the RSD of the measurement for these time points.

The above-described embodiments of the present invention are intended to be examples only. Alterations, modifications and variations may be effected to the particular embodiments by those of skill in the art without departing from the scope of the invention, which is defined solely by the claims appended hereto.

The inventioned claimed is:

1. A solid-phase microextraction device for measuring or identifying one or more components of interest from liquid samples arranged in a plurality of wells in a multiwell plate, said device comprising:
   a plurality of non-porous fibres, each having a distal end at least partially coated with a polymeric extraction phase for absorbing or adsorbing the component of interest from the liquid samples; and
   a positioning device for guiding the coated distal end of said non-porous fibres into a submerged position within the plurality of wells of a multiwell plate, and for removing said non-porous fibres from said wells;
   said positioning device comprising:
   (i) a mounting plate for mounting each of a plurality of non-porous fibres in a position corresponding to a counterpart well on said multiwell plate, the non-porous fibres being retractably mounted within the mounting plate; and
   (ii) a guide for moving said mounting plate so the coated distal end of each of said non-porous fibres is submerged in a well of the multiwell plate, for retracting said non-porous fibres from said wells, and for positioning said non-porous fibres into a multiwell plate containing desorption solvent or into an analytical instrument.

2. The device of claim 1, additionally comprising a multiwell plate having a plurality of wells formed therein; said wells having openings dimensioned to produce an air tight seal around said fibre upon placement of said non-porous fibre in a well.

3. The device of claim 1 wherein the said guide or said positioning device is a component of a robotic system.

4. The device of claim 1, additionally comprising an agitator for:
   agitating during contact of said non-porous fibres with said sample; or
   agitating when said non-porous fibres are submerged in the wells.

5. The device of claim 4 wherein said agitator is an orbital shaker, a sonicator, a vibrator or a stirrer.

6. The device of claim 1 wherein said positioning device is a component of an autosampler or a robotic system.

7. The device of claim 1 comprising more than one non-porous fibre per well having the same or different extraction phase.

8. The device of claim 1 wherein said polymeric extraction phase comprises substituted or unsubstituted poly (dimethylsiloxane), polyacrylate, poly (ethylene glycol), poly (divinyl benzene), ionic liquid or polypyrrole.

9. The device of claim 1 wherein the said extraction phase comprises a bioaffinity agent.

10. The device of claim 9 wherein said bioaffinity agent is selected from the group consisting of a selective cavity, a molecular recognition moiety, a molecularly imprinted polymer, and an immobilized antibody.

11. The device of claim 1, wherein the said non-porous fibres are made of metal, metal alloy or fused silica.

12. The device of claim 1, wherein said extraction phase is at least partially coated with a biocompatible protection layer.

13. The device of claim 12, wherein said protection layer is selected from poly (ethylene glycol), poly(hydroxyethyl methacrylate), poly(acrylamide), poly(N, N-di methyl acrylamide), dextran, poly(acrylonitrile), poly(urethane) and derivatized cellulose.

14. The device of claim 13 wherein the said extraction phase additionally comprises derivatized silica.

15. The device of claim 1 wherein the said extraction phase comprises a bioaffinity agent selected from the group consisting of a selective cavity, a molecular recognition moiety, a molecularly imprinted polymer, an immobilized antibody, and aptamers.

16. The device of claim 15 wherein said immobilized antibody is attached to metal or metal alloy wire coated with polyimide prepared by uniform coating of said polymer.

17. The device of claim 1, wherein said extraction phase comprises a mixture of derivatized silica and poly (ethylene glycol).

18. The device of claim 1, wherein said extraction phase contains a calibrant.

19. The device of claim 2 wherein said plurality of wells have two positions:
   a closed position where the non-porous fibre is sealed in the well; and
   an opened position where the fibre can be exposed to sample, desorption solvent or an analytical instrument.

20. The device of claim 1 wherein said non-porous fibre comprises a hollow distal end, and wherein an interior surface of the hollow distal end is coated with the extraction phase.

21. The device of claim 20 wherein said non-porous fibre comprises a needle having the extraction phase coated on the interior surface of the hollow distal end.

22. The device of claim 1 wherein said positioning device positions said non-porous fibres into an analytical instrument.

23. A solid-phase microextraction device for measuring or identifying one or more components of interest from liquid samples arranged in a plurality of wells in a multiwell plate, said device comprising:
- a plurality of non-porous fibres, each having a distal end at least partially coated with a polymeric extraction phase for absorbing or adsorbing the component of interest from the liquid samples, said extraction phase being formed as a thin flat membrane in the shape of a fin on the distal end of the non-porous fibres; and
- a positioning device for guiding the coated distal end of said non-porous fibres into a submerged position within the plurality of wells of a multiwell plate, and for removing said non-porous fibres from said wells;
- said positioning device comprising:
  - (i) a mounting plate for mounting each of a plurality of non-porous fibres in a position corresponding to a counterpart well on said multiwell plate, the non-porous fibres being retractably mounted within the mounting plate; and
  - (ii) a guide for moving said mounting plate so the coated distal end of each of said non-porous fibres is submerged in a well of the multiwell plate, for retracting said non-porous fibres from said wells, and for positioning said non-porous fibres into a multiwell plate containing desorption solvent or into an analytical instrument.

24. The device of claim 23, additionally comprising a multiwell plate having a plurality of wells formed therein; said wells having openings dimensioned to produce an air tight seal around said fibre upon placement of said non-porous fibre in a well.

25. The device of claim 23, wherein said guide or positioning device is a component of a robotic system.

26. The device of claim 23, additionally comprising an agitator for:
- agitating during contact of said non-porous fibres with said sample; or
- agitating when said non-porous fibres are submerged in the wells.

27. The device of claim 26 wherein said agitator is an orbital shaker, a sonicator, a vibrator or a stirrer.

28. The device of claim 23 wherein said positioning device is a component of an autosampler or a robotic system.

29. The device of claim 23 comprising more than one non-porous fibre per well having the same or different extraction phase.

30. The device of claim 29 wherein said polymeric extraction phase comprises substituted or unsubstituted poly (dimethylsiloxane), polyacrylate, poly (ethylene glycol), poly(divinyl benzene), ionic liquid or polypyrrole.

31. The device of claim 23 wherein said extraction phase comprises a bioaffinity agent.

32. The device of claim 31 wherein said bioaffinity agent is selected from the group consisting of a selective cavity, a molecular recognition moiety, a molecularly imprinted polymer, and an immobilized antibody.

33. The device of claim 23, wherein said non-porous fibres are made of metal, metal alloy or fused silica.

34. The device of claim 23, wherein said extraction phase is at least partially coated with a biocompatible protection layer.

35. The device of claim 34, wherein said protection layer is selected from poly (ethylene glycol), poly(hydroxyethyl methacrylate), poly(acrylamide), poly(N, N-di methyl acrylamide), dextran, poly(acrylonitrile), poly(urethane) and derivatized cellulose.

36. The device of claim 35 wherein said extraction phase additionally comprises derivatized silica.

37. The device of claim 23 wherein said extraction phase comprises a bioaffinity agent selected from the group consisting of a selective cavity, a molecular recognition moiety, a molecularly imprinted polymer, an immobilized antibody, and aptamers.

38. The device of claim 37 wherein said immobilized antibody is attached to metal or metal alloy wire coated with polyimide prepared by uniform coating of said polymer.

39. The device of claim 23, wherein said extraction phase comprises a mixture of derivatized silica and poly (ethylene glycol).

40. The device of claim 23, wherein said extraction phase contains a calibrant.

41. The device of claim 24 wherein said plurality of wells have two positions:
- a closed position where the non-porous fibre is sealed in the well; and
  - an opened position where the fibre can be exposed to sample, desorption solvent or an analytical instrument.

42. The device of claim 23 wherein said positioning device positions said non porous fibres into an analytical instrument.

* * * * *

UNITED STATES PATENT AND TRADEMARK OFFICE
CERTIFICATE OF CORRECTION

PATENT NO. : 7,259,019 B2  Page 1 of 1
APPLICATION NO. : 11/206804
DATED : August 21, 2007
INVENTOR(S) : Janusz B. Pawliszyn et al.

It is certified that error appears in the above-identified patent and that said Letters Patent is hereby corrected as shown below:

Column 78, line 1, claim 30, delete "29" and insert therefor --23--.

Signed and Sealed this

Third Day of June, 2008

JON W. DUDAS
*Director of the United States Patent and Trademark Office*